United States Patent
Park et al.

(10) Patent No.: US 10,527,494 B2
(45) Date of Patent: Jan. 7, 2020

(54) SUBSTRATE ON WHICH MULTIPLE NANOGAPS ARE FORMED, AND MANUFACTURING METHOD THEREFOR

(71) Applicant: Korea Institute of Machinery & Materials, Daejeon (KR)

(72) Inventors: Sung Gyu Park, Changwon-Si (KR);
Jung Heum Yun, Gimhae-Si (KR);
Dong Ho Kim, Changwon-Si (KR);
Byung Jin Cho, Changwon-Si (KR);
Jung Dae Kwon, Changwon-Si (KR);
Chae Won Mun, Changwon-Si (KR)

(73) Assignee: Korea Intitute of Machinery & Materials, Daejeon (KR)

( * ) Notice: Subject to any disclaimer, the term of this patent is extended or adjusted under 35 U.S.C. 154(b) by 43 days.

(21) Appl. No.: 15/513,597

(22) PCT Filed: Sep. 24, 2015

(86) PCT No.: PCT/KR2015/010066
§ 371 (c)(1),
(2) Date: Mar. 23, 2017

(87) PCT Pub. No.: WO2016/048053
PCT Pub. Date: Mar. 31, 2016

(65) Prior Publication Data
US 2018/0231418 A1    Aug. 16, 2018

(30) Foreign Application Priority Data

Sep. 26, 2014  (KR) ........................ 10-2014-0129531
Sep. 26, 2014  (KR) ........................ 10-2014-0129535
(Continued)

(51) Int. Cl.
*G01J 3/44*      (2006.01)
*G01N 21/65*    (2006.01)
(Continued)

(52) U.S. Cl.
CPC .............. *G01J 3/44* (2013.01); *G01N 21/658* (2013.01)

(58) Field of Classification Search
CPC ....... G01J 3/44; G01N 21/658; G01N 27/028; G01N 2021/651; C23C 14/04;
(Continued)

(56) References Cited

U.S. PATENT DOCUMENTS 5,017,007 A * 5/1991 Milne .................. G01N 21/658
                                                    356/301
5,772,905 A * 6/1998 Chou .................... B29C 59/022
                                                    216/44
(Continued)

FOREIGN PATENT DOCUMENTS

CN        101566570 A    10/2009
CN        102169086 A    8/2011
(Continued)

OTHER PUBLICATIONS

Korean Office Action dated Mar. 31, 2016 issued in corresponding Korean Application No. 10-2014-0129531 (with English translation).

(Continued)

*Primary Examiner* — Mohamed K Amara
(74) *Attorney, Agent, or Firm* — Harness, Dickey & Pierce, P.L.C.

(57) ABSTRACT

The present disclosure relates to a substrate with multiple nano-gaps and a manufacturing method therefor, and more particularly to a multiple nano-gaps substrate with high absorption and capable of using light sources in a wide range, and a manufacturing method therefor.

13 Claims, 30 Drawing Sheets

(30) Foreign Application Priority Data

Sep. 26, 2014 (KR) ........................ 10-2014-0129554
Sep. 26, 2014 (KR) ........................ 10-2014-0129574
Sep. 29, 2014 (KR) ........................ 10-2014-0130608
Sep. 29, 2014 (KR) ........................ 10-2014-0130612

(58) Field of Classification Search
CPC ... C23C 14/024; C23C 16/01; C23C 16/0227;
C23C 14/18; C23C 14/30; C23C 16/26;
G01L 1/18; G03F 7/00; B82Y 40/00
See application file for complete search history.

(56) References Cited

U.S. PATENT DOCUMENTS

| | | | | |
|---|---|---|---|---|
| 7,037,639 B2* | 5/2006 | Voisin | B82Y 10/00 430/313 |
| 7,041,604 B2* | 5/2006 | Miller | B29C 43/003 438/735 |
| 7,157,036 B2* | 1/2007 | Choi | B82Y 10/00 264/264 |
| 7,236,242 B2* | 6/2007 | Kamins | G01N 21/658 356/301 |
| 7,241,395 B2* | 7/2007 | Sreenivasan | B29C 43/021 216/54 |
| 7,307,118 B2* | 12/2007 | Xu | B82Y 10/00 524/462 |
| 7,342,656 B2* | 3/2008 | Islam | G01N 21/658 356/301 |
| 7,365,103 B2* | 4/2008 | Willson | B82Y 10/00 522/172 |
| 7,442,336 B2* | 10/2008 | Choi | B82Y 10/00 264/319 |
| 7,483,130 B2* | 1/2009 | Baumberg | G01N 21/658 356/301 |
| 7,528,948 B2* | 5/2009 | Bratkovski | G01N 21/658 356/301 |
| 7,547,504 B2* | 6/2009 | Sreenivasan | B82Y 10/00 216/44 |
| 7,692,787 B2* | 4/2010 | Fujimaki | G01N 21/65 356/301 |
| 7,759,407 B2* | 7/2010 | Xu | B82Y 10/00 156/272.2 |
| 7,981,481 B2* | 7/2011 | Xu | B82Y 10/00 427/508 |
| 8,076,386 B2* | 12/2011 | Xu | B82Y 10/00 522/1 |
| 8,208,136 B2* | 6/2012 | Ivanov | G01N 21/658 356/301 |
| 8,314,932 B2* | 11/2012 | Ou | G02B 1/12 356/301 |
| 8,349,241 B2* | 1/2013 | Sreenivasan | B29C 43/003 216/44 |
| 8,358,407 B2* | 1/2013 | Hu | G01N 21/658 356/301 |
| 8,358,408 B2* | 1/2013 | Wu | G01N 21/658 356/301 |
| 8,384,892 B2* | 2/2013 | Cunningham | G01N 21/658 356/301 |
| 8,389,375 B2* | 3/2013 | Maxwell | B82Y 10/00 438/255 |
| 8,477,303 B2* | 7/2013 | Bratkovski | G01N 21/658 356/301 |
| 8,520,202 B2* | 8/2013 | Li | G01N 21/658 356/301 |
| 8,557,351 B2* | 10/2013 | Xu | B82Y 10/00 427/553 |
| 9,007,575 B2* | 4/2015 | Chou | G01N 21/6452 356/300 |
| 9,395,304 B2* | 7/2016 | Yang | B82Y 40/00 |
| 9,658,165 B2* | 5/2017 | Sugimoto | G01N 21/658 |
| 9,719,931 B2* | 8/2017 | Chen | G01N 21/658 |
| 9,857,307 B2* | 1/2018 | Chen | G01N 21/658 |
| 2004/0142484 A1* | 7/2004 | Berlin | G01N 21/65 436/171 |
| 2004/0144985 A1* | 7/2004 | Zhang | B82Y 10/00 257/79 |
| 2004/0156108 A1* | 8/2004 | Chou | B29C 33/60 359/566 |
| 2006/0034729 A1* | 2/2006 | Poponin | G01N 21/658 422/82.05 |
| 2006/0061762 A1* | 3/2006 | Dwight | B82Y 30/00 356/301 |
| 2006/0146323 A1* | 7/2006 | Bratkovski | G01N 21/658 356/301 |
| 2007/0040491 A1* | 2/2007 | Mei | H01L 29/42384 313/498 |
| 2007/0153267 A1* | 7/2007 | Wang | G01N 21/648 356/301 |
| 2008/0094621 A1* | 4/2008 | Li | G01J 3/44 356/301 |
| 2008/0145964 A1* | 6/2008 | Linden | B82Y 10/00 438/47 |
| 2009/0149344 A1* | 6/2009 | Zhao | G01N 21/658 506/12 |
| 2009/0231586 A1* | 9/2009 | Murakami | G01N 21/658 356/432 |
| 2010/0006812 A1* | 1/2010 | Xu | B82Y 10/00 257/2 |
| 2010/0078855 A1* | 4/2010 | Chou | B82Y 10/00 264/293 |
| 2010/0078860 A1* | 4/2010 | Yoneda | B29C 37/0003 264/496 |
| 2010/0240144 A1* | 9/2010 | Gilbert | G01N 21/658 436/169 |
| 2010/0321684 A1* | 12/2010 | Bratkovski | G01N 21/658 356/301 |
| 2011/0128536 A1* | 6/2011 | Bond | B82Y 20/00 356/301 |
| 2011/0166045 A1* | 7/2011 | Dhawan | B82Y 10/00 506/39 |
| 2012/0001343 A1* | 1/2012 | Huisinga | H01L 21/76814 257/774 |
| 2012/0050732 A1* | 3/2012 | Lu | B05D 1/204 356/301 |
| 2012/0081703 A1* | 4/2012 | Moskovits | G01N 21/658 356/301 |
| 2012/0086021 A1* | 4/2012 | Wang | G01N 21/658 257/84 |
| 2012/0170033 A1* | 7/2012 | Zhu | G01N 21/658 356/301 |
| 2013/0252275 A1* | 9/2013 | Tokonami | G01N 21/554 435/29 |
| 2014/0041217 A1* | 2/2014 | Ito | G01N 21/658 29/846 |
| 2014/0043605 A1* | 2/2014 | Tseng | G01N 21/658 356/301 |
| 2014/0154668 A1* | 6/2014 | Chou | B82Y 15/00 435/5 |
| 2014/0347661 A1* | 11/2014 | Kim | G01N 21/658 356/301 |
| 2015/0001175 A1* | 1/2015 | Rabiei | B82Y 20/00 216/24 |
| 2015/0204792 A1* | 7/2015 | Shibayama | G01N 21/658 356/301 |
| 2015/0211999 A1* | 7/2015 | Maruyama | G01N 21/658 356/301 |
| 2015/0212000 A1* | 7/2015 | Maruyama | G01N 21/658 356/244 |
| 2015/0212001 A1* | 7/2015 | Ito | G01N 21/658 356/244 |
| 2015/0212002 A1* | 7/2015 | Ito | G01N 21/658 359/241 |
| 2015/0212003 A1* | 7/2015 | Shibayama | G01N 21/658 356/244 |
| 2015/0214143 A1* | 7/2015 | Tsai | H01L 23/5329 257/773 |
| 2015/0219561 A1* | 8/2015 | Ito | G01N 21/658 356/301 |

(56) References Cited

U.S. PATENT DOCUMENTS

| | | | | |
|---|---|---|---|---|
| 2015/0219562 A1* | 8/2015 | Shibayama | ........... | G01N 21/658 356/244 |
| 2015/0233830 A1* | 8/2015 | Ito | .......... | G01N 21/658 356/244 |
| 2015/0233831 A1* | 8/2015 | Ito | .......... | G01N 21/658 356/244 |
| 2015/0233832 A1* | 8/2015 | Maruyama | ........... | G01N 21/658 356/244 |
| 2015/0233833 A1* | 8/2015 | Shibayama | ........... | G01N 21/658 356/244 |
| 2015/0299758 A1* | 10/2015 | Yasuda | ............... | B81C 99/0085 435/30 |
| 2016/0003744 A1* | 1/2016 | Chou | ................. | G01N 21/6486 435/5 |
| 2016/0223467 A1* | 8/2016 | Suh | ....................... | G01N 21/658 |
| 2017/0044605 A1* | 2/2017 | Merriman | ........... | G01N 27/3278 |
| 2017/0052114 A1* | 2/2017 | Lin | ....................... | G01N 21/554 |
| 2018/0050904 A1* | 2/2018 | Gangopadhyay | ..... | B82B 3/0038 |
| 2018/0106749 A1* | 4/2018 | Partel | ................... | G01N 27/307 |

FOREIGN PATENT DOCUMENTS

| | | |
|---|---|---|
| CN | 102565024 A | 7/2012 |
| CN | 102944545 A | 2/2013 |
| KR | 10-2010-0002960 A | 1/2010 |
| KR | 10-0990580 B1 | 10/2010 |
| KR | 10-2011-0097834 A | 8/2011 |
| KR | 10-1097205 B1 | 12/2011 |
| KR | 10-2013-0003843 A | 1/2013 |
| KR | 10-1244879 B1 | 3/2013 |
| KR | 10-2013-0066138 A | 6/2013 |
| WO | WO-2012024006 A2 | 2/2012 |
| WO | WO-2014/025035 A1 | 2/2014 |
| WO | WO-2014/025038 A1 | 2/2014 |

OTHER PUBLICATIONS

Korean Office Action dated Sep. 18, 2015 issued in corresponding Korean Application No. 10-2014-0129535 (with English translation).

Korean Office Action dated Sep. 18, 2015 issued in corresponding Korean Application No. 10-2014-0129554 (with English translation).

Korean Office Action dated Nov. 19, 2015 issued in corresponding Korean Application No. 10-2014-0129574 (with English translation).

Dongxing Wang et al., "Wafer-scale metasurface for total power absorption, local field enhancement and single molecule Raman spectroscopy", Oct. 4, 2013, Scientific Reports, 3:2867, DOI: 10.1038/srep02867.

International Search Report PCT/ISA/210 for International Application No. PCT/KR2015/010066 dated Jan. 8, 2016.

Written Opinion of the International Searching Authority PCT/ISA/237 for International Application No. PCT/KR2015/010066 dated Jan. 8, 2016.

Chinese Office Action for corresponding Application No. 2015-80051781, dated Sep. 17, 2018, English translation thereof.

* cited by examiner

FIG. 2
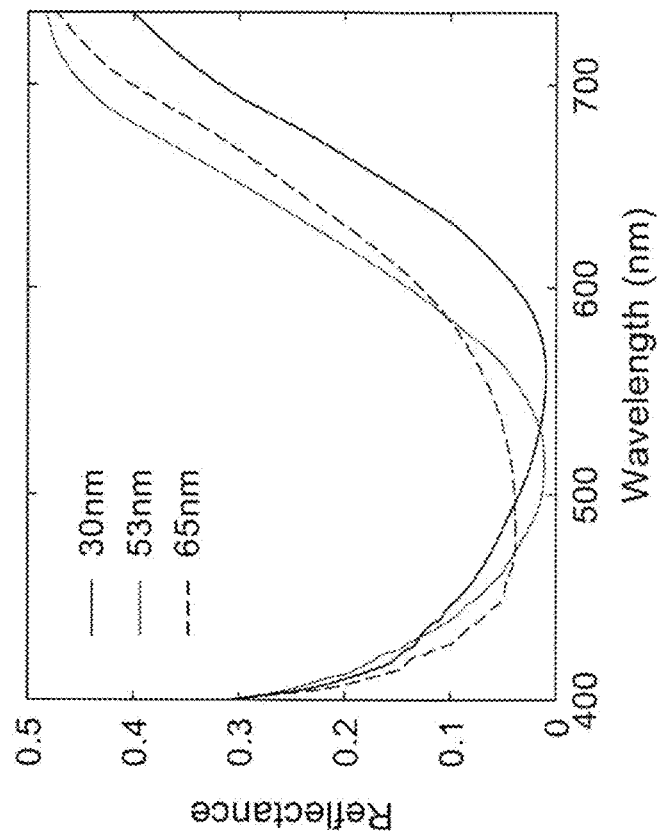
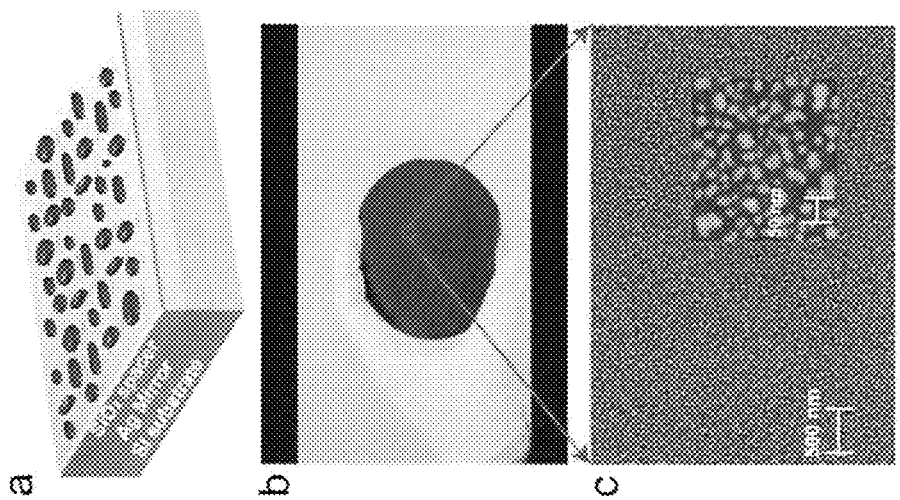
Reflection spectra of SIOM metasurefaces having SiO₂ spacer layers with thicknesses of 30 nm, 53 nm and 65 nm. Inset: images of fabricated SIOM with different thicknesses of SiO₂ layer.

FIG. 33
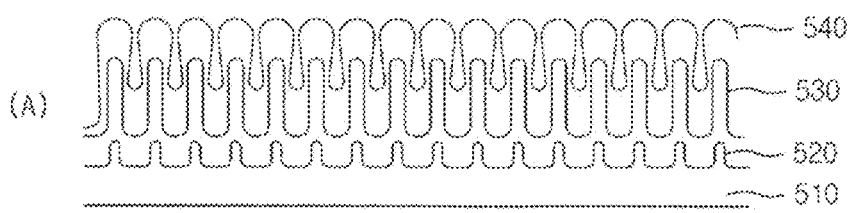
(A)
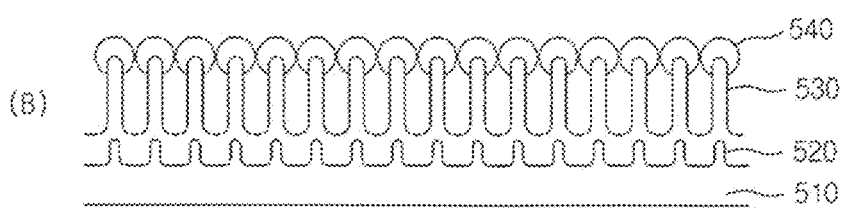
(B)
FIG. 34
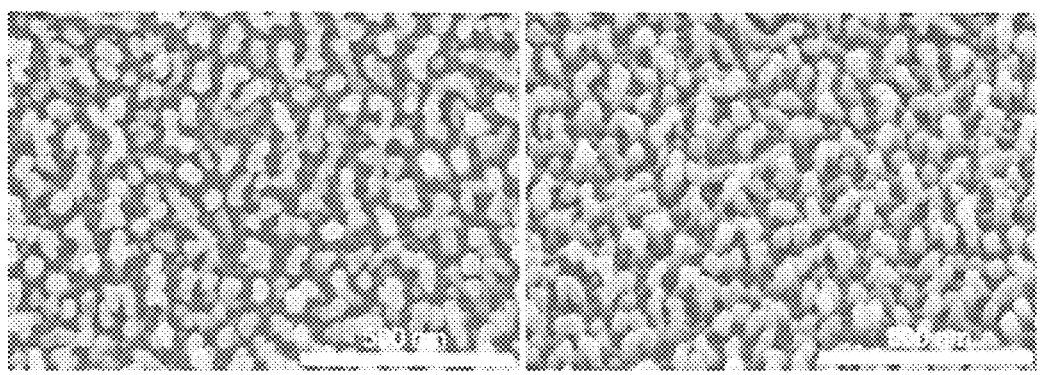

FIG. 35
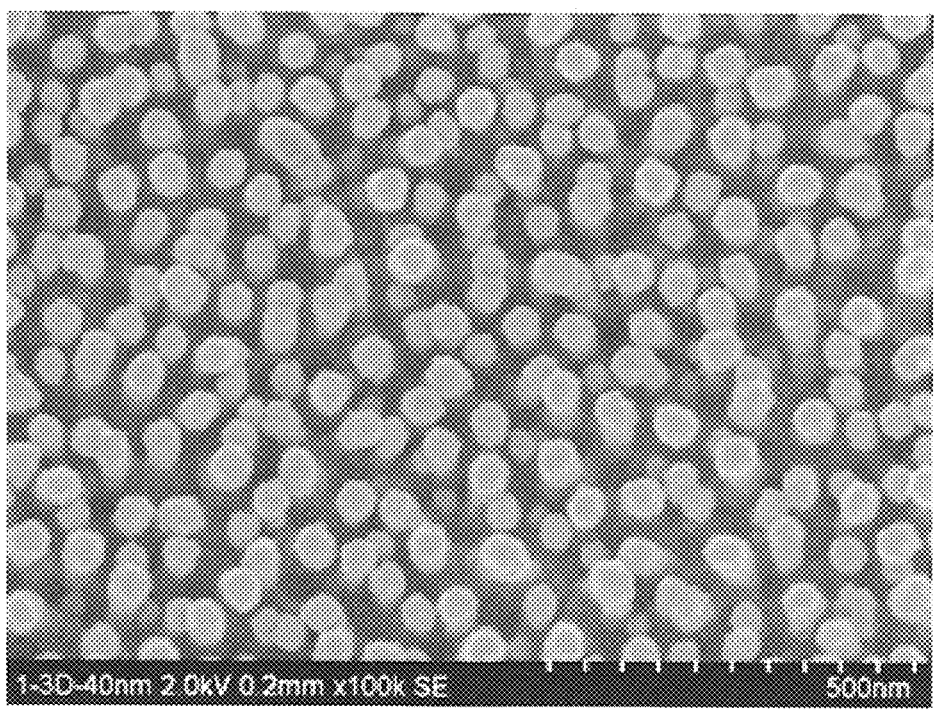
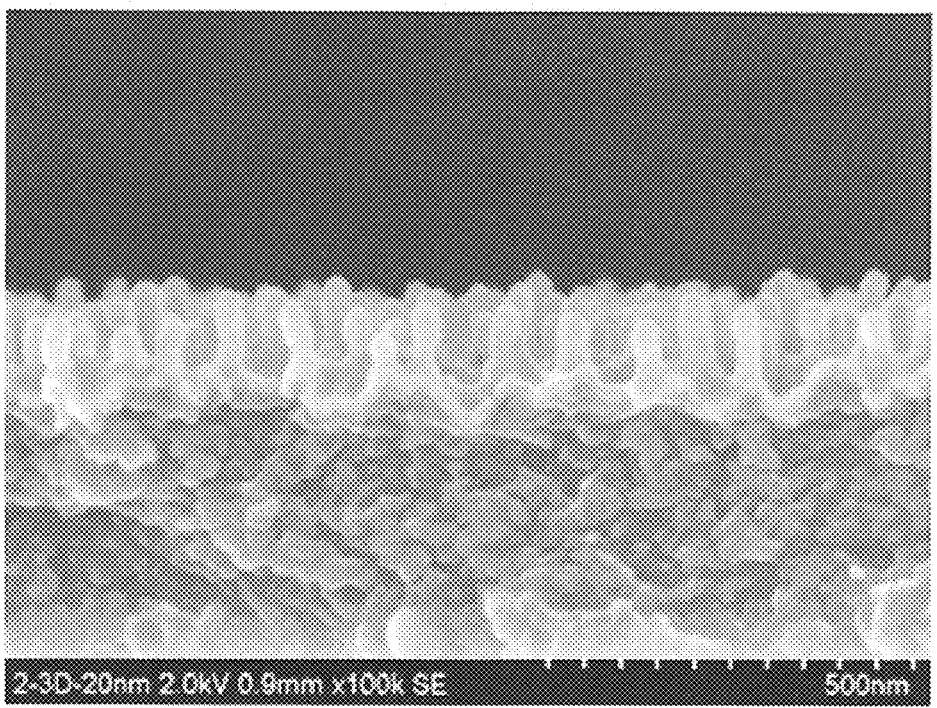

SUBSTRATE ON WHICH MULTIPLE NANOGAPS ARE FORMED, AND MANUFACTURING METHOD THEREFOR

CROSS-REFERENCE TO RELATED APPLICATIONS

This application is the U.S. National Phase application of PCT Application No. PCT/KR2015/010066 filed on Sep. 24, 2015, which claims priority to Korean Application No. 10-2014-0129574 filed on Sep. 26, 2014, Korean Application No. 10-2014-0129535 filed on Sep. 26, 2014, Korean Application No. 10-2014-0129554 filed on Sep. 26, 2014, Korean Application No. 10-2014-0129531 filed on Sep. 26, 2014, Korean Application No. 10-2014-0130612 filed on Sep. 29, 2014 and Korean Application No. 10-2014-0130608 filed on Sep. 29, 2014, the entire contents of each of which are incorporated herein by reference.

BACKGROUND

1. Field

The following description relates to a substrate with multiple nano-gaps and a manufacturing method therefor.

2. Description of Related Art

Raman scattering or the Raman effect is an inelastic photon scattering phenomenon. When photons are scattered from an atom or molecule, most photons are elastically scattered (Rayleigh scattering), such that the scattered photons have the same energy (frequency and wavelength) as the incident photons. A small fraction of the scattered photons (approximately 1 in 10 million) are scattered by an excitation, with the scattered photons having a frequency different from, and usually lower than, that of the incident photons.

Raman effect (Raman shift) is exhibited in almost organic molecules including not only by polar molecules but also by non-polar molecules which have induction polarizability when Raman spectroscopy using Raman scattering is applied. It is thus more suitable for the detection of biomolecules such as proteins, genes and the like since it is not affected by interference caused by water molecules.

On the other hand, specific wavelengths of Raman emission spectrum represent chemical composition and structure features so that it can be used to directly analyze materials using Raman signals.

Even though an analyte can be analyzed directly, it has not been practically used due to very week intensity of signals. However, since 1974 when Fleischmann et al. reported surface-enhanced Raman scattering, studies have been conducted to amplify the intensity of signals.

Techniques using so-called localized surface plasmon resonance (LSPR), which induces surface plasmon resonance by nano-gaps, have been developed as techniques for enhancing Raman signals Conventional techniques for forming multiple nano-gaps include (1) a method of forming plasmonic films of tens of nanometers on a flat Si substrate, forming an insulation layer of several nanometers, and applying plasmonic nanoparticles, and (2) a method of forming a plasmonic film of 120 nanometer on a flat Si substrate, forming an insulation layer ($SiO_2$) of several tens of nanometers, and applying plasmonic nanoparticles.

In the method (1), because the middle insulation layer is only a few nanometers, electromagnetic coupling between the plasmonic nanoparticles and the plasmonic film takes place across the insulation layer, so it may serve as a nano-antenna to confine and scatter specific wavelengths of incident light.

In the method (2), because the middle insulation layer has a thickness of 50 nm, the electromagnetic coupling shown in the method (1) does not occur, and the plasmonic film serves as a mirror that reflects incident light. Electromagnetic coupling occurs only in the nano-gap between plasmonic nanoparticles of the topmost layer.

The method (1) has been introduced in "Controlled-reflectance surfaces with film coupled colloidal nanoantennas" in [Nature, 2012, 492, 86-90, doi: 10.1038/nature11615]. According to FIG. 1, a film of 50 nm gold is deposited on a flat substrate, a 4 nm to 17 nm polymer insulation layer is deposited, and finally a silver nanocube of about 74 nm is applied. Thus, the thickness of the polymer insulation layer in the middle is several nanometers, nanogaps are formed between the gold film and the silver nanoparticles.

This technique can control the peak of LSPR by controlling the polymer insulation layer. However, if the size of the silver nanoparticles or the density is increased to increase the nano-gap forming area, there is a limit to increase the absorption amount than the reflection amount of light. The observed peak range of LSPR is from 600 nm to 830 nm.

The method (2) is introduced in "Wafer-scale metasurface for total power absorption, local field enhancement and single molecule Raman spectroscopy" in [Scientific Report, 2013, 3, 2867, DOI: 10.1038/srep02867]. Referring to FIG. 2, a 120 nm film is deposited on a flat Si substrate, and a $SiO_2$ insulation layer of several tens of nanometers is vacuum deposited. Finally, the silver nanoparticles are vacuum-deposited. Because this technique uses a thick insulation layer, the LSPR does not occur across the insulation layer. The average size of the silver nanoparticles is as small as 15 nm and the reflection dip is reduced to near 0, but the LSPR control range is from 470 nm to 560 nm and the LSPR peak occurs near 500 nm, only 515 nm or 532 nm light source can be used for Raman spectrum measurement. This may be useful as a chemical sensor, but it is limited to use as a biosensor for the wavelength of the light source to be more than 633 nm for non-destruction of biomolecules.

On the other hand, US2013-0252275 A1, which is a patent document for forming nano-gaps, discloses spherical metal nanoparticles formed in cluster form by self-assembly on a substrate.

Conventional techniques for deriving hot spots are mostly based on forming roughness on the surface of the substrate and applying a metal, Raman active material, thereon. These metals may be deposited in the form of thin films or in the form of particles.

This is introduced, for example, in KR 10-2011-0097834, which discloses a substrate having a metal nanostructure having a uniform density by forming a metal layer on a pattern (nanostructure) of an inverted triangle, and a manufacturing method thereof.

Another example is introduced in KR 10-0990580 which discloses a technique comprising forming specific patterns and coating a metal.

Conventional techniques for controlling nano-gaps between nanoparticles include forming metal nanoparticles on a material susceptible to external stimuli such as a hydrogel, and then externally stimulating the hydrogel to control the nano-gap, and forming nanoparticles on a flexible substrate and then connecting them to an actuator to adjust the spacing.

In U.S. Pat. No. 8,477,303 B2 of "Reconfigurable Surface Enhanced Raman Spectroscopy Apparatus, System and Method", discloses a technique for forming metal protuberant structures on a stimulus-sensitive material, followed by stimulation to control the gap between the nanoparticles. This forms a nano-rod on the substrate and positions the stimuli-sensitive material next to the nano-rod to control the gap between the nano-rods using the deformation of the stimuli-sensitive material with external stimuli.

In U.S. Pat. No. 7,342,656 B2 of "Dynamically variable separation among nanoparticles for nano-enhanced Raman spectroscopy (NERS) molecular sensing" discloses a technique for controlling the nano-gap by generating an electrostatic field in nanoparticles as well as using deformation of a piezoelectric material.

In U.S. Pat. No. 7,528,948 B2 of "Controllable Surface Enhanced Raman Spectroscopy" discloses a technique for modifying a flexible substrate using a mechanical actuator to control the spacing of metal-containing nanoparticles formed on the flexible substrate.

These conventional techniques are techniques that require a separate material or an external force to control the nano-gap.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

This disclosure is to provide a substrate with multiple nano-gaps that can widely use the wavelength range of a light source and have high absorption, and a manufacturing method therefor.

Unlike conventional multiple nano-gap technologies, this disclosure is to improve surface plasmon resonance characteristics by introducing the concept of an inorganic material-metal continuous layer. Thus, this disclosure is to provide a substrate with multiple nano-gaps that can achieve amplification of Raman signal by forming multiple nano-gaps, and a manufacturing method therefor.

This disclosure is to provide favorable characteristics of a substrate by forming inorganic-containing particles on a patterned substrate, unlike a conventional technique of applying a metal particle or a metal thin film on a substrate on which a specific pattern is formed, and amplification effect of the Raman signal by forming multiple nano-gaps. Thus, this disclosure is to provide a substrate with inorganic-containing particles which is capable of obtaining advantageous properties by forming inorganic-containing particles and forming multiple nano-gaps to amplify the Raman signal, and a manufacturing method therefor.

This disclosure is to provide favorable characteristics of a substrate by controlling the nano-gaps easily and utilizing an inorganic material-containing thin layer through overcoming the limitations associated with the conventional technique of applying metal particles or a metal thin film on a substrate having a specific pattern formed. Thus, this disclosure is to provide a substrate with inorganic-metal structures which can easily control the nano-gaps and secure adhesion and thermal stability by introducing an inorganic material-containing thin layer, and manufacturing method therefor.

Furthermore, this disclosure is to provide favorable characteristics of a substrate by growing an inorganic material on a patterned substrate, unlike a conventional technique of applying metal particles or a metal thin film on a substrate having a specific patter formed, and by controlling the nano-gap to facilitate the induction of hot spots. Thus, this disclosure is to provide a substrate with inorganic-metal structures which can have thermal stability and readily controlled nano-gaps, and a manufacturing method therefor.

Furthermore, this disclosure is to provide a nano-gap controlled substrate and a manufacturing method therefor in which the nano-gap is controlled without external force by using the stretching of the substrate during the manufacturing process.

A substrate with multiple nano-gaps may comprise a substrate including protuberant structures formed to be spaced-apart on the surface; a metal-containing thin layer formed on the surface of the substrate and the protuberant structures; an insulation layer formed on the metal-containing thin layer; and metal-containing nanoparticles formed on the insulation layer, wherein the metal-containing nanoparticles have nano-gaps with other metal-containing nanoparticles and with the metal-containing thin layer.

The metal-containing thin layer may be formed by vacuum depositing a Raman active material.

The Raman active material may be initially uniformly deposited on the surface of the substrate and the protuberant structures, but be intensively deposited on the upper part of the protuberant structures as the deposition progresses.

The substrate may be a polymer substrate.

The protuberant structures may be formed by any one chosen from plasma etching, soft lithography, embossing, nano imprinting, photolithography, and holographic lithography.

The plasma etching may be performed by using at least one chosen from argon, oxygen, hydrogen, helium, and nitrogen gas.

The metal-containing nanoparticles may be formed by vacuum depositing a Raman active material.

The vacuum deposition may be performed by any one chosen from sputtering, evaporation and chemical vapor deposition.

The Raman active material may be any one chosen from Au, Ag, Cu, Pt, Pd and an alloy thereof.

The insulation layer may be formed by any one chosen from vacuum deposition and solution process.

The vacuum deposition may be performed by any one chosen from atomic layer deposition, chemical vapor deposition, sputtering and thermal evaporation.

The solution process may be performed by any one chosen from spin coating, dip coating and dropping process.

The insulation layer may be formed of any one chosen from metal oxide such as alumina, silica, zirconium, and iron oxide, metal sulfide, and metal halide.

A thickness of the insulation layer may be 0.5 nm to 100 nm.

At least one of the thickness of the insulation layer and the size of the metal nanoparticles may be controlled so that localized surface plasmon resonance is optimal for a specific wavelength.

A Raman spectroscopic device may comprise a light source; a substrate for surface-enhanced Raman spectroscopy; and a detector configured to detect Raman spectrum.

The light source may be a laser.

A method for manufacturing a substrate with multiple nano-gaps may comprise forming protuberant structures to be spaced-apart from each other on the surface of a substrate; forming a metal-containing thin layer on the surface of the substrate and the protuberant structures; forming an insulation layer on the metal-containing thin layer; and forming metal-containing nanoparticles on the insulation layer, wherein the metal-containing nanoparticles may form nano-gaps with other metal-containing nanoparticles and with the metal-containing thin layer.

The metal-containing thin layer may be formed by vacuum depositing a Raman active material. The Raman active material may be initially uniformly deposited on the surface of the substrate and the protuberant structures, but be intensively deposited on the upper part of the protuberant structures as the deposition progresses.

The substrate may be a polymer substrate.

The protuberant structures may be formed by any one chosen from plasma etching, soft lithography, embossing, nano imprinting, photolithography, and holographic lithography.

The plasma etching may be performed by using at least one chosen from argon, oxygen, hydrogen, helium, and nitrogen gas.

The metal-containing nanoparticles may be formed by vacuum depositing a Raman active material.

The vacuum deposition may be performed by any one chosen from sputtering, evaporation, and chemical vapor deposition.

The Raman active material may be any one chosen from Au, Ag, Cu, Pt, Pd and an alloy thereof.

The insulation layer may be formed by any one chosen from vacuum deposition and solution process.

The vacuum deposition may be performed by any one chosen from atomic layer deposition, chemical vapor deposition, sputtering, and thermal evaporation.

The solution process may be performed by any one chosen from spin coating, dip coating and dropping process.

The insulation layer may be formed of any one chosen from metal oxide oxide such as alumina, silica, zirconium, and iron oxide, metal sulfide, and metal halide.

A thickness of the insulation layer may be 0.5 nm to 100 nm.

At least one of the thickness of the insulation layer and the size of the metal nanoparticles may be controlled so that localized surface plasmon resonance is optimal for a specific wavelength.

A substrate with multiple nano-gaps according to an example may comprise a substrate including protuberant structures spaced-apart from each other; metal-containing nanoparticles formed on the surface of the substrate and the protuberant structures; a continuous layer formed between the substrate and the metal-containing nanoparticles and comprising at least one inorganic material-containing thin layer and at least one metal-containing thin layer, wherein nano-gaps are formed between the metal-containing nanoparticles and between the metal-containing nanoparticles and the metal-containing thin layer.

A substrate with multiple nano-gaps according to another example may comprise a substrate including protuberant structures spaced-apart from each other; metal-containing nanoparticles formed on the surface of the substrate and the protuberant structures; and a continuous layer formed inside the metal-containing nanoparticles and comprising at least one inorganic material-containing thin layer and at least one metal-containing thin layer, wherein nano-gaps are formed between the metal-containing nanoparticles and between the metal-containing nanoparticles and the metal-containing thin layer.

The continuous layer may include two metal-containing thin layers and inorganic material-containing thin layer which is formed therebetween and nano-gaps may be formed between the two metal-containing thin layers.

The continuous layer may be formed by sequentially forming an inorganic material-containing thin layer, a metal-containing thin layer and an inorganic material-containing thin layer.

The continuous layer may also be formed by sequentially forming a metal-containing thin layer and an inorganic material-containing thin layer.

The upper part of the protuberant structures may have a larger curvature than the lower part.

The protuberant structures may be formed by any one chosen from nano imprinting, nanolithography, and dry etching.

The dry etching may be a plasma dry etching using at least one gas chosen from argon, oxygen, hydrogen, helium, and nitrogen gas.

The substrate may be formed of any one chosen from acrylic polymers, polyethersulfones (PES), polycycloolefins (PCO), polyurethanes and polycarbonates (PC).

The inorganic material may be any one chosen from an oxide, a nitride, an oxynitride of a metal chosen from Al, Ba, Be, Ca, Cr, Cu, Cd, Dy, Ga, Ge, Hf, In, Lu, Mg, Mo, Ni, Rb, Sc, Si, Sn, Ta, Te, Ti, W, Zn, Zr, and Yb, and magnesium fluoride.

The inorganic material-containing thin layer and the metal-containing thin layer may be formed by any one chosen from chemical vapor deposition, sputtering and evaporation.

The metal-containing nanoparticles may be formed by vacuum depositing a Raman active material. The Raman active material may be initially uniformly deposited on the surface of the substrate and the protuberant structures, but be intensively deposited on the protuberant structures as the deposition progresses.

The metal may be one chosen from Au, Ag, Cu, Pt and Pd, and an alloy thereof.

A method for manufacturing a substrate with multiple nano-gaps according to an example may comprise forming protuberant structures by processing a substrate; forming a continuous layer comprising at least one inorganic material-containing thin layer and at least one metal-containing thin layer on the surface of the substrate and the protuberant structures; and forming metal-containing nanoparticles on the surface of the substrate and the protuberant structures where the continuous layer is formed, wherein nano-gaps are formed between the metal-containing nanoparticles and between the metal-containing nanoparticles and the metal-containing thin layer.

A method for manufacturing a substrate with multiple nano-gaps according to another example may comprise forming protuberant structures by processing a substrate; forming metal-containing nanoparticles on the surface of the substrate and the protuberant structures; and forming a continuous layer comprising at least one inorganic material-containing thin layer and at least one metal-containing thin layer in the middle of the metal-containing nanoparticles, wherein nano-gaps are formed between the metal-containing nanoparticles and between the metal-containing nanoparticles and the metal-containing thin layer.

The continuous layer may include two metal-containing thin layers and an inorganic material-containing thin layer which is formed therebetween, wherein nano-gaps may be formed between the two metal-containing thin layers.

The continuous layer may be formed by sequentially forming an inorganic material-containing thin layer, a metal-containing thin layer and an inorganic material-containing thin layer.

The continuous layer may also be formed by sequentially forming a metal-containing thin layer and an inorganic material-containing thin layer.

The upper part of the protuberant structures may have a larger curvature than the lower part.

The protuberant structures may be formed by any one chosen from plasma etching, soft lithography, embossing, nano imprinting, photolithography, and holographic lithography.

When plasma etching is used, it is performed by using at least one chosen from argon, oxygen, hydrogen, helium, and nitrogen gas.

The substrate may be a polymer substrate chosen from acrylic polymers, polyethersulfone (PES), polycycloolefin (PCO), polyurethane and polycarbonate (PC).

The inorganic material may be any one chosen from an oxide, a nitride, an oxynitride of a metal chosen from Al, Ba, Be, Ca, Cr, Cu, Cd, Dy, Ga, Ge, Hf, In, Lu, Mg, Mo, Ni, Rb, Sc, Si, Sn, Ta, Te, Ti, W, Zn, Zr, and Yb, and magnesium fluoride.

The inorganic material-containing thin layer and the metal-containing nanoparticles may be formed by using any one chosen from chemical vapor deposition, sputtering and evaporation.

The metal-containing nanoparticles may be formed by vacuum depositing a Raman active material. The Raman active material may be initially uniformly deposited on the surface of the substrate and the protuberant structures, but be intensively deposited on the upper part of the protuberant structures as the deposition progresses.

The metal may be one chosen from Au, Ag, Cu, Pt and Pd, and an alloy thereof.

A substrate with inorganic-containing particles according to an example may comprise a substrate including protuberant structures spaced-apart from each other; inorganic-containing particles formed on the surface of the substrate and the protuberant structures; and metal-containing nanoparticles formed on the inorganic-containing particles, wherein the metal-containing nanoparticles have nano-gaps with at least one of the metal-containing nanoparticles adjacent to the surface of the inorganic-containing particles and the metal-containing nanoparticles spatially adjacent within the substrate.

The inorganic-containing particles may be formed by vacuum depositing an inorganic material. The inorganic material may be initially uniformly deposited on the surface of the substrate and the protuberant structures, but be intensively deposited on the upper part of the protuberant structures as the deposition progresses.

The inorganic-containing particles may be formed in a spherical or elliptical shape.

The inorganic material may be any one chosen from an oxide, a nitride, an oxynitride of a metal chosen from Al, Ba, Be, Ca, Cr, Cu, Cd, Dy, Ga, Ge, Hf, In, Lu, Mg, Mo, Ni, Rb, Sc, Si, Sn, Ta, Te, Ti, W, Zn, Zr, and Yb, and magnesium fluoride.

The metal-containing nanoparticles may be formed by vacuum depositing a Raman active material.

The vacuum deposition may be any one chosen from chemical vapor deposition, sputtering and evaporation.

The Raman active material may be any one chosen from Au, Ag, Cu, Pt and Pd, and an alloy thereof.

The substrate may be a polymer substrate and the protuberant structures may be formed by surface-processing the polymer substrate.

The surface-processing may be performed by any one chosen from plasma etching, soft lithography, embossing, nano imprinting, photolithography, and holographic lithography.

When plasma etching is used, it is performed by using at least one chosen from argon, oxygen, hydrogen, helium, and nitrogen gas.

The upper part of the protuberant structures may have a larger curvature than the lower part.

A method for manufacturing a substrate with inorganic-containing particles according to an example may comprise: forming protuberant structures spaced-apart from each other by processing a substrate; forming metal-containing nanoparticles on the surface of the substrate and the protuberant structures; and forming metal-containing nanoparticles on the inorganic-containing particles, wherein the metal-containing nanoparticles have nano-gaps with at least one of the metal-containing nanoparticles adjacent to the surface of the inorganic-containing particles and the metal-containing nanoparticles spatially adjacent within the substrate.

The inorganic-containing particles may be formed by vacuum depositing an inorganic material and the inorganic material may be initially uniformly deposited on the surface of the substrate and the protuberant structures, but be intensively deposited on the upper part of the protuberant structures as the deposition progresses.

The inorganic-containing particles may be formed in a spherical or elliptical shape.

The inorganic material may be any one chosen from an oxide, a nitride, an oxynitride of a metal chosen from Al, Ba, Be, Ca, Cr, Cu, Cd, Dy, Ga, Ge, Hf, In, Lu, Mg, Mo, Ni, Rb, Sc, Si, Sn, Ta, Te, Ti, W, Zn, Zr, and Yb, and magnesium fluoride.

The metal-containing nanoparticles may be formed by vacuum depositing a Raman active material.

The vacuum deposition may be performed by any one chosen from chemical vapor deposition, sputtering and evaporation.

The Raman active material may be one chosen from Au, Ag, Cu, Pt and Pd, and an alloy thereof.

The substrate may be a polymer substrate and the protuberant structures may be formed by surface-processing the polymer substrate.

The surface-processing may be performed by any one chosen from plasma etching, soft lithography, embossing, nano imprinting, photolithography, and holographic lithography.

When plasma etching is used, it is performed by using at least one chosen from argon, oxygen, hydrogen, helium, and nitrogen gas.

The upper part of the protuberant structures may have a larger curvature than the lower part.

A substrate with inorganic-metal structures according to an example may comprise: a substrate including protuberant structures having upper protruded curved surfaces formed to be spaced-apart from each other; metal-containing nanoparticles formed on the protuberant structures; metal-containing thin layer formed on the surface of the substrate; and an inorganic material-containing thin layer formed between the metal-containing nanoparticles and the protuberant structures and between the metal-containing thin layer and the substrate surface, wherein the metal-containing nanoparticles and the metal-containing thin layer are formed at the same time by vacuum depositing a Raman active material and the Raman active material is initially uniformly deposited on the metal thin film and the protuberant structures but is intensively deposited on the upper part of the protuberant structures as the deposition progresses.

The substrate with inorganic-metal structures may further comprise at least one inorganic material-containing thin layer which is formed of a different material from that used for the inorganic material-containing thin layer formed between the inorganic material-containing thin layer and the substrate.

The inorganic material may be any one chosen from an oxide, a nitride, an oxynitride of a metal chosen from Al, Ba, Be, Ca, Cr, Cu, Cd, Dy, Ga, Ge, Hf, In, Lu, Mg, Mo, Ni, Rb, Sc, Si, Sn, Ta, Te, Ti, W, Zn, Zr, and Yb, and magnesium fluoride.

The inorganic material-containing thin layer may be formed by using any one chosen from chemical vapor deposition, sputtering and evaporation.

The substrate may be a polymer substrate and the protuberant structures may be formed by surface-processing the polymer substrate.

The surface-processing may be performed by any one chosen from plasma etching, soft lithography, embossing, nano imprinting, photolithography, and holographic lithography.

When plasma etching is used, it is performed by using at least one chosen from argon, oxygen, hydrogen, helium, and nitrogen gas.

The Raman active material may be one chosen from Au, Ag, Cu, Pt and Pd, and an alloy thereof.

The vacuum deposition may be performed by any one chosen from chemical vapor deposition, sputtering and evaporation.

Distance between the protuberant structures and the size of the metal-containing nanoparticles may be controlled so that the distance between the metal-containing nanoparticles is controlled.

The may be formed of any one chosen from acrylic polymers, polyethersulfones (PES), polycycloolefins (PCO), polyurethanes and polycarbonates (PC).

A method for manufacturing a substrate with inorganic-metal structures according to an example may comprise: forming protuberant structures having upper protruded curved surfaces to be spaced-apart from each other by surface-processing a substrate; forming an inorganic material-containing thin layer on the surface of the substrate and the protuberant structures; and forming metal-containing nanoparticles on the upper protuberant structures and a metal-containing thin layer on the substrate surface at the same time by vacuum depositing a Raman active material until nano-gaps are formed between adjacent metal-containing nanoparticles, wherein the Raman active material may be initially uniformly deposited on the metal thin film and the protuberant structures, but be intensively deposited on the upper part of the protuberant structures as the deposition progresses.

The method for manufacturing a substrate with inorganic-metal structures may further comprise forming at least one inorganic material-containing thin layer, which is formed of a different material from that used for the inorganic material-containing thin layer, before forming the inorganic material-containing thin layer.

The inorganic material may be any one chosen from an oxide, a nitride, an oxynitride of a metal chosen from Al, Ba, Be, Ca, Cr, Cu, Cd, Dy, Ga, Ge, Hf, In, Lu, Mg, Mo, Ni, Rb, Sc, Si, Sn, Ta, Te, Ti, W, Zn, Zr, and Yb, and magnesium fluoride.

The inorganic material-containing thin layer may be formed by using any one chosen from chemical vapor deposition, sputtering and evaporation.

The substrate may be a polymer substrate and the surface-processing may be performed by any one chosen from plasma etching, soft lithography, embossing, nano imprinting, photolithography, and holographic lithography.

When plasma etching is used, it is performed by using at least one chosen from argon, oxygen, hydrogen, helium, and nitrogen gas.

The Raman active material may be one chosen from Au, Ag, Cu, Pt and Pd, and an alloy thereof.

The vacuum deposition may be performed by any one chosen from chemical vapor deposition, sputtering and evaporation.

Distance between the protuberant structures and the size of the metal-containing nanoparticles may be controlled so that the nano-gap is controlled.

An inorganic material-grown substrate according to an example may comprise a substrate including protuberant structures spaced-apart from each other; an inorganic material-containing bar grown at the point where the protuberant structures are formed; metal-containing nanoparticles formed on the inorganic material-containing bar; and nano-gaps formed between the metal-containing nanoparticles.

The inorganic material-grown substrate may further comprise a first inorganic material-containing layer on the surface of the substrate. The first inorganic material-containing layer and the inorganic material-containing bar may be formed at the same time by vacuum depositing an inorganic material. The inorganic material may be initially uniformly deposited on the surface of the substrate and the protuberant structures, but be intensively deposited on the upper part of the protuberant structures as the deposition progresses.

The inorganic material-grown substrate may further comprise a second inorganic material-containing layer between the first inorganic material-containing layer and the protuberant structures.

At least one of the distance between the protuberant structures, the diameter of inorganic material-containing bar, and the size of the metal-containing nanoparticles may be controlled so that the nano-gap is controlled.

The inorganic material may be any one chosen from an oxide, a nitride, an oxynitride of a metal chosen from Al, Ba, Be, Ca, Cr, Cu, Cd, Dy, Ga, Ge, Hf, In, Lu, Mg, Mo, Ni, Rb, Sc, Si, Sn, Ta, Te, Ti, W, Zn, Zr, and Yb, and magnesium fluoride.

The vacuum deposition may be any one chosen from chemical vapor deposition, sputtering and evaporation.

The substrate may be a polymer substrate and the protuberant structures may be formed by surface-processing the polymer substrate.

The surface-processing may be performed by any one chosen from plasma etching, soft lithography, embossing, nano imprinting, photolithography, and holographic lithography.

When plasma etching is used, it is performed by using at least one chosen from argon, oxygen, hydrogen, helium, and nitrogen gas.

The metal-containing nanoparticles may be formed by vacuum depositing a Raman active material and the Raman active material may be initially uniformly deposited on the first inorganic material-containing layer and the inorganic material-containing bar, but be intensively deposited on the upper part of the inorganic material-containing bar as the deposition progresses.

The metal of the metal-containing nanoparticles may be any one chosen from Au, Ag, Cu, Pt and Pd, and an alloy thereof.

A method for manufacturing an inorganic material-grown substrate according to an example may comprise forming protuberant structures spaced-apart from each other by processing a substrate; growing an inorganic material-containing bar at the point where the protuberant structure is formed; and forming a metal-containing nanoparticle on the inorganic material-containing bar, wherein a nano-gap is formed between the metal-containing nanoparticles.

The first inorganic material layer may be formed at the same time when the inorganic material-containing bar is grown. The first inorganic material layer and the inorganic material-containing bar may be formed by a vacuum depositing an inorganic material. The inorganic material may be initially uniformly deposited on the surface of the substrate and the protuberant structures, but be intensively deposited on the upper part of the protuberant structures as the deposition progresses.

The method for manufacturing an inorganic material-grown substrate may further comprise a second inorganic material-containing layer before vacuum depositing the inorganic material.

At least one of the distance between the protuberant structures, the diameter of inorganic material-containing bar, and the size of the metal-containing nanoparticles may be controlled so that the nano-gap is controlled.

The vacuum deposition may be performed by any one chosen from sputtering, evaporation and chemical vapor deposition.

The substrate may be a polymer substrate and the protuberant structures may be formed by surface-processing the polymer substrate.

The surface-processing may be performed by any one chosen from plasma etching, soft lithography, embossing, nano imprinting, photolithography, and holographic lithography.

When plasma etching is used, it is performed by using at least one chosen from argon, oxygen, hydrogen, helium, and nitrogen gas.

The metal-containing nanoparticles may be formed by vacuum depositing a Raman active material and the Raman active material may be initially uniformly deposited on the first inorganic material-containing layer and the inorganic material-containing bar, but be intensively deposited on the upper part of the inorganic material-containing bar as the deposition progresses.

A method for manufacturing a nano-gap controlled substrate according to an example may comprise forming protuberant structures spaced-apart from each other on the surface of a stretchable substrate by processing the stretchable substrate; stretching the substrate; forming metal-containing nanoparticles on the protuberant structures; and forming nano-gaps between the metal-containing nanoparticles by restoring the substrate.

The method for manufacturing a nano-gap controlled substrate may further comprise forming a metal-containing thin layer on the surface of the substrate.

The metal-containing thin layer and the metal-containing nanoparticles may be formed at the same time by vacuum depositing a Raman active material.

The Raman active material may be initially uniformly deposited on the surface of the substrate and the protuberant structures, but be intensively deposited on the upper part of the protuberant structures as the deposition progresses.

The substrate may be a polymer substrate.

The upper part of the protuberant structures may have a larger curvature than the lower part.

The protuberant structures may be formed by any one chosen from plasma etching, soft lithography, embossing, nano imprinting, photolithography, and holographic lithography.

The plasma etching may be performed by using at least one chosen from argon, oxygen, hydrogen, and helium and nitrogen gas.

The metal-containing nanoparticles may be formed by vacuum depositing a Raman active material.

The vacuum deposition may be performed by any one chosen from sputtering, evaporation and chemical vapor deposition.

An analysis method using a nano-gap controlled substrate according to an example may comprise forming protuberant structures spaced-apart from each other on the surface of a stretchable substrate by processing the stretchable substrate; stretching the substrate; forming metal-containing nanoparticles on the protuberant structures; dropping an analyte on the substrate; and capturing the analyte in the nano-gaps formed between the metal-containing nanoparticles by restoring the substrate.

The nano-gap may be formed corresponding to the size of the analyte.

A nano-gap controlled substrate according to an example may comprise a stretchable substrate; protuberant structures formed to be spaced-apart on the surface on the substrate by processing the substrate; metal-containing nanoparticles formed on the protuberant structures; and nano-gaps formed between the metal-containing nanoparticles and being controllable by stretching the substrate.

The nano-gap controlled substrate may further comprise a metal-containing thin layer on the surface of the substrate.

The metal-containing thin layer and the metal-containing nanoparticles may be formed at the same time by vacuum depositing a Raman active material.

The Raman active material may be initially uniformly deposited on the surface of the substrate and the protuberant structures, but be intensively deposited on the upper part of the protuberant structures as the deposition progresses.

The substrate may be a polymer substrate.

The upper part of the protuberant structures may have a larger curvature than the lower part.

The protuberant structures may be formed by any one chosen from plasma etching, soft lithography, embossing, nano imprinting, photolithography, and holographic lithography.

The plasma etching may be performed by using at least one chosen from argon, oxygen, hydrogen, and helium and nitrogen gas.

The metal-containing nanoparticles may be formed in a spherical or elliptical shape.

The metal-containing nanoparticles may be formed by vacuum depositing a Raman active material.

The vacuum deposition may be any one chosen from chemical vapor deposition, sputtering and evaporation.

The Raman active material may be any one chosen from Au, Ag, Cu, Pt and Pd, and an alloy thereof.

A Raman spectroscopic device according to an example may comprise a light source; the substrate for surface-enhanced Raman spectroscopy described above; and a detector configured to detect Raman spectrum.

The present disclosure provides a substrate with multiple nano-gaps which can have high absorption and is capable of using light sources in a wide range and a manufacturing method therefor.

The present disclosure also provides a substrate with multiple nano-gaps with multiple nano-gaps that can achieve amplification of Raman signal by forming multiple nano-gaps, and a manufacturing method therefor.

The present disclosure also provides a substrate having thermal stability by being formed with inorganic-containing particles and amplifying the Raman signals only by multiple nano-gaps with minimizing noise about the substrate structure.

The present disclosure also provides a substrate with inorganic-metal structures which controls nano-gaps easily and has thermal stability and adhesion by introducing an inorganic material-containing thin layer.

The present disclosure also provides an inorganic material-grown substrate having thermal stability which controls nano-gaps easily, and a manufacturing method therefor. The inorganic material-grown substrate can minimize noise about the substrate structure when Raman spectrum is measured.

The present disclosure also provides a nano-gap controlled substrate and a manufacturing method therefor in which the nano-gap is controlled without external force by using the stretching of the substrate during the manufacturing process.

Other features and aspects will be apparent from the following detailed description, the drawings, and the claims.

BRIEF DESCRIPTION OF THE DRAWINGS

FIG. 2 is a diagram of another example of a conventional substrate with multiple nano-gaps.

FIG. 33 illustrates diagrams of metal-containing nanoparticles having different shapes according to an example.

FIG. 34 illustrates SEM images of protuberant structures according to an example.

FIG. 35 illustrates SEM images of an inorganic material-containing bar according to an example.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

Figure 1:
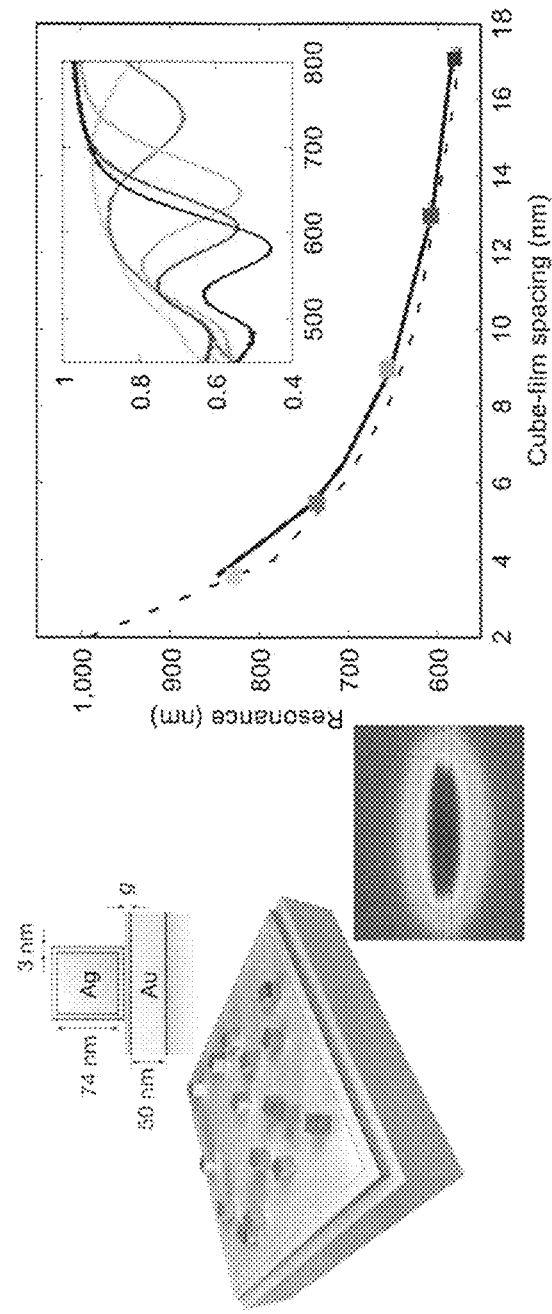
FIG. 1 is a diagram of an example of a conventional substrate with multiple nano-gaps.
Figure 3:
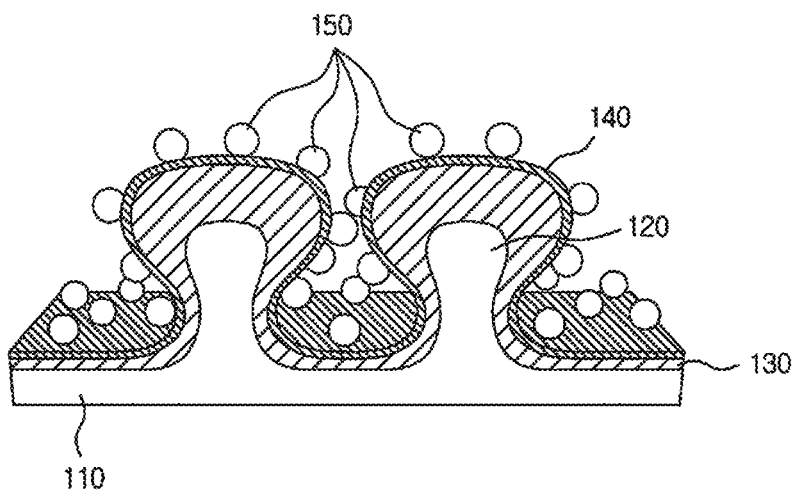
FIG. 3 is a diagram illustrating a substrate with multiple nano-gaps according to an example.

FIG. 3 is a diagram illustrating a substrate with multiple nano-gaps according to an example.

Referring to FIG. 3, a substrate with multiple nano-gaps according to an example may comprise a substrate 110, protuberant structures 120, a metal-containing thin layer 130, an insulation layer 140 and metal-containing nanoparticles 150.

The substrate 110 may be any material that can be processed in a specific pattern. The substrate 110 may be a polymer substrate, particularly polydimethylsiloxane (PDMS).

The protuberant structures 120 may be formed by processing the substrate 110 and be the same material used for the substrate 110.

A method for processing the protuberant structures 120 may be any one chosen from plasma etching, soft lithography, embossing, nano imprinting, photolithography, and holographic lithography, but it is not limited thereto.

When plasma etching is used for processing the protuberant structures 120, it is performed by using at least one chosen from argon, oxygen, hydrogen, helium, and nitrogen gas.

The metal-containing thin layer 130 is formed on the surface of the substrate 110 and the protuberant structures 120.

The metal-containing thin layer 130 is formed by vacuum depositing a Raman active material. The Raman active material is initially uniformly deposited on the surface of the substrate and the protuberant structures, but is intensively deposited on the upper part of the protuberant structures as the deposition progresses.

The upper part of the protuberant structures 120 may have a larger curvature than the lower part. When the upper part of the protuberant structures 120 is formed to have a larger curvature than the lower part, the metal-containing thin layer 130 may be adhered better to the upper part of the protuberant structures 120 than to the surface of the substrate 110. As shown in FIG. 3, the protuberant structures 120 and the metal-containing thin layer 130 may be formed in a tree shape and the metal-containing thin layer 130 may be formed larger at the upper part of the protuberant structures 120. This is because the high curvature on the protuberant structures 120 leads to the accumulation of negative charges on the upper part and induces the deposition of positively charged metal ions.

The intensively deposited metal-containing thin layer 130 is due to the shadow effect of particles already deposited on the upper part of the protuberant structures 120 as the deposition progresses. Accordingly, the distribution of the metal-containing thin layer 130 and the size of the metal-containing thin layer 130 on the protuberant structures 120 can be controlled.

The vacuum deposition may be performed by one chosen from sputtering, evaporation and chemical vapor deposition, but it is not limited thereto.

The Raman active material may be any one chosen from Au, Ag, Cu, Pt, Pd and an alloy thereof.

The insulation layer 140 may be formed on the metal-containing thin layer 130, more particularly conformally on the metal-containing thin layer 130.

The insulation layer 140 may be formed by any one of vacuum deposition and solution process. The insulation layer 140 may also be formed by other methods.

The vacuum deposition may be performed by using one chosen from atomic layer deposition, chemical vapor deposition, sputtering and thermal evaporation, but it is not limited thereto.

The solution process may be performed by any one chosen from spin coating, dip coating and dropping process, but it is not limited thereto.

The atomic layer deposition (ALD) is used as an example of the vacuum deposition in the present disclosure. The atomic layer deposition is advantageous for forming specific nano-gaps because it is a technique for depositing a conformal film even in a three-dimensional structure.

The insulation layer 140 may be formed of any one chosen from alumina, metal oxide, metal sulfide, metal halide, silica, zirconium oxide and iron oxide, but it is not limited thereto. Alumina ($Al_2O_3$) is used as an example of a material of the insulation layer 140 in the present disclosure.

A thickness of the insulation layer 140 may be from 0.5 nm to 100 nm. When the thickness of the insulation layer 140 is 100 nm or higher, no electromagnetic coupling occurs between the metals on both sides of the insulation layer 140, so localized surface plasmon resonance does not occur.

The thickness of the insulation layer 140 is adjustable so that the LSPR (localized surface plasmon resonance) is optimal for a particular wavelength.

The optimal LSPR means that it is optimized for the Raman wavelength of a target molecule to be analyzed and the wavelength of a light source. In order to maximize the enhancement of the Raman signal, it is desirable to position the LSPR wavelength between the wavelength of a light source and the Raman wavelength of a target molecule to be analyzed.

The metal-containing nanoparticles 150 may be formed on the insulation layer to be spaced apart.

The metal-containing nanoparticles 150 may be formed by vacuum depositing a Raman active material.

The vacuum deposition may be performed by any one chosen from sputtering, evaporation and chemical vapor deposition, but it is not limited thereto.

The Raman active material may be any one chosen from Au, Ag, Cu, Pt, Pd and an alloy thereof.

The metal-containing nanoparticles 150 may be controlled in size by controlling the deposition time and when the size of the metal-containing nanoparticles 150 is controlled, the distance between the metal-containing nanoparticles 150 is controlled.

By adjusting the size of the metal-containing nanoparticles 150, the LSPR can be optimized for a particular wavelength.

As described above, the LSPR can be adjusted to be optimal by controlling at least one of the thickness of the insulation layer 140 and the size of the metal-containing nanoparticles 150.

Figure 4:
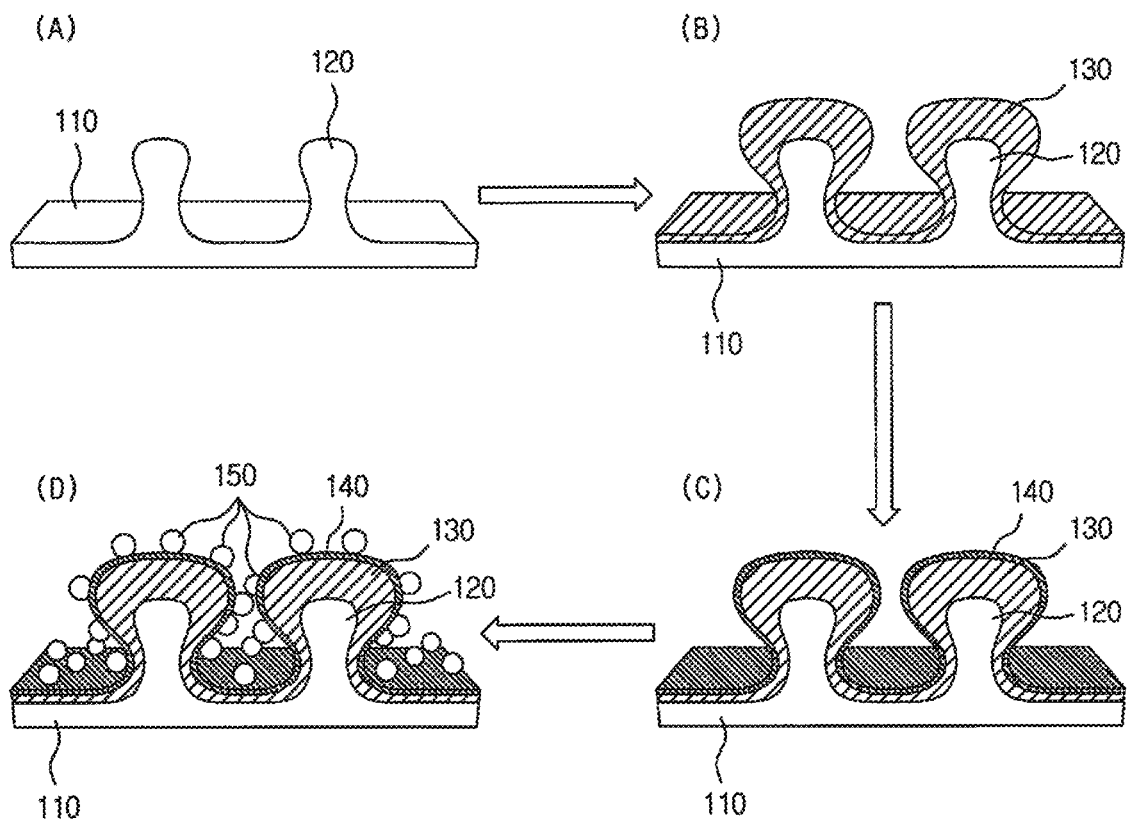
FIG. 4 is a diagram illustrating a process for manufacturing a substrate with multiple nano-gaps according to another example.

FIG. 4 is a diagram illustrating a process for manufacturing a substrate with multiple nano-gaps according to another example.

Referring to FIG. 4(A), the substrate 110 may be a PDMS substrate and the protuberant structures 120 are formed by plasma etching the substrate 110.

Referring to FIG. 4(B), the metal-containing thin layer 130 is formed by vacuum depositing a Raman active material of Ag on the substrate 110 where the protuberant structures 120 is formed. The metal-containing thin layer 130 may be formed on the surface of the substrate 110 and the protuberant structures 120. The metal-containing thin layer 130 may be formed to be thicker on the upper part of the protuberant structures 120.

Referring to 4(C), an insulation layer is formed by atomic layer deposition of alumina ($Al_2O_3$) on the metal-containing thin layer 130.

Conditions used to perform the atomic layer deposition are as follows.

A base material of the substrate 110: PDMS substrate (thickness: about 1 mm)
Initial vacuum degree: $3 \times 10^{-2}$ torr
Reaction gas: TMA [Trimethylaluminium], $H_2O$
Deposition temperature: 100° C.
Purging gas flow rate: Ar 100 sccm
A thickness of the insulation layer 140 may be controlled to be from 1 nm to 15 nm.

Referring to FIG. 4(D), the metal-containing nanoparticles 150 are formed by vacuum depositing a Raman active material of Ag on the insulation layer 140 and multiple nano-gaps are formed between the metal-containing nanoparticles 150 and between the metal-containing nanoparticles 150 and the metal-containing thin layer 130.

As described above, a desired size of the nano-gaps may be obtained by adjusting by controlling at least one of the thickness of the insulation layer 140 and the size of the metal-containing nanoparticles 150 during the manufacturing process.

Figure 5:
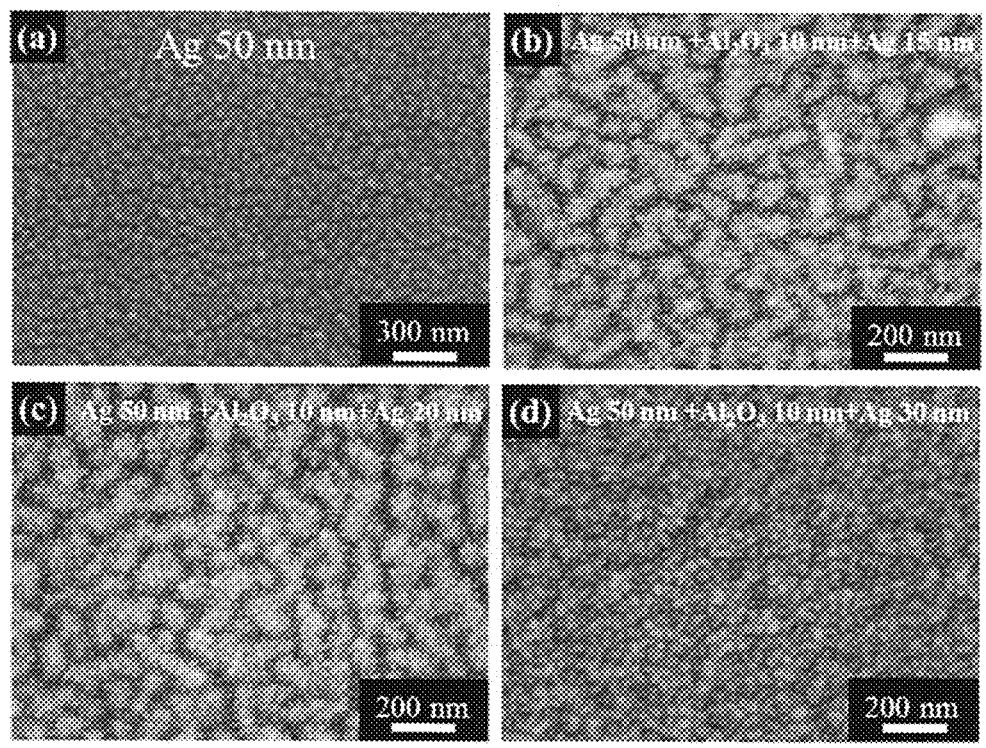
FIG. 5 illustrates SEM images of a substrate with multiple nano-gaps according to an example.

FIG. 5 illustrates SEM images of a substrate with multiple nano-gaps according to an example.

Conditions used to form the protuberant structures 120 are as follows.

A base material of the substrate 110: PDMS substrate
Initial vacuum degree: $3 \times 10^{-2}$ torr
Reactive ion etching conditions.
Vacuum for pretreatment process: $8 \times 10^{-2}$ torr
Operation gas: $CF_4$ 5 sccm
RF plasma power for pretreatment: 100 W
Pretreatment time: 75 sec In this example, a PDMS (polydimethylsiloxane) substrate was used and reactive ion etching (RIE) was performed using $CF_4$ gas and 100 W of RF plasma power for pretreatment for 75 seconds to provide the protuberant structures 120 with size of tens of nanometers. The thermal evaporation was then performed with a Raman active material of Ag to provide 50 nm of thickness of the metal-containing thin layer 130. Referring to FIG. 5(a), it is noted that 30 nm to 40 nm of nano-gap is formed between the metal-containing thin layers 130 on the protuberant structures 120. The atomic layer deposition was performed with alumina ($Al_2O_3$) to provide uniform 10 nm of thickness of the insulation layer 140. The thermal evaporation was then performed with Ag to provide 15 nm, 20 nm, and 30 nm of diameter of the metal-containing nanoparticles 150 as shown in FIGS. 5(b), 5(c) and 5(d), respectively.

As shown in SEM images, it is noted that the metal-containing nanoparticles 150 are formed on the side surfaces of the protuberant structures 120 as well as on the top surface of the protuberant structures 120. When the size of the metal-containing nanoparticles 150 reaches 30 nm, as shown in FIG. 5(d), the metal-containing nanoparticles 150 are connected to each other and the density of the nano-gaps between the protuberant structures 120 is reduced.

A feature of this disclosure different from the prior art is the deposition of the metal-containing thin layer 130 and the insulation layer 140 on the non-planar three-dimensional protuberant structures 120 in 3-dimensional structure, instead of planar one. The metal-containing nanoparticles 150 are then evenly distributed on the 3-dimensional structure. From the viewpoint of surface-enhanced Raman spectroscopy, the nano-gap, that is, the density of hot spots, is greatly increased compared with the two-dimensional structure so that effect of enhancing the Raman signal can be greatly improved.

Figure 6:
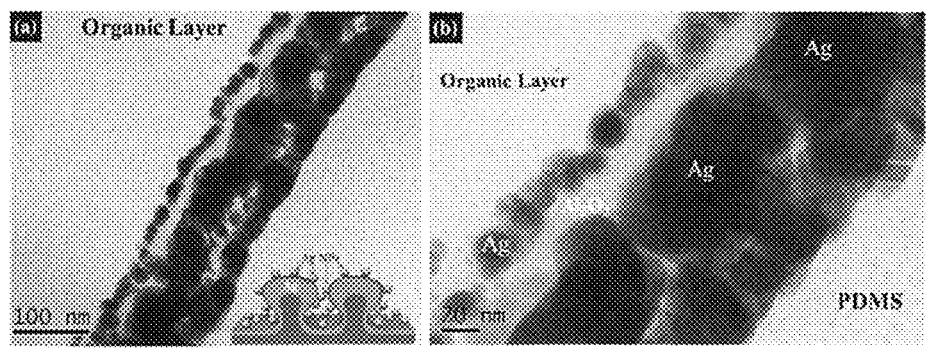
FIG. 6 illustrates TEM images of a substrate with multiple nano-gaps according to an example.

FIG. 6 illustrates TEM image of a substrate with multiple nano-gaps according to an example.

Referring to FIG. 6, shapes of the metal-containing thin layer 130, the insulation layer 140 and the metal-containing nanoparticles 150 in 3-dimension can be obtained. The protuberant structures 120 formed on the PDMS substrate 110 are spaced apart and the metal-containing thin layer 130 is formed on the protuberant structures 120. The insulation layer 140 evenly covers the metal-containing thin layer 130 through the atomic layer deposition and the metal-containing nanoparticles 150 are uniformly distributed on the insulation layer 140. The metal-containing nanoparticles 150 have different heights according to the 3-dimensional protuberant structures 120.

Optical properties of the substrate with multiple nano-gaps are determined.

Figure 7:
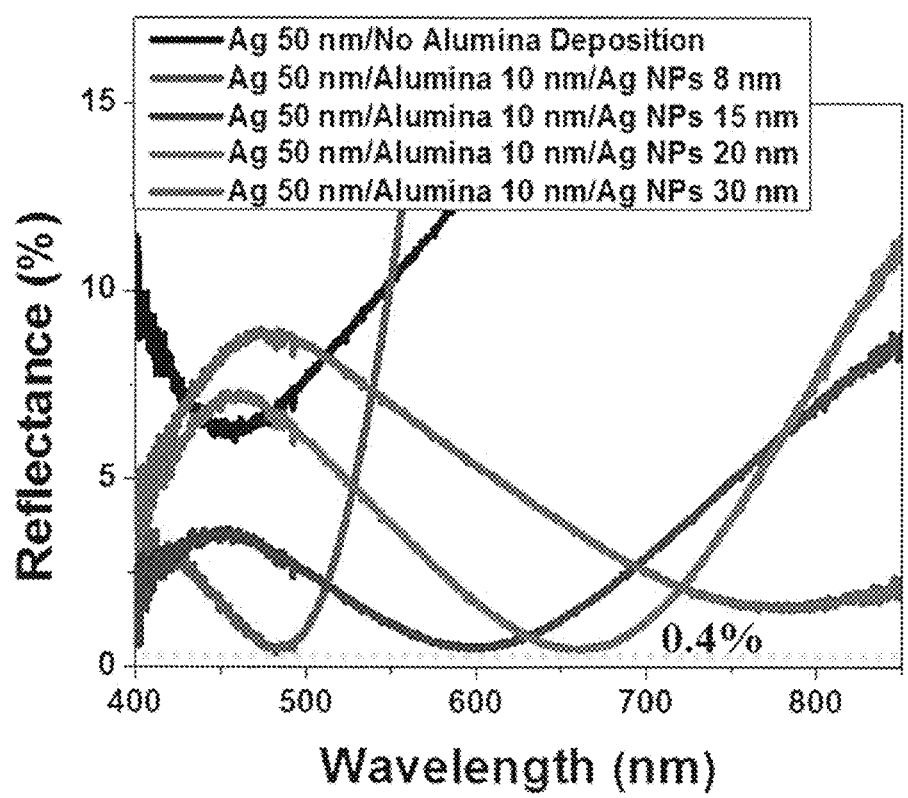
FIG. 7 is a graph illustrating reflectance of substrates comprising multiple nano-gaps according to examples.

FIG. 7 is a graph illustrating reflectances of substrates comprising multiple nano-gaps according to examples. Here, the metal-containing nanoparticles 150 are represented by NPs.

Referring to FIG. 7, a sample of the metal-containing thin layer 130 formed by vacuum depositing a Raman active material of Ag in 50 nm on the protuberant structures 120 has 7% of reflectance dip at 456 nm (black solid line). It is noted that light at a wavelength of 456 nm is absorbed due to the protuberant structures 120, on which the metal-containing thin layer 130 is deposited. Such plasmonic characteristics do not appear when the metal-containing thin layer 130 is deposited on a flat surface. When Ag is deposited on the flat surface, reflection is very large like a mirror. This technical feature of the disclosure is distinguished from the conventional ones.

A substrate with multiple nano-gaps of this disclosure also has plasmonic characteristics. When reflectance of the substrate with multiple nano-gaps, in which the insulation layer 140 is formed by depositing $Al_2O_3$ in 10 nm and the metal-containing nanoparticles 150 is formed by depositing Ag in a diameter of 8 nm on the insulation layer 140, is measured, reflection dip is shifted to 484 nm and reflectance at this point is found to be 0.4%. (red solid line). It means that the substrate with multiple nano-gaps including the protuberant structures 120, the metal-containing thin layer 130, the insulation layer 140 and the metal-containing nanoparticles 150 more efficiently absorbs light of a specific wavelength, compared the substrate including only the metal-containing thin layer 130 formed on the protuberant structures 120. The closer the reflectance is to zero, the more effective the plasmonic light absorber is.

Referring to blue solid line and purple solid line, it can be seen that even if the size of the metal-containing nanoparticles 150 is increased, the absorption efficiency remains the same and the reflection dip, that is, the peak wavelength of the LSPR shifts to a longer wavelength.

Referring to green solid line, when the size of the metal-containing nanoparticles 150 is as large as 30 nm or more, the absorption efficiency is deteriorated due to the reflection by the metal-containing nanoparticles 150 as in the prior art.

Figure 8:
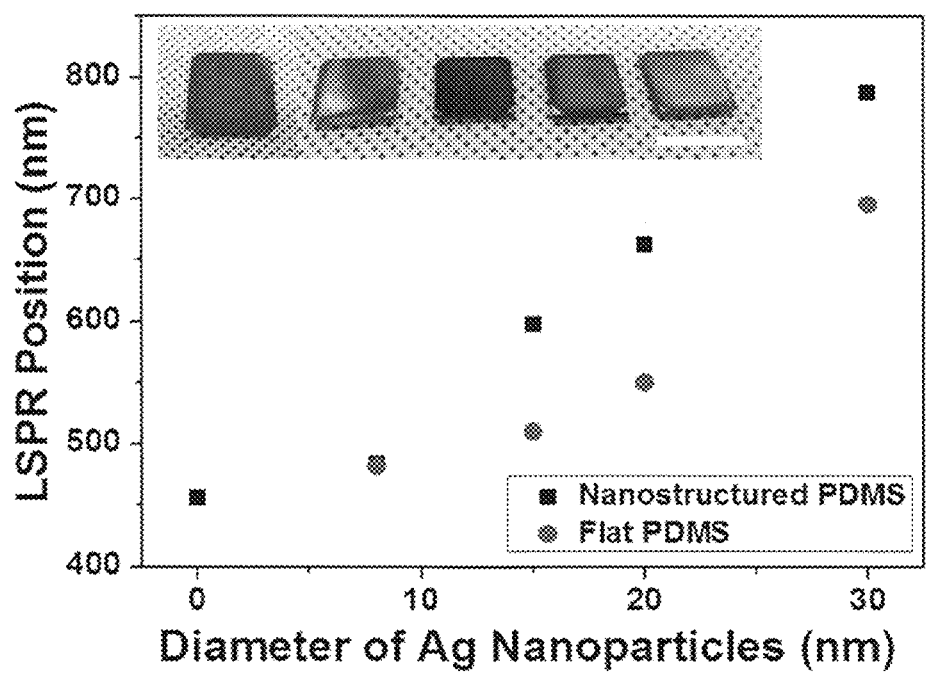
FIG. 8 is a graph illustrating LSPR positions of substrates comprising multiple nano-gaps according to examples.

FIG. 8 is a graph illustrating LSPR positions of substrates comprising multiple nano-gaps according to examples.

Referring to FIG. 8, the substrate with multiple nano-gaps has the advantage that the adjustable range of LSPR is from 456 nm to 785 nm, which can be adjusted from visible to near infrared.

The wide adjustable range of the LSPR is significant in that it can freely use the wavelength of a light source (laser) to be used in surface-enhanced Raman spectroscopy (SERS) analysis. In surface-enhanced Raman spectroscopy (SERS) analysis, it is generally advantageous to align the position of the LSPR peak to the visible region, since Raman efficiency is inversely proportional to the wavelength of an excitation laser.

However, in order to utilize the substrate with multiple nano-gaps for bio-sensing, it is desirable to irradiate with a laser with a low energy of 633 nm or more. Biomaterials are destroyed when irradiated with visible light with high energy.

Therefore, since the peak position of the LSPR can be adjusted from visible to near infrared, the methodology used in this disclosure can be applied to chemicals and biosensors using surface-enhanced Raman spectroscopy (SERS) technology.

Figure 9:
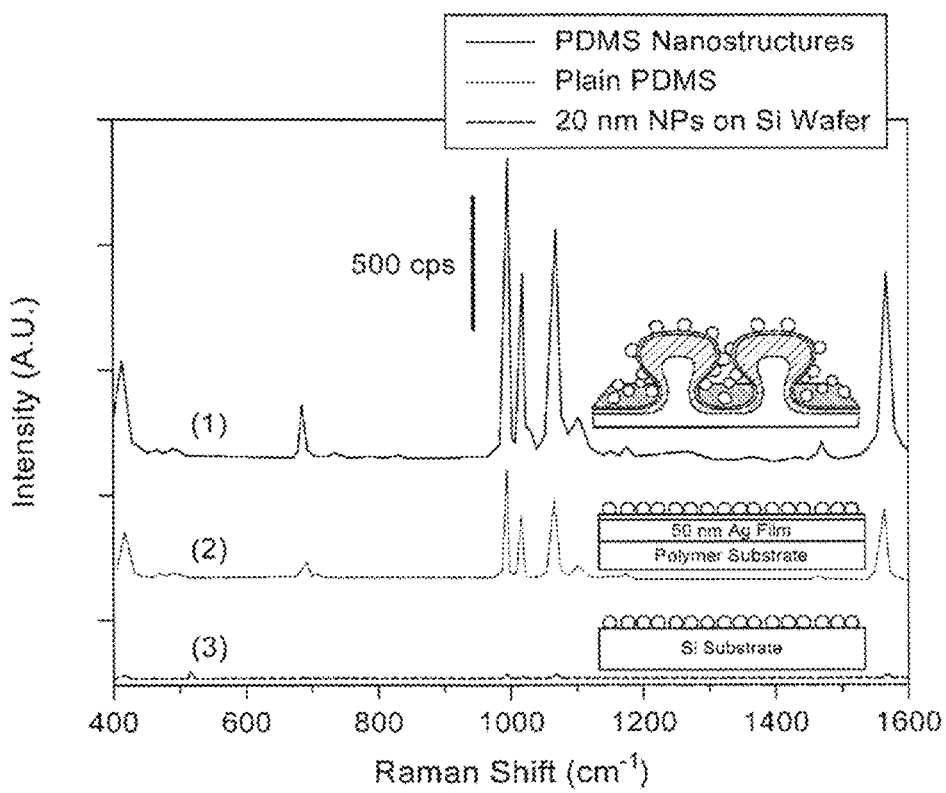
FIG. 9 is a graph illustrating Raman spectrum characteristics of a substrate with multiple nano-gaps according to an example and other substrates.

FIG. 9 is a graph illustrating Raman spectrum characteristics of a substrate with multiple nano-gaps according to an example and other substrates.

Measurement conditions are as follows.
Excitation laser wavelength: 633 nm
Objective lens: 50×
Spot size: ~2 μm
Power: 0.5 mW Referring to FIG. 9, Raman signal intensity was determined for various substrates for the SERS spectrum. FIG. 9(1) is a benzenethiol (BT) Raman signal of a substrate with multiple nano-gaps according to an example, FIG. 9(2) is a BT Raman signal of a substrate which is formed by depositing a Ag film on a flat PDMS substrate, depositing alumina as an insulation layer and then depositing Ag nanoparticles, and FIG. 9(3) is a BT Raman signal of a substrate which is formed by only depositing Ag nanoparticles on a flat Si substrate.

As shown in FIG. 9, the substrate with multiple nano-gaps has a signal enhancement of 2.7 times than the substrate (2) and 48 times the substrate (3).

It is considered that the increase of the nano-gap density of this 3-dimensional substrate with multiple nano-gaps, compared to the two-dimensionally layered substrate, is the cause of the signal enhancement. It is noted that the substrate (3) has plasmonic coupling only in plane, the substrate (2) has in plane and out-of plane, and the substrate (1) has plasmonic coupling between the metal-containing nanoparticles 150 formed between 3-dimensional protuberant structures 120 as well as in plane and out-of plane, which thus shows enhanced SERS characteristics.

Figure 10:
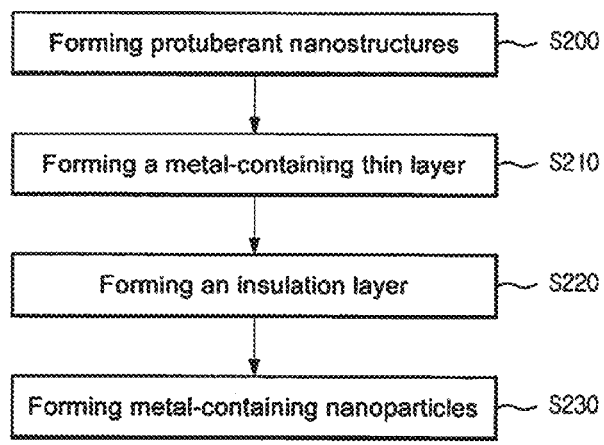
FIG. 10 is a flowchart illustrating a method for manufacturing a substrate with multiple nano-gaps according to an example.

FIG. 10 is a flowchart illustrating a method for manufacturing a substrate with multiple nano-gaps according to an example.

Referring to FIG. 10, in S200, the protuberant structures 120 is formed on the substrate 110.

The protuberant structures 120 may be formed by reactive ion etching the substrate 110.

In S210, the metal-containing thin layer 130 is formed on the surface of the substrate 110 and the protuberant structures 120. The metal-containing thin layer 130 may be formed by thermal evaporating Ag.

In S220, the insulation layer 140 is formed on the metal-containing thin layer 130. The insulation layer 140 may be formed by the atomic layer deposition, but it is not limited thereto.

In S230, the metal-containing nanoparticles 150 are formed to be spaced apart from each other on the insulation layer 140.

Figure 11:
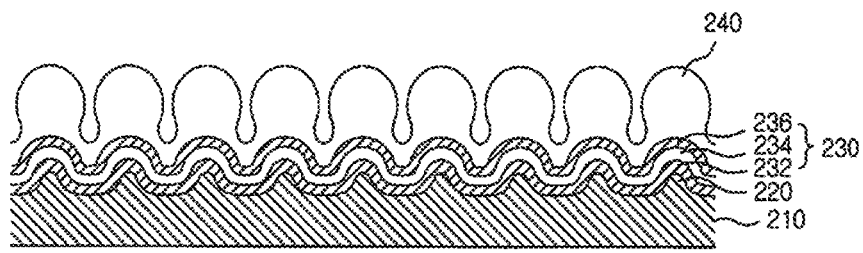
FIG. 11 is a diagram illustrating a substrate with multiple nano-gaps according to an example.

FIG. 11 is a diagram illustrating a substrate with multiple nano-gaps according to an example.

Referring to FIG. 11, a substrate with multiple nano-gaps according to an example may comprise a substrate 210, protuberant structures 220, a continuous layer 230 and metal-containing nanoparticles 240.

The substrate 210 may be a polymer substrate. The polymer substrate 210 is advantageous for forming the protuberant structures 220 in a large area even by a simple surface processing. However, any substrate can be used to have similar structure depending on processing methods.

The polymer substrate 210 may be one chosen from acrylic polymers, polyethersulfones, polycycloolefins, polyurethanes, polyethylene terephthalates and polycarbonates, but it is not limited thereto. Polyethylene terephthalate (PET) is used in this disclosure as the polymer substrate 210.

The protuberant structures 220 are formed by processing the substrate 210.

The protuberant structures 220 may be formed by surface-processing the polymer substrate 210 and the surface processing may be any one chosen from plasma etching, soft lithography, embossing, nano imprinting, photolithography, and holographic lithography, but it is not limited thereto.

When plasma etching is used, it is performed by using at least one chosen from argon, oxygen, hydrogen, helium, and nitrogen gas, but it is not limited thereto.

The protuberant structures 220 have upper protruded curved surfaces. Having upper protruded curved surface means that the upper part of the protuberant structures 220 has a larger curvature than the lower part. This structure provides a condition that the Raman active material can be intensively deposited on the upper part of the protuberant structures 220 during deposition.

The continuous layer 230 is formed on the surface of the substrate 210 and the protuberant structures 220.

The continuous layer 230 includes at least one inorganic material-containing thin layer and at least one metal-containing thin layer.

Figure 14:
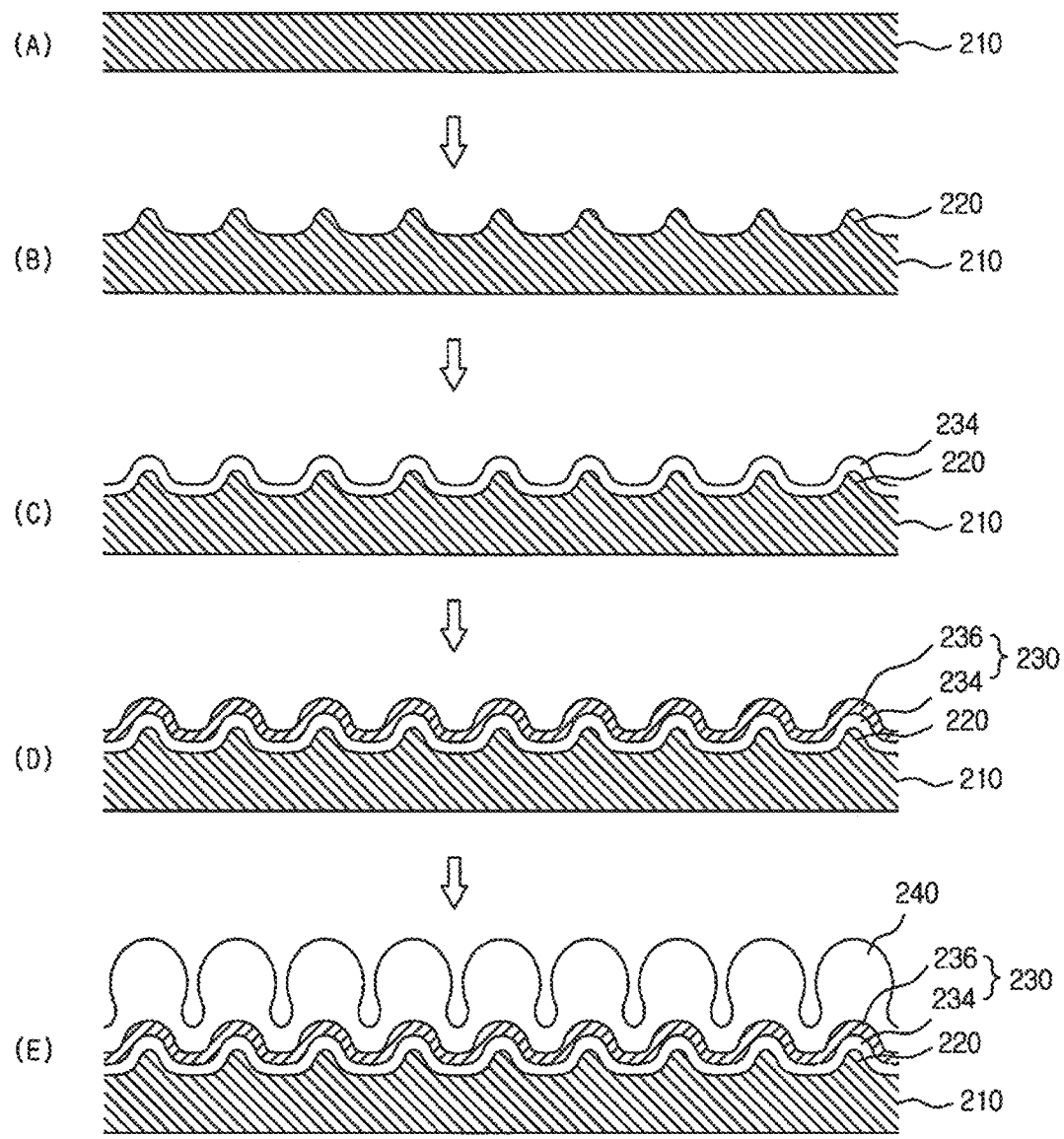
FIG. 14 is a diagram illustrating a process for manufacturing a substrate with multiple nano-gaps according to another example.

The continuous layer 230, as shown in FIG. 11, may be formed by sequentially forming an inorganic material-containing thin layer 232, a metal-containing thin layer 234 and an inorganic material-containing thin layer 236 (dielectric-metal-dielectric, DMD). The continuous layer 230, as shown in FIG. 14, may be formed by sequentially forming the metal-containing thin layer 234 and the inorganic material-containing thin layer 236 (metal-dielectric, MD), but it is not limited thereto.

An inorganic material of the inorganic material-containing thin layers 232, 236 may be any one chosen from an oxide, a nitride, an oxynitride of a metal chosen from Al, Ba, Be, Ca, Cr, Cu, Cd, Dy, Ga, Ge, Hf, In, Lu, Mg, Mo, Ni, Rb, Sc, Si, Sn, Ta, Te, Ti, W, Zn, Zr, and Yb, and magnesium fluoride, but it is not limited thereto. A semiconductor material may be also used instead of the inorganic material.

A metal of the metal-containing thin layer 234 may be one chosen from Au, Ag, Cu, Pt and Pd, and an alloy thereof.

The inorganic material-containing thin layers 232, 236 and the metal-containing thin layer 234 may be formed by any one chosen from chemical vapor deposition (CVD), sputtering and evaporation, but it is not limited thereto.

The inorganic material-containing thin layers 232, 236 may have a thickness of from 5 nm to 100 nm, but it is not limited thereto.

The inorganic material-containing thin layers 232, 236 may be formed to have from the minimum thickness of about 5 nm for forming the continuous layer to the maximum thickness of 100 nm for electron tunneling.

The metal-containing thin layer 234 may have a thickness of 5 nm to 200 nm, but it is not limited thereto.

The metal-containing thin layer 234 may be formed to have from the minimum thickness of about 5 nm for forming the continuous layer to the maximum thickness of 200 nm which can show strong Raman absorption in 400 to 600 nm of the visible region.

The continuous layer 230 may include 2 or more metal-containing thin layers and an inorganic material-containing thin layer may be formed between the metal-containing thin layers. Nano-gaps may be formed between the metal-containing thin layers separated by the inorganic material-containing thin layer.

The inorganic material-containing thin layers 232, 236 may be formed by sputtering.

The protuberant structures are formed on the substrate 210 by dry etching in a vacuum chamber and the vacuum chamber is maintained to have vacuum degree of $2\times10^{-5}$ torr using a low vacuum pump and a high vacuum pump. Ar operation gas is injected to reach an operation vacuum of $2\times10^{-3}$ torr. Power is applied to a plasma generating power source connected to a sputtering target with the inorganic material of $SiO_2$. Plasma is generated and the inorganic material is deposited on the surface of substrate 210 and protuberant structures 220 or on the already deposited metal-containing thin layer 234.

Processing conditions are as follows.
Base substrate: Polyethylene terephthalate (PET) thickness 188 mm, Transmittance. 90%
Initial vacuum degree: $2\times10^{-5}$ torr
Sputtering target for coating an inorganic material: $SiO_2$ (Size: 4 inch)
Operation gas: Ar
Operation vacuum degree: $2\times10^{-3}$ torr
RF power: 200 W The metal-containing nanoparticles 240 are formed on the surface of the substrate 210 and the protuberant structures 220 after the continuous layer 230 is formed.

The metal-containing nanoparticles 240 are formed by vacuum depositing a Raman active material and the vacuum deposition may be performed by any one chosen from chemical vapor deposition (CVD), sputtering and evaporation, but it is not limited thereto.

The Raman active material is initially uniformly deposited on the surface of the substrate 210 and the protuberant structures 220, but is intensively deposited on the upper part of the protuberant structures 220 as the deposition progresses. As the deposition progresses, because of the high curvature on the upper part of the protuberant structures 220, the accumulation of negative charges is induced at the top and the deposition of positively charged metal ions can be induced. This non-uniform deposition is due to the shadow effect of the already deposited metal-containing nanoparticles 240. That is, the amount of the Raman active material reaching the surface of the substrate 210 is significantly reduced due to the already deposited metal-containing nanoparticles 240, and the Raman active material is thus more intensively deposited on the upper part of the protuberant structures 220.

The metal may be any one chosen from Au, Ag, Cu, Pt and Pd, and an alloy thereof, but it is not limited thereto.

The metal-containing nanoparticles 240, as shown in FIG. 11, are formed intensively the upper part so that nano-gaps are formed between the metal-containing nanoparticles 240. Since the metal-containing nanoparticles 240 are also adjacent to the underlying metal-containing thin layer 234, nano-gaps may be formed therebetween.

Figure 12:
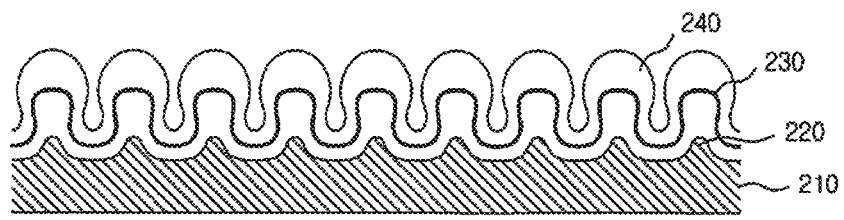
FIG. 12 is a diagram illustrating a substrate with multiple nano-gaps according to another example.

FIG. 12 is a diagram illustrating a substrate with multiple nano-gaps according to another example.

Referring to FIG. 12, a substrate with multiple nano-gaps according to another example may comprise a substrate 210, protuberant structures 220, a continuous layer 230 and metal-containing nanoparticles 240.

The process for forming the protuberant structures 220 according to another example is the same as described above. The metal-containing nanoparticles 240 are deposited then.

During the deposition of the metal-containing nanoparticles 240, the deposition of a Raman active material is stopped and the continuous layer 230 including the inorganic material-containing thin layer 232, the metal-containing thin layer 234 and the inorganic material-containing thin layer 236 is formed. After forming the continuous layer 230, the Raman active material is deposited to complete forming the metal-containing nanoparticles 240.

The continuous layer 230 according to another example may be formed separately from the metal-containing nanoparticles 240 or may be formed within the metal-containing nanoparticles 240.

Figure 13:
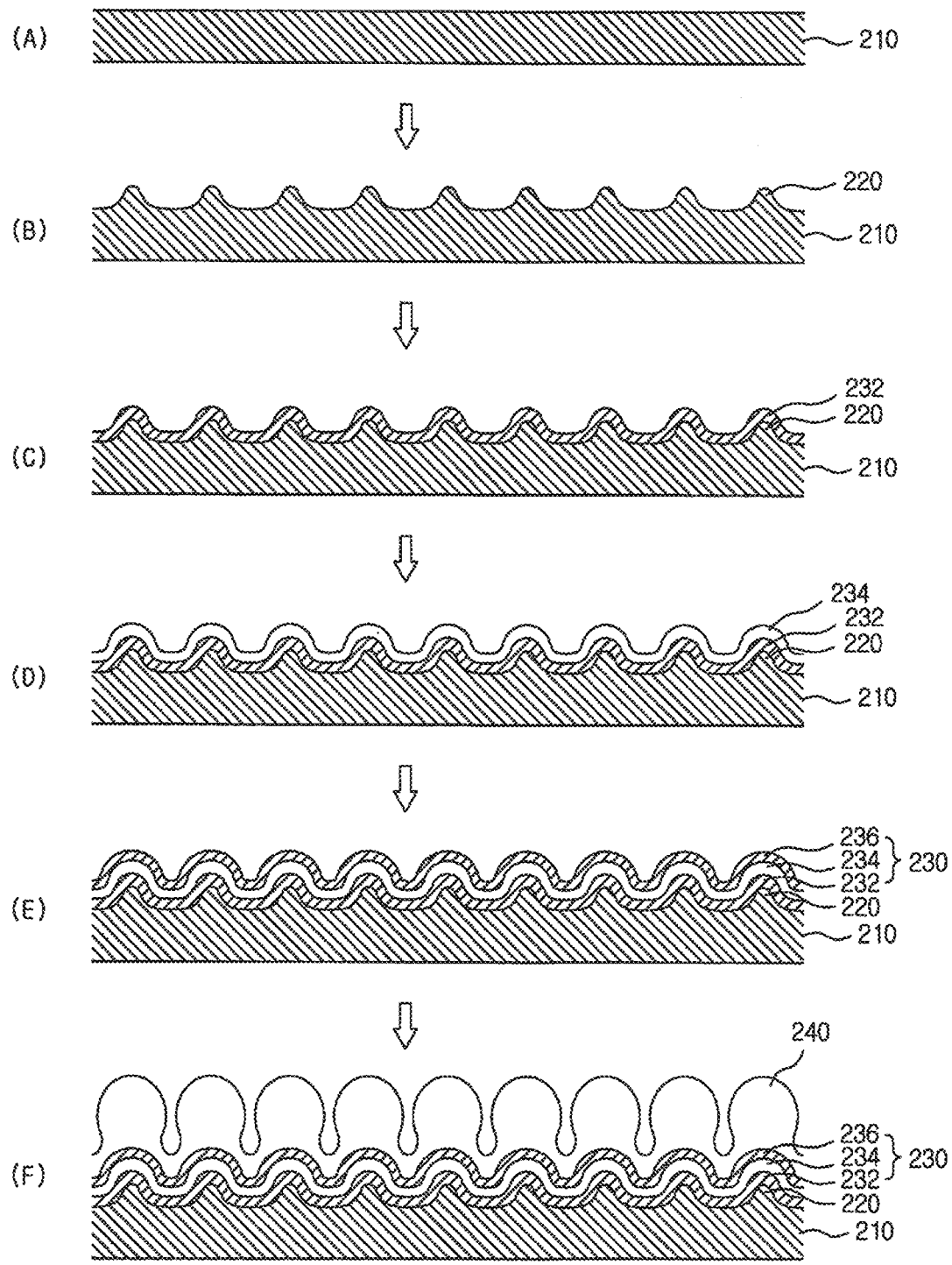
FIG. 13 is a diagram illustrating a process for manufacturing a substrate with multiple nano-gaps according to an example.

FIG. 13 is a diagram illustrating a process for manufacturing a substrate with multiple nano-gaps according to an example.

Referring to FIGS. 13(A) and 13(B), the protuberant structures 220 having upper protruded curved surfaces which are spaced-apart from each other are formed by processing the substrate 210. The protuberant structures 220 may be formed by dry etching, but it is not limited thereto.

FIGS. 13(C), 13(D) and 13(E) are diagrams illustrating a process for forming the continuous layer 230 sequentially. The continuous layer 230 may be formed by sequentially depositing the inorganic material-containing thin layer 232, the metal-containing thin layer 234 and the inorganic material-containing thin layer 236.

Referring to FIG. 13(F), the metal-containing nanoparticles 240 is formed by vacuum depositing a Raman active material on the substrate 210 on which the continuous layer 230 is formed. The Raman active material is initially uniformly deposited on the surface of the substrate 210 and protuberant structures 220, but is intensively deposited on the upper part of the protuberant structures 220 as the deposition progresses. Thus, the metal-containing nanoparticles 240, as shown in FIG. 13(F), have a spherical or elliptical shape at the top.

FIG. 14 is a diagram illustrating a process for manufacturing a substrate with multiple nano-gaps according to another example Referring to FIGS. 14(A) and 14(B), the protuberant structures 220 having upper protruded curved surfaces are formed to be spaced-apart from each other by processing the substrate 210. The protuberant structures 220 may be formed by dry etching, but it is not limited thereto.

FIGS. 14(C) and 14(D) are diagrams illustrating a process for forming the continuous layer 230 sequentially. The continuous layer 230 may be formed by sequentially depositing the metal-containing thin layer 234 and the inorganic material-containing thin layer 236.

Referring to FIG. 14(E), the metal-containing nanoparticles 240 is formed by vacuum depositing a Raman active material on the substrate 210 on which the continuous layer 230 is formed. The Raman active material is initially uniformly deposited on the surface of the substrate 210 and protuberant structures 220, but is intensively deposited on the upper part of the protuberant structures 220 as the deposition progresses. Thus, the metal-containing nanoparticles 240, as shown in FIG. 14(E), have a spherical or elliptical shape at the top.

Figure 15:
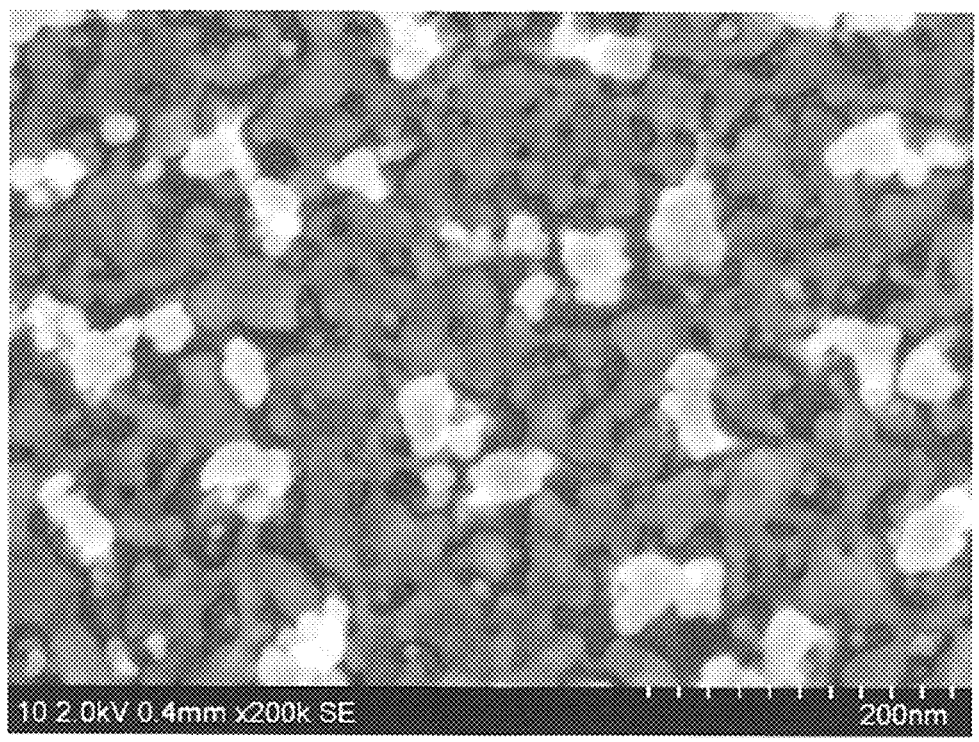
FIG. 15 is a SEM image of the surface of a continuous layer formed by sequentially forming a metal-containing thin layer, an inorganic material-containing thin layer and a metal-containing thin layer according to an example.

FIG. 15 is a SEM image of the surface of the continuous layer formed by sequentially forming the metal-containing thin layer 232, the inorganic material-containing thin layer 234 and the metal-containing thin layer 236 according to an example.

The continuous layer 230 of FIG. 15 is deposited on the protuberant structures 220 which are etched with RF power of 200 W for 2 min. The continuous layer 230 is formed by sequentially forming an inorganic material-containing thin layer ($SiO_2$ 5 nm), a metal-containing thin layer (Ag 10 nm) and an inorganic material-containing thin layer ($SiO_2$ 10 nm).

Figure 16:
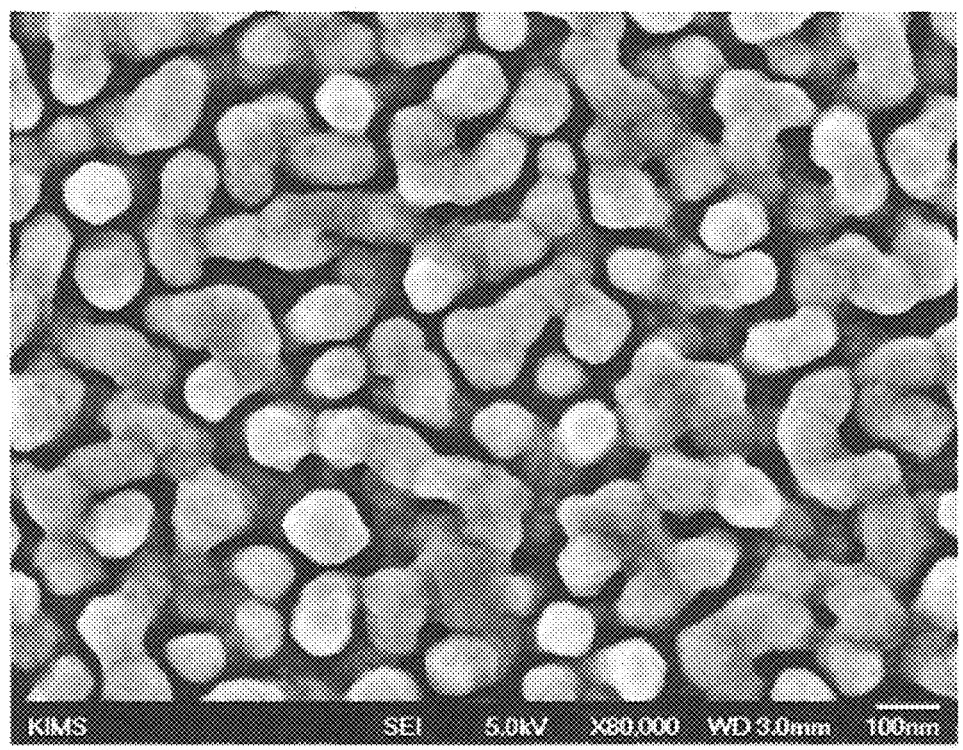
FIG. 16 is a SEM image of a substrate with multiple nano-gaps according to an example.

FIG. 16 is a SEM image of a substrate with multiple nano-gaps according to an example.

The continuous layer 230 of FIG. 16 is the same as the continuous layer 230 of FIG. 5. The metal-containing nanoparticles 240 are formed by vacuum depositing a Raman active material of Ag in 80 nm after forming the continuous layer 230. Referring to FIG. 16, fine nano-gaps are observed between the metal-containing nanoparticles 240.

Figure 17:
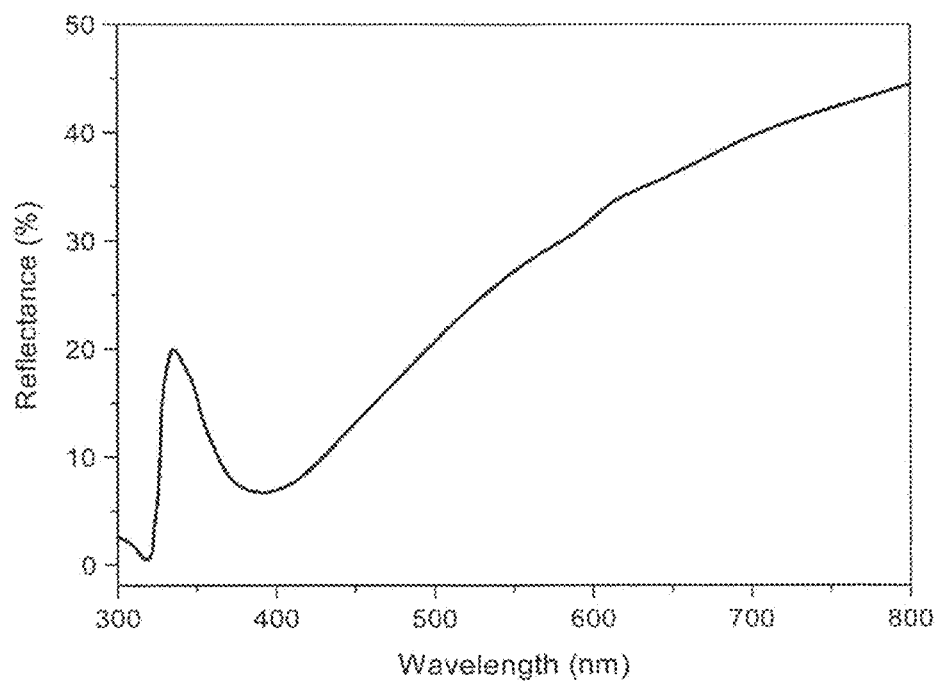
FIG. 17 is a graph illustrating reflectance of a substrate with multiple nano-gaps according to an example.

FIG. 17 is a graph illustrating reflectance of a substrate with multiple nano-gaps according to an example. Here, the substrate with multiple nano-gaps is the same as used in FIG. 16.

As result of the absorption of light at around 400 nm due to the surface plasmon resonance characteristics occurring in multiple nano-gaps consisting of nano-gaps between metal-containing nanoparticles 240 and nano-gaps between metals interposed between the inorganic material-containing thin layers, the reflectance is rapidly dropped at the same wavelength band.

Figure 18:
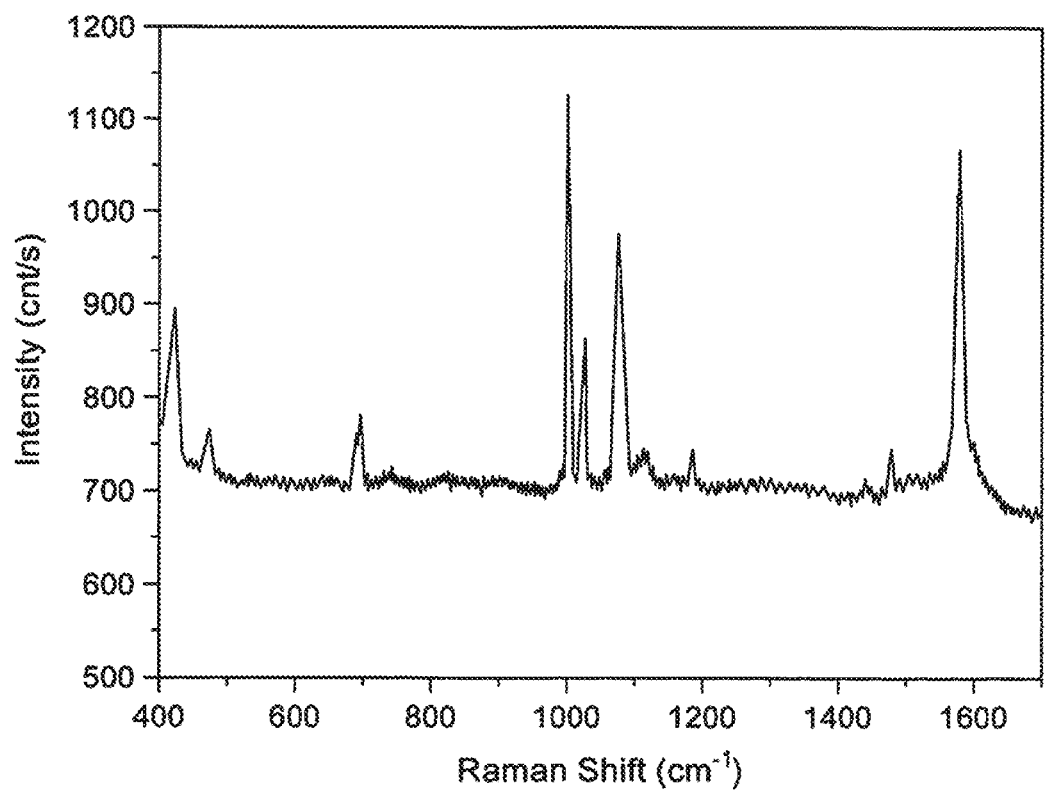
FIG. 18 is a graph illustrating Raman signal intensity of a substrate with multiple nano-gaps according to an example.

FIG. 18 is a graph illustrating Raman signal intensity of a substrate with multiple nano-gaps according to an example. Here, the substrate with multiple nano-gaps is the same as used in FIG. 16. The Raman signal intensity of benzenethiol solution is determined. Experimental conditions are as follows.

Excitation laser wavelength: 514 nm
Objective lens: 50×
Spot size: ~2 μm
Power: 0.5 mW
Benzenethiol solution concentration: 2 mM in ethanol
Exposure time: 10 sec
Raman signals of the substrate with multiple nano-gaps for benzenethiol are detected.

The substrate with multiple nano-gaps according to an example not only forms nano-gaps between the metal-containing nanoparticles 240 but also forms nano-gaps between the metal-containing nanoparticles 240 and the metal-containing thin layers 234 in the continuous layer 230 to form multiple nano-gaps which induce multiple hot spots, resulting in enhanced amplification of Raman signals.

Figure 19:
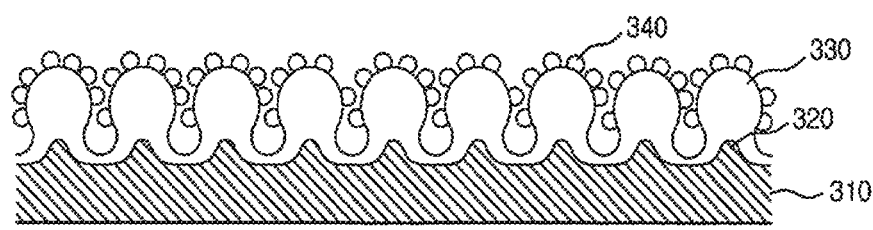
FIG. 19 is a diagram illustrating a substrate with inorganic-containing particles according to an example.

FIG. 19 is a diagram illustrating a substrate with inorganic-containing particles according to an example.

Referring to FIG. 19, a substrate with inorganic-containing particles according to an example may comprise a substrate 310, protuberant structures 320, inorganic-containing particles 330 and metal-containing nanoparticles 340

The substrate 310 may be a polymer substrate, but it is not limited thereto. The polymer substrate 310 is advantageous for forming the protuberant structures 320 in a large area even by a simple surface processing. However, any substrate can be used to have similar structure depending on processing methods.

The polymer substrate 310 may be one chosen from acrylic polymers, polyethersulfones, polycycloolefins, polyurethanes, and polycarbonates, but it is not limited thereto. Polyethylene terephthalate (PET) is used in this disclosure as the polymer substrate 310.

The protuberant structures 320 are formed by processing the substrate 310.

The protuberant structures 320 may be formed by surface-processing the polymer substrate 310 and the surface processing may be any one chosen from plasma etching, soft lithography, embossing, nano imprinting, photolithography, and holographic lithography, but it is not limited thereto.

When plasma etching is used, it is performed by using at least one chosen from argon, oxygen, hydrogen, helium, and nitrogen gas, but it is not limited thereto.

The upper part of the protuberant structures 320 may have a larger curvature than the lower part. This structure provides a condition that the inorganic material can be intensively deposited on the upper part of the protuberant structures 320 during deposition.

The inorganic-containing particles 330 are formed on the surface of the substrate 310 and the protuberant structures 320.

The inorganic material may be any one chosen from an oxide, a nitride, an oxynitride of a metal chosen from Al, Ba, Be, Ca, Cr, Cu, Cd, Dy, Ga, Ge, Hf, In, Lu, Mg, Mo, Ni, Rb, Sc, Si, Sn, Ta, Te, Ti, W, Zn, Zr, and Yb, and magnesium fluoride, but it is not limited thereto.

The inorganic-containing particles 330 may be formed by vacuum depositing an inorganic material and the inorganic material is initially uniformly deposited on the surface of the substrate 310 and the protuberant structures 320, but is intensively deposited on the upper part of the protuberant structures 320 as the deposition progresses. As the deposition progresses, because of the high curvature on the upper part of the protuberant structures 320, the accumulation of negative charges is induced on the upper part and the deposition of positively charged metal ions can be induced. This non-uniform deposition is due to the shadow effect of the already deposited inorganic-containing particles 330. That is, the amount of the inorganic material reaching the surface of the substrate 310 is significantly reduced due to the already deposited inorganic-containing particles 330, and the inorganic material is thus more intensively deposited on the upper part of the protuberant structures 320.

The inorganic-containing particles 330 are formed in a continuous thin film on the surface of the substrate 310, while the inorganic-containing particles 330 are formed in spherical or elliptical particle shapes on the protuberant structures 320.

The metal-containing nanoparticles 340 are formed on the inorganic-containing particles 330.

The metal-containing nanoparticles 340 may be formed by vacuum depositing a Raman active material and the vacuum deposition may be performed by any one chosen from sputtering, evaporation and chemical vapor deposition, but it is not limited thereto.

The Raman active material may be any one chosen from Au, Ag, Cu, Pt, Pd and an alloy thereof, but it is not limited thereto.

The deposition time may be adjusted so that the metal-containing nanoparticles 340 may be formed in granular form. When the metal-containing nanoparticles 340 are formed in granular form on the 3-dimensional inorganic-containing particles 330, multiple nano-gaps therebetween may be formed.

The metal-containing nanoparticles 340 have nano-gaps with at least one of the metal-containing nanoparticles 340 adjacent to the surface of the inorganic-containing particles 330 and the metal-containing nanoparticle 340 spatially adjacent within the substrate.

That is, on the surface of the substrate 310, nano-gaps may be formed between the metal-containing nanoparticles 340 adjacent to the surface, while on the protuberant structures 320, nano-gaps may be formed between the metal-containing nanoparticles 340 adjacent to the surface of the protuberant structures 320. Nano-gaps may also be formed between the metal-containing nanoparticles 340 which are formed on the adjacent protuberant structures 320. This is represented by spatially adjacent metal-containing nanoparticles 340.

Figure 20:
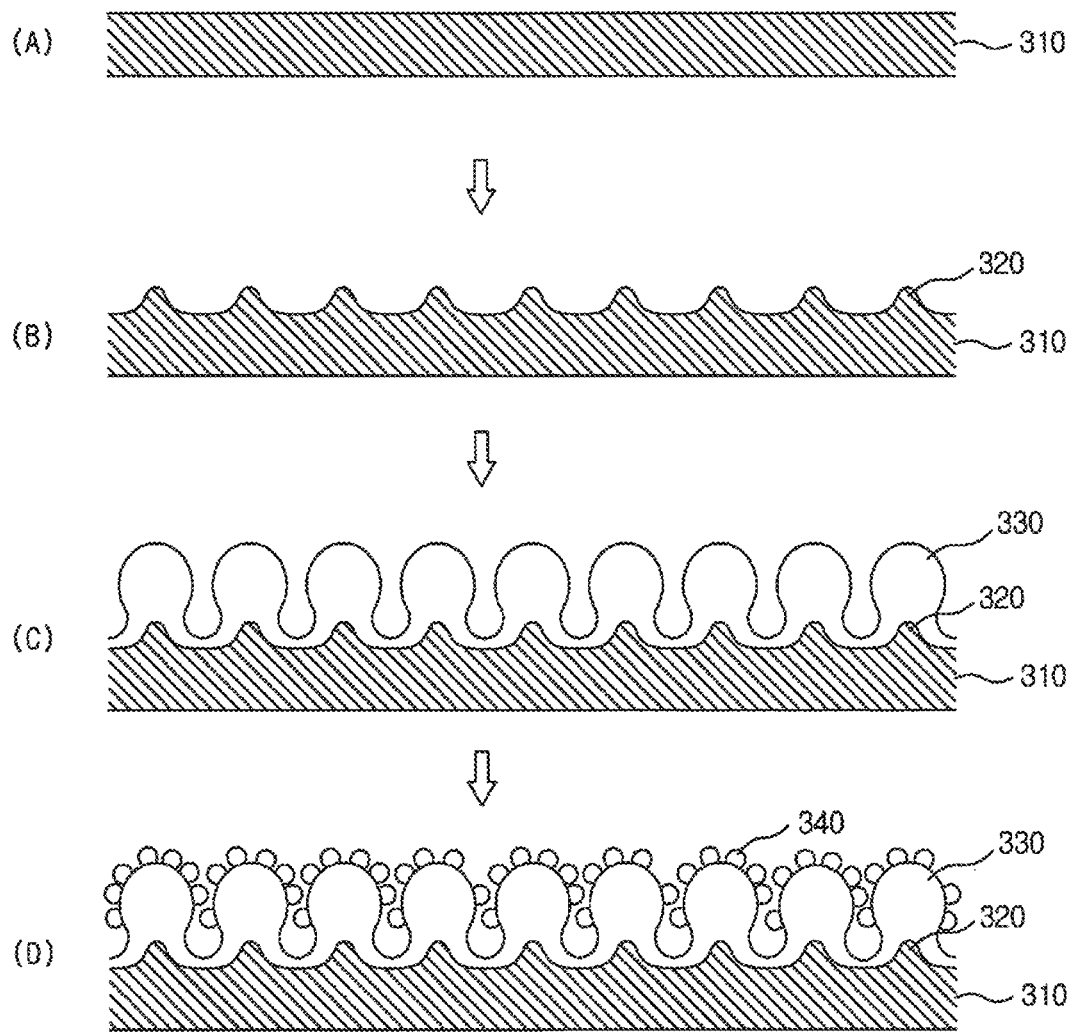
FIG. 20 is a diagram illustrating a process for manufacturing a substrate with inorganic-containing particles according to an example.

FIG. 20 is a diagram illustrating a process for manufacturing a substrate with inorganic-containing particles according to an example.

Referring to FIGS. 20(A) and 20(B), the protuberant structures 320 which are spaced-apart from each other are formed by processing the substrate 310. The protuberant structures 320 may be formed by dry etching the polymer substrate 310, but it is not limited thereto.

Referring to FIG. 20(C), the inorganic-containing particles 330 may be formed on the protuberant structures 320 and the surface of the substrate 310. The inorganic-containing particles 330 may be formed by vacuum depositing an inorganic material The inorganic-containing particles 330 may be intensively deposited on the upper part of the protuberant structures 320 to form a continuous thin film on the surface of the substrate 310 and spherical or elliptical particles on the protuberant structures 320.

Referring to FIG. 20(D), the metal-containing nanoparticles 340 are formed on the inorganic-containing particles 330. The metal-containing nanoparticles 340 may be formed by vacuum depositing a Raman active material and the deposition time may be adjusted so that the metal-containing nanoparticles 340 can be formed in granular form.

The substrate with inorganic-containing particles manufactured by the method described above includes multiple nano-gaps and has advantageous characteristics of inorganic material as follows.

First, when the protuberant structures 320 are formed of a polymer, the adhesion between the polymer and the metal-containing nanoparticles 340 may be weak. However, the inorganic material acts as an intermediate mediator to enhance the adhesion, resulting in structural stability.

Second, when the polymer substrate is used for Raman spectrum, the high energy of the Raman laser can cause deformation of the substrate 310. However, the inorganic-containing particles 330 of the substrate can mitigate this thermal deformation.

Third, the inorganic-containing particles 330 can block the noise according to the shape of the substrate 310 itself more than a certain level, thereby making it possible to further clarify the analysis of Raman signals.

Fourth, by using the structural characteristics of the protuberant structures 320 and the inorganic-containing particles 330, multiple nano-gaps are formed between the metal-containing nanoparticles 340, so that the amplified Raman signal can be obtained when the Raman signal is measured.

Figure 21:
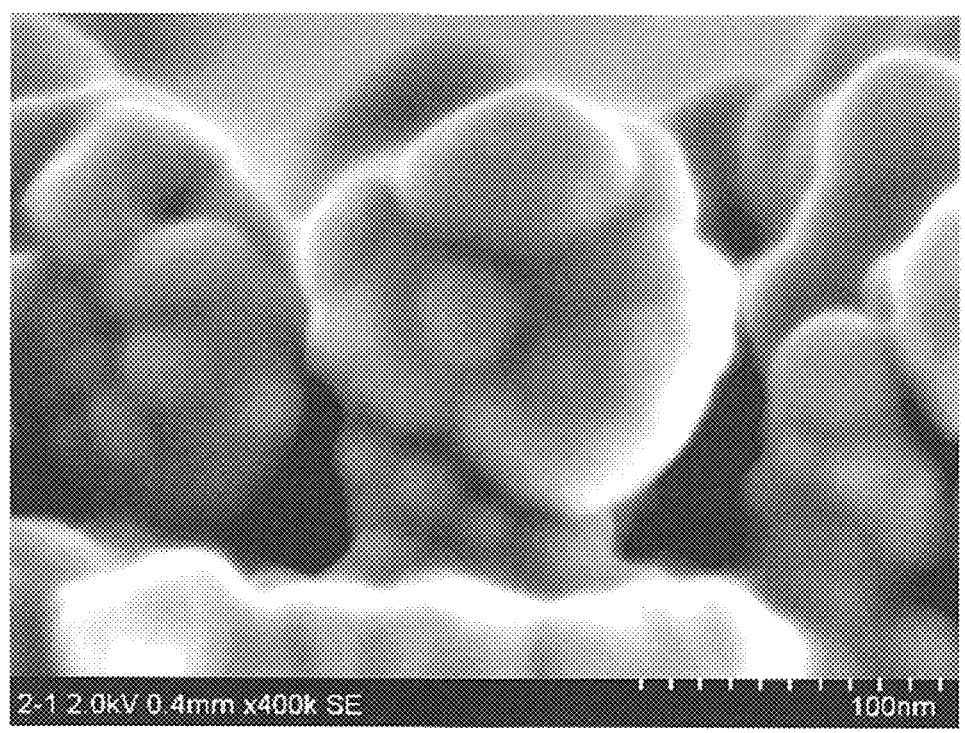
FIG. 21 is a SEM image of a substrate with inorganic-containing particles according to an example.

FIG. 21 is a SEM image of a substrate with inorganic-containing particles according to an example. The protuberant structures 320 are formed by etching a polyethylene terephthalate (PET) polymer substrate 310 with RF power of 200 W for 2 min. The inorganic-containing particles 330 are formed by depositing $SiO_2$ in 80 nm on the protuberant structures 320 and the metal-containing nanoparticles 340 are formed by depositing Ag in 20 nm on the inorganic-containing particles 330.

Referring to FIG. 21, the metal-containing nanoparticles 340 form nano-gaps with both the metal-containing nanoparticles 340 adjacent to the surface and the spatially adjacent metal-containing nanoparticles 340.

Figure 22:
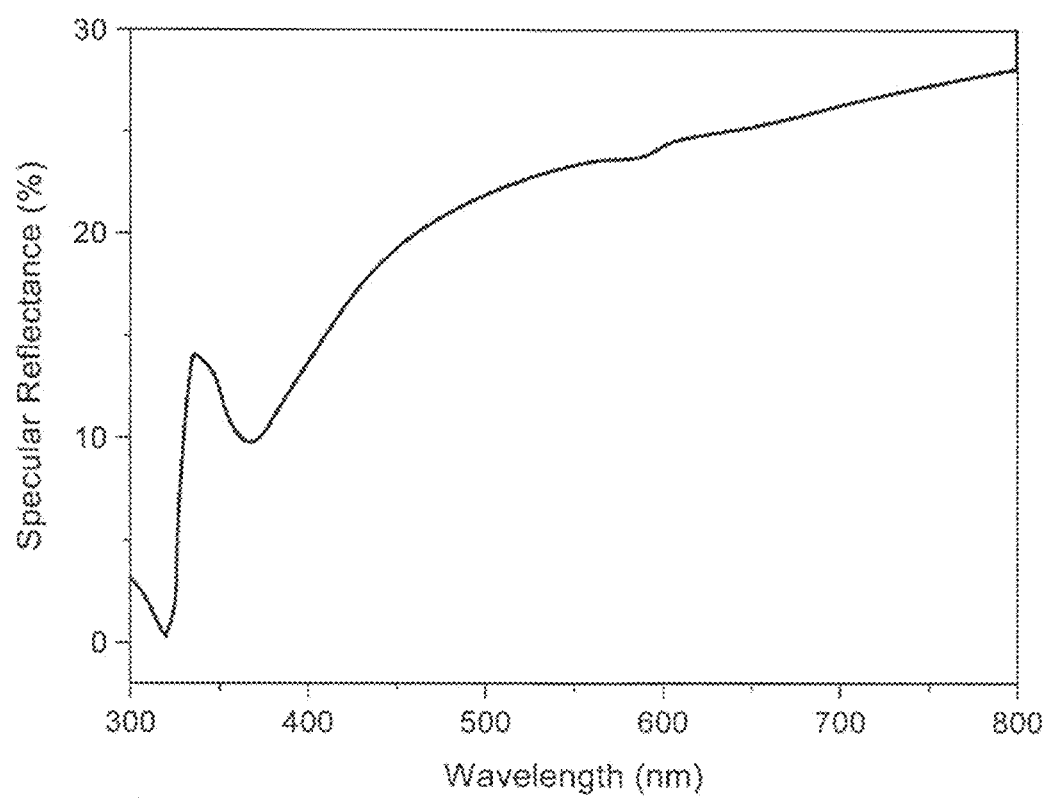
FIG. 22 is a graph illustrating reflectance of a substrate with inorganic-containing particles according to an example.

FIG. 22 is a graph illustrating reflectance of a substrate with inorganic-containing particles according to an example.

As result of the absorption of light at around 350 to 400 nm due to the surface plasmon resonance characteristics occurring in multiple nano-gaps consisting of nano-gaps between the metal-containing nanoparticles 340, the reflectance is rapidly dropped at the same wavelength band.

Figure 23:
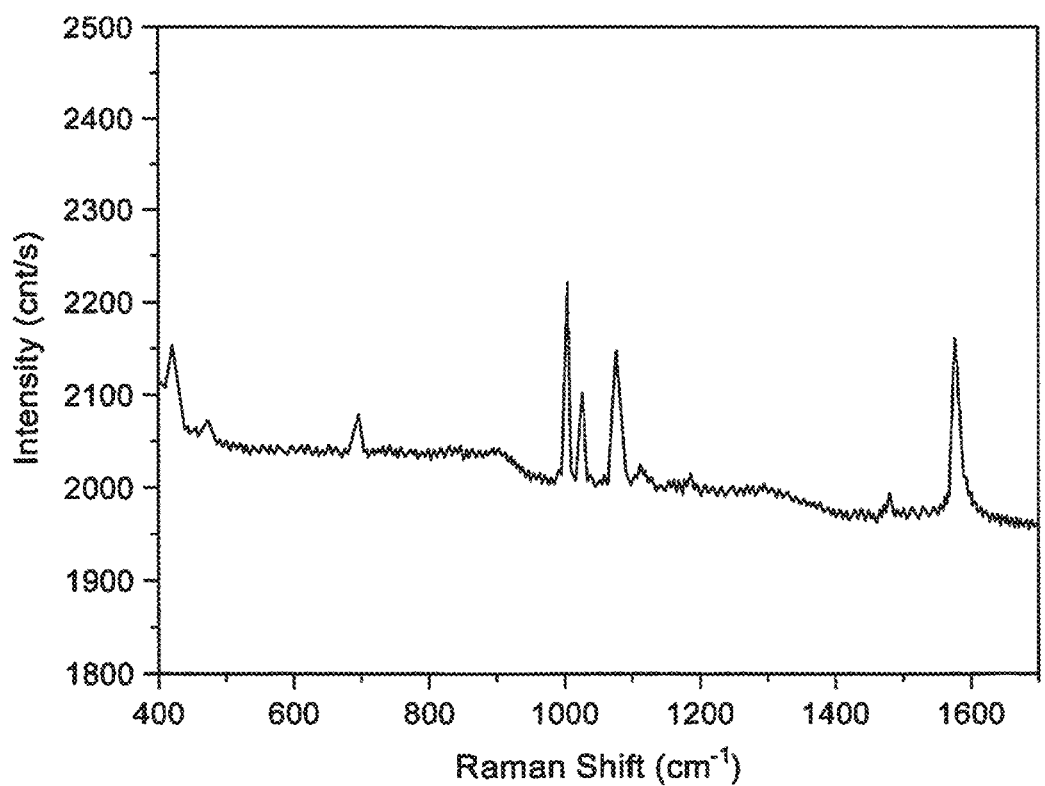
FIG. 23 is a graph illustrating Raman signal intensity of a substrate with inorganic-containing particles according to an example.

FIG. 23 is a graph illustrating Raman signal intensity of a substrate with inorganic-containing particles according to an example.

Raman signals of benzenethiol at a concentration of 2 mM (mole/liter) in ethanol are detected from Raman measurements using a 514 nm laser wavelength due to LSPR effects from multiple nano-gaps between the metal-containing nanoparticles 340.

Figure 24:
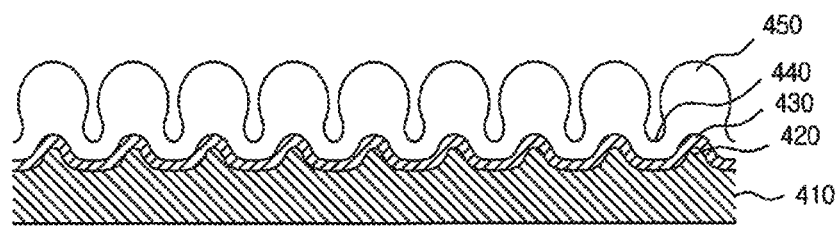
FIG. 24 is a diagram illustrating a substrate with inorganic-metal structures according to an example.

FIG. 24 is a diagram illustrating a substrate with inorganic-metal structures according to an example.

Referring to FIG. 24, a substrate with inorganic-metal structures may comprise a substrate 410, protuberant structures 420, an inorganic material-containing thin layer 430, a metal-containing thin layer 440 and metal-containing nanoparticles 450.

The substrate 410 may be a polymer substrate. The polymer substrate 410 is advantageous for forming the protuberant structures 420 in a large area even by a simple surface processing. However, any substrate can be used to have similar structure depending on processing methods.

The polymer substrate 410 may be one chosen from acrylic polymers, polyethersulfones, polycycloolefins, polyurethanes, polyethylene terephthalates and polycarbonates, but it is not limited thereto.

Polyethylene terephthalate (PET) is used in this disclosure as the polymer substrate 410.

The protuberant structures 420 are formed by processing the substrate 410.

The protuberant structures 420 may be formed by surface-processing the polymer substrate 410 and the surface processing may be any one chosen from plasma etching, soft lithography, embossing, nano imprinting, photolithography, and holographic lithography, but it is not limited thereto.

When plasma etching is used, it is performed by using at least one chosen from argon, oxygen, hydrogen, helium, and nitrogen gas, but it is not limited thereto.

The protuberant structures 420 have upper protruded curved surfaces. Having upper protruded curved surface means that the upper portion of the protuberant structures 420 has a larger curvature than the lower part. This structure provides a condition that the Raman active material can be intensively deposited on top during deposition.

The inorganic material-containing thin layer 430 is deposited on the surface of the substrate 410 and the protuberant structures 420.

Due to the structural nature of the protuberant structures 420, the deposition may be intensively deposited on the upper part over time, but before that the deposition is stopped. The deposition thickness of the inorganic material-containing thin layer 430 is preferably 5 nm to 50 nm. The inorganic material-containing thin layer 430 has a minimum thickness of 5 nm to form a continuous thin film on the polymer substrate 410. If the thickness exceeds 50 nm, the inorganic material can grow into inorganic-containing particles rather than the continuous film.

The inorganic material may be any one chosen from an oxide, a nitride, an oxynitride of a metal chosen from Al, Ba, Be, Ca, Cr, Cu, Cd, Dy, Ga, Ge, Hf, In, Lu, Mg, Mo, Ni, Rb, Sc, Si, Sn, Ta, Te, Ti, W, Zn, Zr, and Yb, and magnesium fluoride, but it is not limited thereto.

The inorganic material-containing thin layer 430 may be formed by a vacuum depositing an inorganic material and the vacuum deposition may be performed by any one chosen from sputtering, evaporation and chemical vapor deposition, but it is not limited thereto.

Sputtering is used in an example of this disclosure. The substrate 410 on which the protuberant structures are formed by dry etching is placed in a vacuum chamber and the vacuum chamber is maintained to have vacuum degree of $2 \times 10^{-5}$ torr using a low vacuum pump and a high vacuum pump. Ar operation gas is injected to reach an operation vacuum of $2 \times 10^{-3}$ torr. Power is applied to a plasma generating power source connected to a sputtering target with the inorganic material of $SiO_2$. Plasma is generated and the inorganic material is deposited on the surface of substrate 410 and protuberant structures 420.

Figure 27:
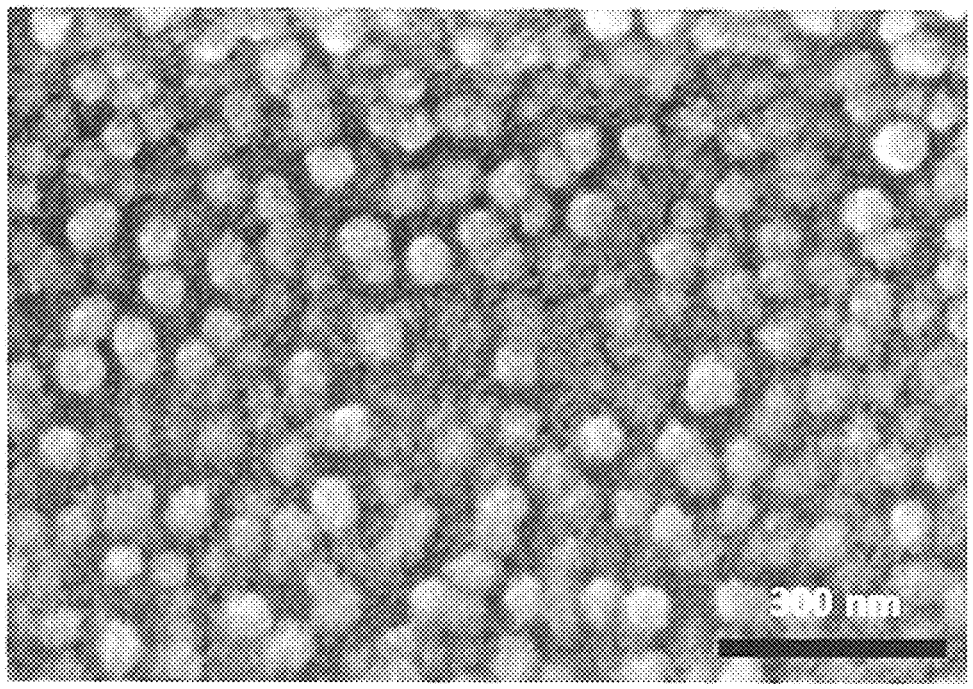
FIG. 27 is a SEM image of an inorganic material-containing thin layer according to an example.

Processing conditions are as follows.
Base substrate: polyethylene terephthalate (PET) thickness 188 mm, Transmittance. 90%
Initial vacuum degree: $2 \times 10^{-5}$ torr
Sputtering target for coating an inorganic material: $SiO_2$ (Size: 4 inch)
Operation gas: Ar
Operation vacuum degree: $2 \times 10^{-3}$ torr
RF power: 200 W FIG. 27 is a SEM image of the inorganic material-containing thin layer 430 according to an example. The inorganic material-containing thin layer 430 of FIG. 27 is formed by depositing an inorganic material of $SiO_2$ in a 20 nm thickness on the protuberant structures 420 which is formed by etching a polyethylene terephthalate substrate 410 with RF power of 200 W for 2 min.

Referring to FIG. 24, the metal-containing thin layer 440 is formed on the surface of the substrate 410 on which the inorganic material-containing thin layer 430 is formed.

The metal-containing nanoparticles 450 are formed on the protuberant structures 420 on which the inorganic material-containing thin layer 430 is formed.

The metal-containing thin layer 440 and metal-containing nanoparticles 450 may be formed at the same time by vacuum depositing a Raman active material and the vacuum deposition may be performed by any one chosen from sputtering, evaporation and chemical vapor deposition, but it is not limited thereto.

The Raman active material is initially uniformly deposited on the metal thin film and the protuberant structures 420, but is intensively deposited on the upper part of the protuberant structures 420 as the deposition progresses. As the deposition progresses, because of the high curvature on the upper part of the protuberant structures 420, the accumulation of negative charges is induced on the upper part and the deposition of positively charged metal ions can be induced. This non-uniform deposition is due to the shadow effect of already deposited metal-containing nanoparticles 450. That is, the amount of the Raman active material reaching the surface of the substrate 410 is significantly reduced due to the already deposited metal-containing nanoparticles 450, and the Raman active material is thus more intensively deposited on the upper part of the protuberant structures 420.

The nano-gaps, which are the spacing of the metal-containing nanoparticles 450, can be controlled by adjusting the spacing of the protuberant structures 420 and the size of the metal-containing nanoparticles 450. The spacing of the protuberant structures 420 can be controlled by controlling the etching time, and the size of the metal-containing nanoparticles 450 can be controlled by adjusting the deposition time of the Raman active material.

Figure 28:
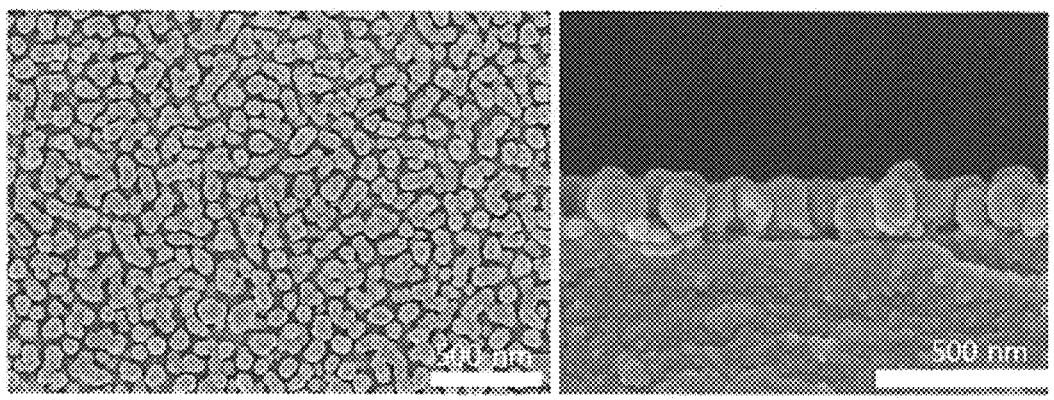
FIG. 28 is a SEM image of a substrate with inorganic-metal structures according to an example.

FIG. 28 is a SEM image of a substrate with inorganic-metal structures according to an example.

The Ag metal-containing nanoparticles 450 of FIG. 28 are formed in a 80 nm thickness on the substrate 410 of FIG. 27. Referring to FIG. 28, nano-gaps may be formed between the metal-containing nanoparticles 450. The nano-gap can be controlled by the deposition time of the Raman active material and can be controlled at a few nm level.

Figure 25:
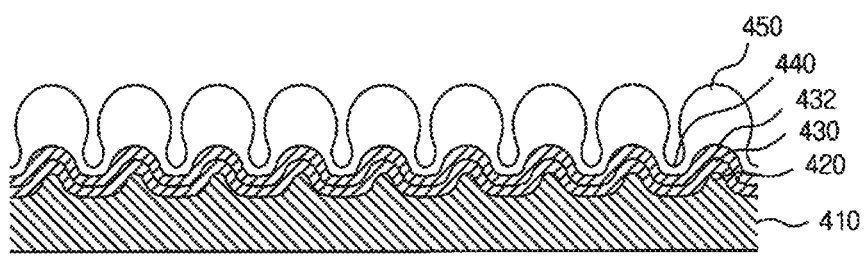
FIG. 25 is a diagram illustrating a substrate with inorganic-metal structures according to another example.

FIG. 25 is a diagram illustrating a substrate with inorganic-metal structures according to another example.

Referring to FIG. 25, a substrate with inorganic-metal structures according to another example may comprise a substrate 410, protuberant structures 420, an inorganic material-containing thin layer 430, a metal-containing thin layer 440 and metal-containing nanoparticles 450. The substrate with inorganic-metal structures according to another example may further comprise an inorganic material-containing thin layer 432 including an inorganic material different from that included in the inorganic material-containing thin layer 430.

The inorganic material-containing thin layer 432 may be formed between the inorganic material-containing thin layer 430 and the substrate 410. The inorganic material-containing thin layer 432 may be formed in a layer or multi-layers including different inorganic materials.

Figure 26:
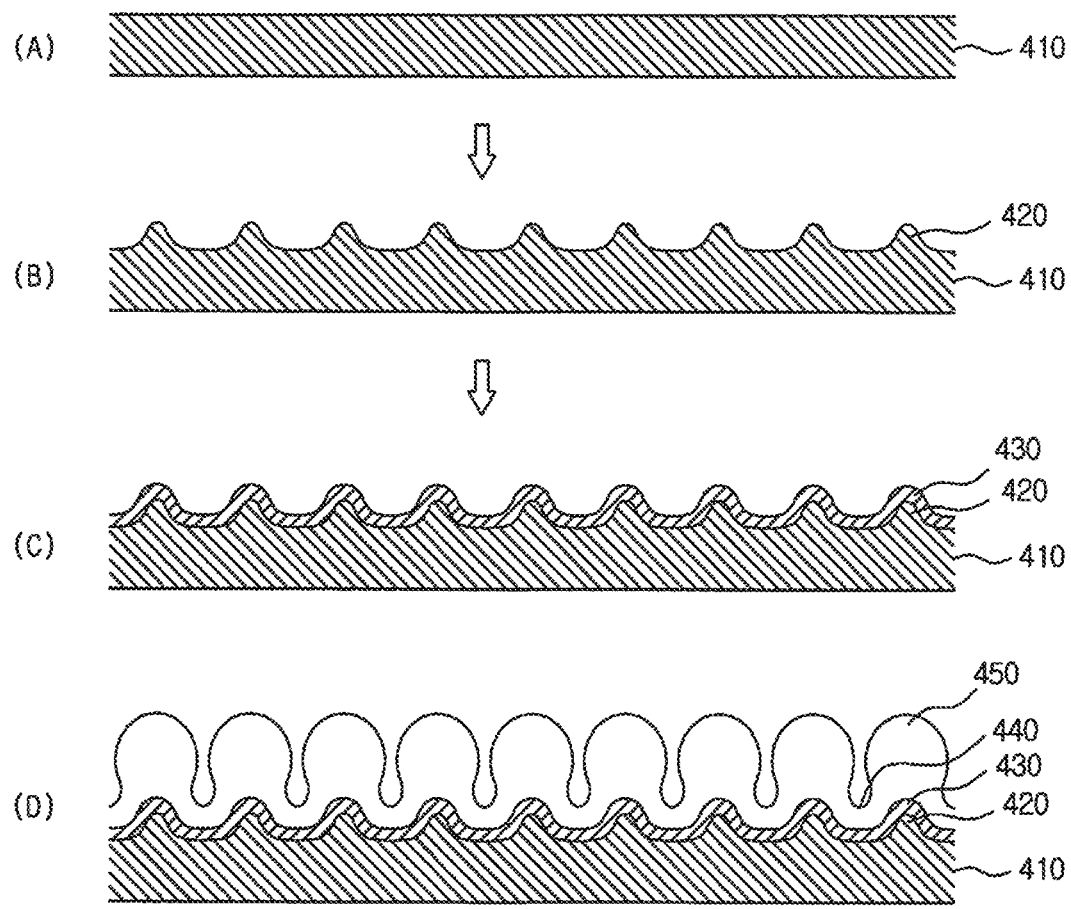
FIG. 26 is a diagram illustrating a process for manufacturing a substrate with inorganic-metal structures according to an example.

FIG. 26 is a diagram illustrating a process for manufacturing a substrate with inorganic-metal structures according to an example.

Referring to FIGS. 26(A) and 26(B), the protuberant structures 420 having upper protruded curved surfaces are formed to be spaced-apart from each other by processing the substrate 410. The protuberant structures 420 may be formed by dry etching, but it is not limited thereto.

Referring to FIG. 26(C), the inorganic material-containing thin layer 430 is formed on the surface of the substrate 410 and the protuberant structures 420. The inorganic material-containing thin layer 430 may be formed by vacuum depositing an inorganic material, but it is not limited thereto. When the inorganic material is vacuum-deposited, the deposition time can be controlled so that the inorganic material is not intensively deposited on the upper part.

Referring to FIG. 26(D), the metal-containing thin layer 440 and the metal-containing nanoparticles 450 can be formed at the same time by vacuum depositing a Raman active material on the surface of the substrate 410 on which the inorganic material-containing thin layer 430 is formed and protuberant structures 420. The Raman active material is initially uniformly deposited on the surface of the substrate 410 and protuberant structures 420, but is intensively deposited on the protuberant structures 420 as the deposition progresses. The metal-containing nanoparticles 450 are formed in a spherical or elliptical shape as shown in FIG. 26(D).

Figure 29:
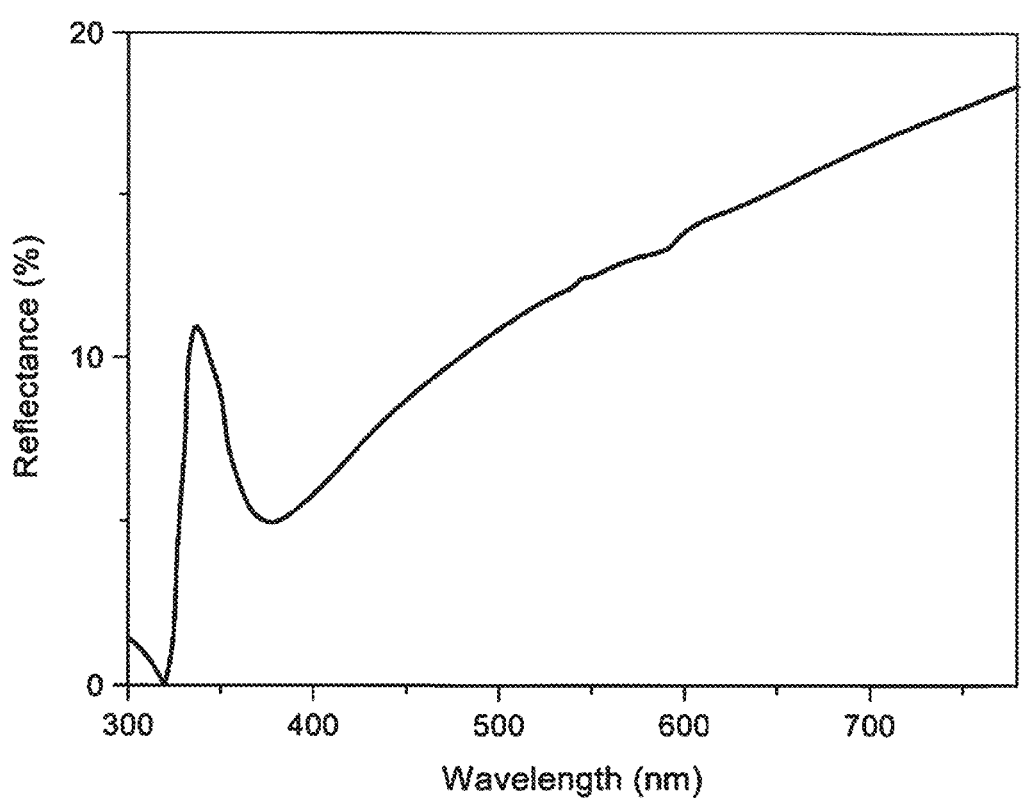
FIG. 29 is a graph illustrating reflectance of a substrate with inorganic-metal structures according to an example.

FIG. 29 is a graph illustrating reflectance of a substrate with inorganic-metal structures according to an example. The substrate with inorganic-metal structures is used under the same conditions as in FIG. 28.

As result of the absorption of light at around 350-400 nm due to the plasmon characteristics of the metal-containing nanoparticles 450, the reflectance is rapidly dropped at the same wavelength band.

Figure 30:
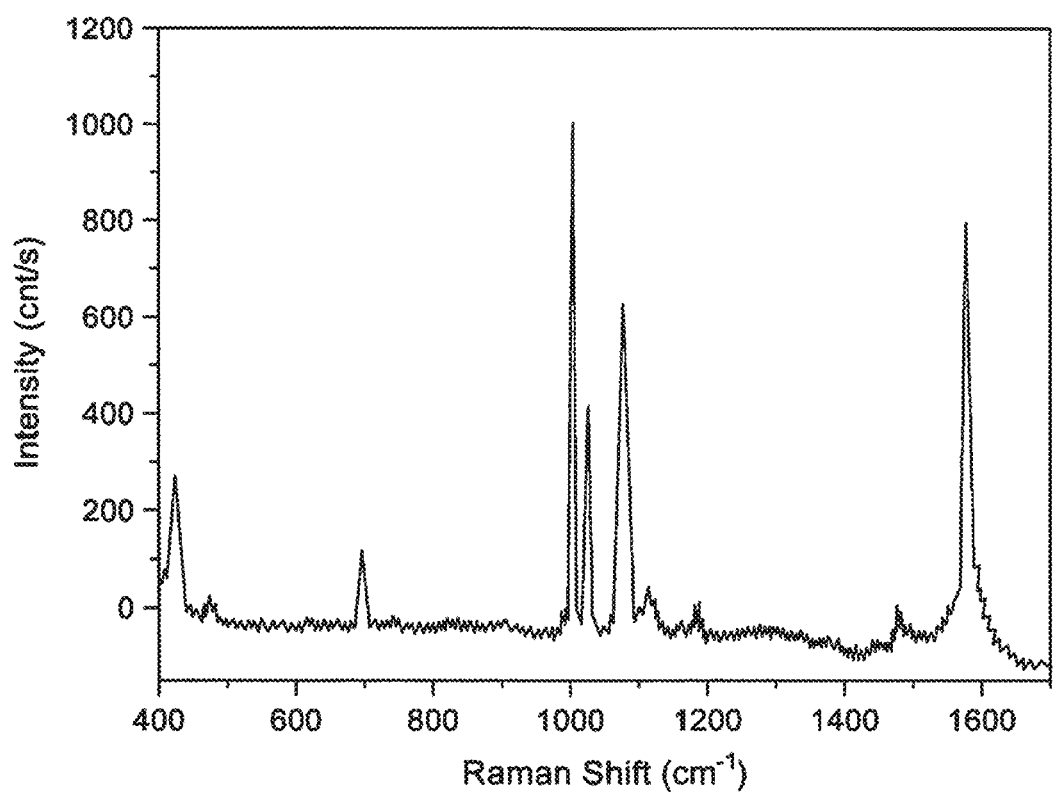
FIG. 30 is a graph illustrating Raman signal intensity of a substrate with inorganic-metal structures according to an example.

FIG. 30 is a graph illustrating Raman signal intensity of a substrate with inorganic-metal structures according to an example. Here, the substrate with inorganic-metal structures is the same as used in FIG. 28. The Raman signal intensity of benzenethiol molecules is determined.

Experimental conditions are as follows.
Excitation laser wavelength: 514 nm
Objective lens: 50×
Spot size: ~2 μm
Power: 0.5 mW
Benzenethiol solution concentration: 2 mM in ethanol
laser Exposure time: 10 sec
Raman signal intensity of benzenethiol is determined from the inorganic material-metal structure according to one example of this disclosure in FIG. 30.

Technical features of the substrate with inorganic-metal structures of this disclosure are as follows.

First, when the polymer substrate 410 is used, the adhesion between the polymer and the metal-containing nanoparticles 340 may be weak. However, the inorganic material acts as an intermediate mediator to enhance the adhesion, resulting in structural stability.

Second, when the polymer substrate is used for Raman spectrum, the high energy of the Raman laser can cause deformation of the substrate 410. However, the material-containing thin layer 430 of the substrate can mitigate this thermal deformation.

Third, the inorganic material-containing thin layer 430 can block the noise according to the shape of the substrate 410 itself more than a certain level, thereby making it possible to further clarify the classification of Raman signals.

Fourth, by forming the inorganic material-containing thin layer 430 on the polymer substrate 410 and the protuberant structures 420, the following problems may be eliminated: etching of the polymer substrate 410 caused when the metal-containing thin layer 440 and the metal-containing nanoparticles 450 are grown directly on the polymer substrate 410 and the protuberant structures 420; contamination of the metal structure caused by the vaporization of oxygen in the polymer; and transformation of Raman spectrum characteristics.

Fifth, finer nano-gap control can be achieved because the metal-containing nanoparticles 450 can be intensively formed on the upper part of the protuberant structures 420 and their size can be controlled.

Figure 31:
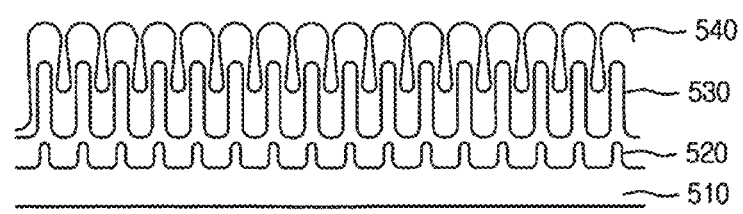
FIG. 31 is a diagram illustrating an inorganic material-grown substrate according to an example.

FIG. 31 is a diagram illustrating an inorganic material-grown substrate according to an example.

Referring to FIG. 31, an inorganic material-grown substrate according to an example may comprise a substrate 510, protuberant structures 520, an inorganic material-containing bar 530 and metal-containing nanoparticles 540.

The substrate 510 may be a polymer substrate, but it is not limited thereto. The polymer substrate 510 is advantageous for forming the protuberant structures 520 in a large area even by a simple surface processing. However, any substrate can be used to have similar structure depending on processing methods.

The polymer substrate 510 may be one chosen from acrylic polymers, polyethersulfones, polycycloolefins, polyurethanes, polyethylene terephthalates and polycarbonates, but it is not limited thereto.

The protuberant structures 520 are formed by processing the substrate 510.

The protuberant structures 520 may be formed by surface-processing the polymer substrate 510 and the surface processing may be any one chosen from plasma etching, soft lithography, embossing, nano imprinting, photolithography, and holographic lithography, but it is not limited thereto.

When plasma etching is used, it is performed by using at least one chosen from argon, oxygen, hydrogen, helium, and nitrogen gas, but it is not limited thereto.

FIG. 34 illustrates SEM images of protuberant structures 520 according to an example.

The protuberant structures 520 of FIG. 34 are formed by plasma etching the polyethylene terephthalate polymer substrate 510 with RF power of 200 W for 2 min.

Referring to FIG. 34, the protuberant structures 520 are formed to be spaced-apart from each other and show irregular shapes and sizes.

Referring to FIG. 31 again, the inorganic material-containing bar 530 is grown at the position where the protuberant structures 520 are formed.

The inorganic material may be any one chosen from an oxide, a nitride, an oxynitride of a metal chosen from Al, Ba, Be, Ca, Cr, Cu, Cd, Dy, Ga, Ge, Hf, In, Lu, Mg, Mo, Ni, Rb, Sc, Si, Sn, Ta, Te, Ti, W, Zn, Zr, and Yb, and magnesium fluoride, but it is not limited thereto.

The inorganic material-containing bar 530 may be grown in the following method.

When an inorganic material is vacuum deposited on the substrate 510 on which the protuberant structures 520 are formed, the inorganic material is uniformly deposited on the surface of the substrate 510 and the protuberant structures 520. Here, the first inorganic material-containing layer may be formed at the same time on the surface of the substrate 510. However, the inorganic material is intensively deposited on the upper part of the protuberant structures 520 over time to form the inorganic material-containing bar 530. This is because the inorganic material-containing bar 530 grows vertically at the top of the protuberant structures 520 due to the shadow effect and the deformation of the polymer surface energy.

The vacuum deposition may be performed by any one chosen from sputtering, evaporation and chemical vapor deposition, but it is not limited thereto.

The inorganic material-containing bar 530 may be formed by sputtering.

The protuberant structures 520 are formed by dry etching the polymer substrate 510 in a vacuum chamber and the vacuum chamber is maintained to have vacuum degree of $2\times10^{-5}$ torr using a low vacuum pump and a high vacuum pump. Ar operation gas is injected to reach an operation vacuum of $2\times10^{-3}$ torr. Power is applied to a plasma generating power source connected to a sputtering target with the inorganic material of ZnO. Plasma is generated and the inorganic material is deposited on the surface of substrate 510 and protuberant structures 520.

Processing conditions are as follows.

Base substrate: PET thickness 188 mm, Transmittance. 90%
Initial vacuum degree: $2\times10^{-5}$ torr
Sputtering target for coating an inorganic material: ZnO (size: 4 inch, components: no doping)
Operation gas: Ar
Operation vacuum degree: $2\times10^{-3}$ torr
RF power: 200 W A second inorganic material-containing layer may be further formed between the first inorganic material-containing layer and the protuberant structures. Here, the second inorganic material-containing layer may be formed before the first inorganic material-containing layer is formed. The inorganic material may be any one chosen from an oxide, a nitride, an oxynitride of a metal chosen from Al, Ba, Be, Ca, Cr, Cu, Cd, Dy, Ga, Ge, Hf, In, Lu, Mg, Mo, Ni, Rb, Sc, Si, Sn, Ta, Te, Ti, W, Zn, Zr, and Yb, and magnesium fluoride, but it is not limited thereto.

FIG. 35 illustrates SEM images of an inorganic material-containing bar 530 according to an example.

Referring to FIG. 35, the inorganic material-containing bar 530 has a one-dimensional rod shape (grown at one point) and diameter and spacing can be controlled at several tens of nanometers.

The spacing between the inorganic material-containing bars 530 may be controlled by at least one of the spacing between the protuberant structures 520 and the diameter of the inorganic material-containing bar 530.

The metal-containing nanoparticles 540 are formed on the inorganic material-containing bar 530.

The metal may be any one chosen from Au, Ag, Cu, Pt and Pd, and an alloy thereof, but it is not limited thereto.

The metal-containing nanoparticles 540 may also be grown similar to the inorganic material-containing bar 530.

The metal-containing nanoparticles 540 are formed by vacuum depositing a Raman active material. The Raman active material is initially uniformly deposited on the first inorganic material-containing layer and the inorganic material-containing bar 530, but is intensively deposited on the upper part of the inorganic material-containing bar as the deposition progresses. This is due to the shadow effect of the already deposited metal-containing nanoparticles 540.

Both the inorganic material-containing bar 530 and the metal-containing nanoparticles 540 are asymmetrically grown but there is a difference in the form therebetween due to the shadow effect in the deposition. ZnO used in this disclosure grows in the form of rods because of its strong tendency to grow vertically. However, the metal-containing nanoparticles 540 are, as shown in FIG. 33, concentrated on the top, but do not grow to the shape of a bar.

In FIG. 33(A), the metal-containing nanoparticles 540 are formed on the upper part of the inorganic material-containing bar 530 and the metal layer is also deposited between the valleys of the inorganic material-containing bar 530. However, in FIG. 33(B), the metal-containing nanoparticles 540 are formed in spherical or oval shapes only on the upper part of the inorganic material-containing bar 530.

Nano-gaps may be formed between the metal-containing nanoparticles 540. These nano-gaps may serve as hot spots in the Raman spectrum.

The nano-gap may be controlled by controlling the spacing between protuberant structures 520 when forming the protuberant structures 520, the diameter of the inorganic material-containing bar 530 when forming the inorganic material-containing bar 530, the size of the metal-containing nanoparticles 540 when forming the metal-containing nanoparticles 540 or two or more of these three factors.

Figure 36:
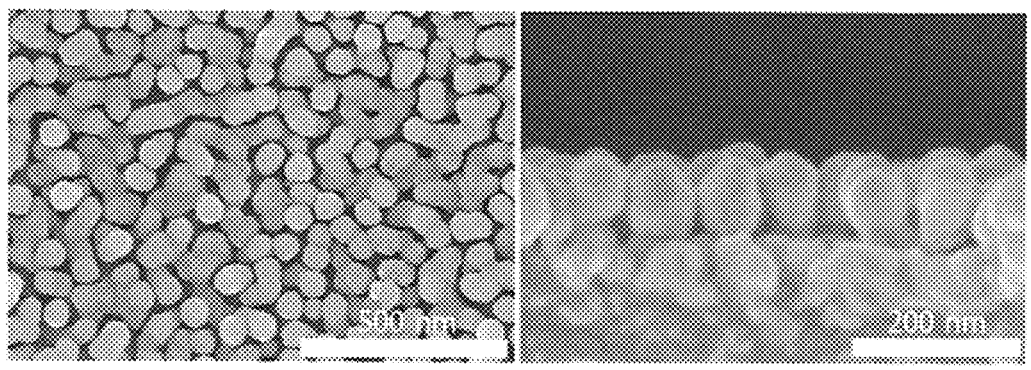
FIG. 36 illustrates SEM images of an inorganic material-grown substrate according to an example.

FIG. 36 illustrates SEM images of an inorganic material-grown substrate according to an example. The metal-containing nanoparticles 540 are formed by depositing a Raman active material of Ag in a thickness of 60 nm.

Referring to FIG. 36, fine nano-gaps are formed between the metal-containing nanoparticles 540.

Figure 32:
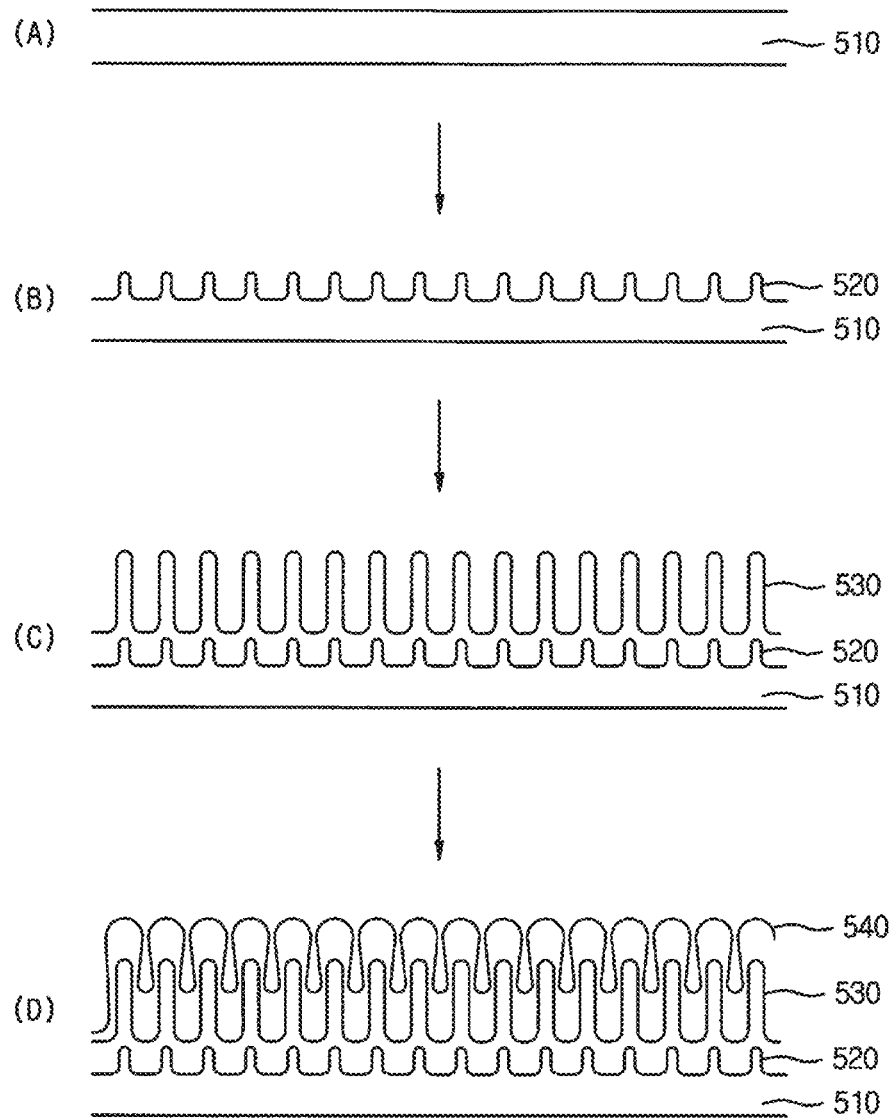
FIG. 32 is a diagram illustrating a process for manufacturing an inorganic material-grown substrate according to an example.

FIG. 32 is a diagram illustrating a process for manufacturing an inorganic material-grown substrate according to an example.

Referring to FIGS. 32(A) and 32(B), the protuberant structures spaced-apart from each other 520 are formed by processing the substrate 510.

Referring to FIG. 3(C), the inorganic material-containing bar 530 is formed by growing an inorganic material at the point where the protuberant structures 520 are formed.

Referring to FIG. 32(D), the metal-containing nanoparticles 540 are formed by depositing a Raman active material on the inorganic material-containing bar 530. The metal-containing nanoparticles 540 may be formed in a spherical shape only on the inorganic material-containing bar 530 and may be formed continuously with the metal layer formed between the valleys of the inorganic material-containing bar 530 as described above.

Figure 37:
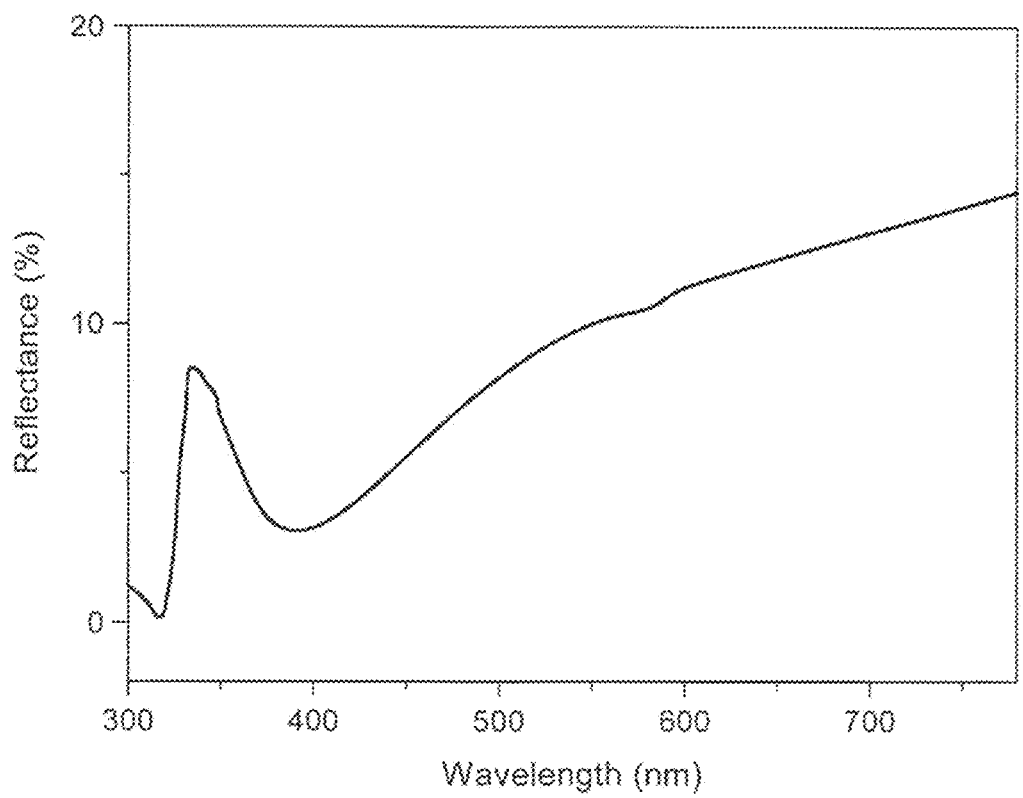
FIG. 37 is a graph illustrating reflectance of an inorganic material-grown substrate according to an example.

FIG. 37 is a graph illustrating reflectance of an inorganic material-grown substrate according to an example.

Processing conditions of the inorganic material-grown substrate 510 of FIG. 37 are the same as described above.

As result of the absorption of light at around 400 nm due to the surface plasmon resonance characteristics of the metal-containing nanoparticles 540, the reflectance is rapidly dropped at the same wavelength band.

Figure 38:
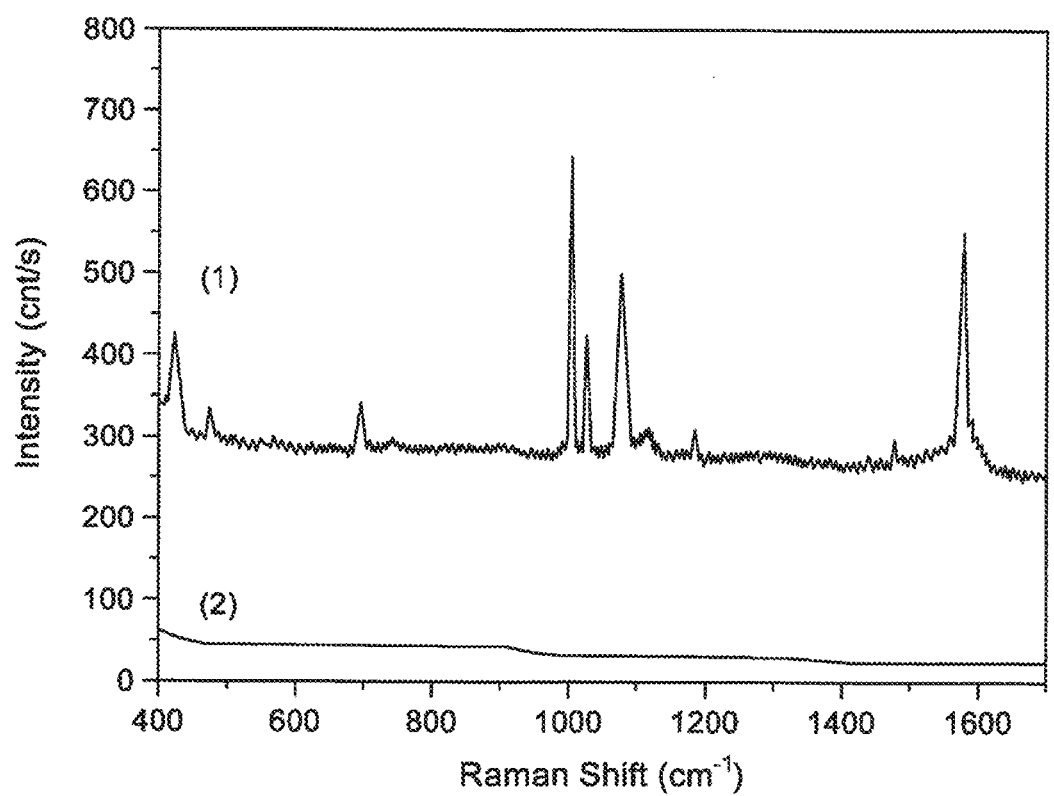
FIG. 38 is a graph illustrating Raman signal intensities of an inorganic material-grown substrate according to an example and a non-inorganic material-grown substrate.

FIG. 38 is a graph illustrating Raman signal intensities of an inorganic material-grown substrate according to an example and a non-inorganic material-grown substrate.

In FIG. 38(1), Raman signal intensity of benzenethiol (BT) is determined for the substrate 510 formed under the same conditions of an example of the present disclosure. In FIG. 38(2), Raman signal intensity of benzenethiol (BT) is determined for the polymer substrate on which Ag without an inorganic material is deposited in a 60 nm thickness on the protuberant structures 520.

Measurement conditions of Raman signal intensity are as follows.

Excitation laser wavelength=514 nm
Objective lens=50×
Spot size=~2 μm
Power=0.5 mW
BT solution concentration=2 mM in ethanol
Exposure time=10 sec When the Raman signal intensities of FIGS. 38(1) and 38(2) are compared, the substrate 510 of (1) formed with inorganic material exhibits much stronger Raman signal intensity.

The inorganic material-grown substrate according to this disclosure has the following advantages.

First, when the protuberant structures 520 are formed of a polymer, the adhesion between the polymer and the metal may be weak. However, the inorganic material acts as an intermediate mediator to enhance the adhesion, resulting in structural stability.

Second, when the polymer substrate is used for Raman spectrum, the high energy of the Raman laser can cause deformation of the substrate 510. However, the inorganic-containing particles 530 of the substrate can mitigate this thermal deformation and further alleviate the spacing between metal-containing nanoparticles 540 by thermal deformation during Raman analysis.

Third, the inorganic-containing particles 530 can block the noise according to the shape of the substrate 510 itself more than a certain level, thereby making it possible to further clarify the classification of Raman signals.

Fourth, when the substrate is formed only with the structural characteristics of the protuberant structures and the inorganic-containing particles, the density of the protuberant structures is reduced during the growth of the protuberant structures above a certain height (development from FIG. 39(A) to 39(B)). When low-density protuberant structures are relatively spaced apart and the metal-containing nanoparticles are formed directly on the protuberant structures, in order to reduce the nano-gap between the metal-containing nanoparticles, metal-containing nanoparticles must be grown large. However, in the case of the inorganic material-grown substrate of this disclosure, the inorganic material-containing bar 530 compensates for the height of the protuberant structures 520, so that the protuberant structures 520 of the polymer formed at a lower height can be used (FIG. 39(A)). Thus, even if the inorganic material-containing bars 530 are formed at a high density and the metal-containing nanoparticles 540 are grown on the inorganic material-containing bar 530 to a size smaller than that of the nanoparticles 540, nano-gaps between the metal-containing nanoparticles 540 at several nanometers level can be realized.

Figure 39:
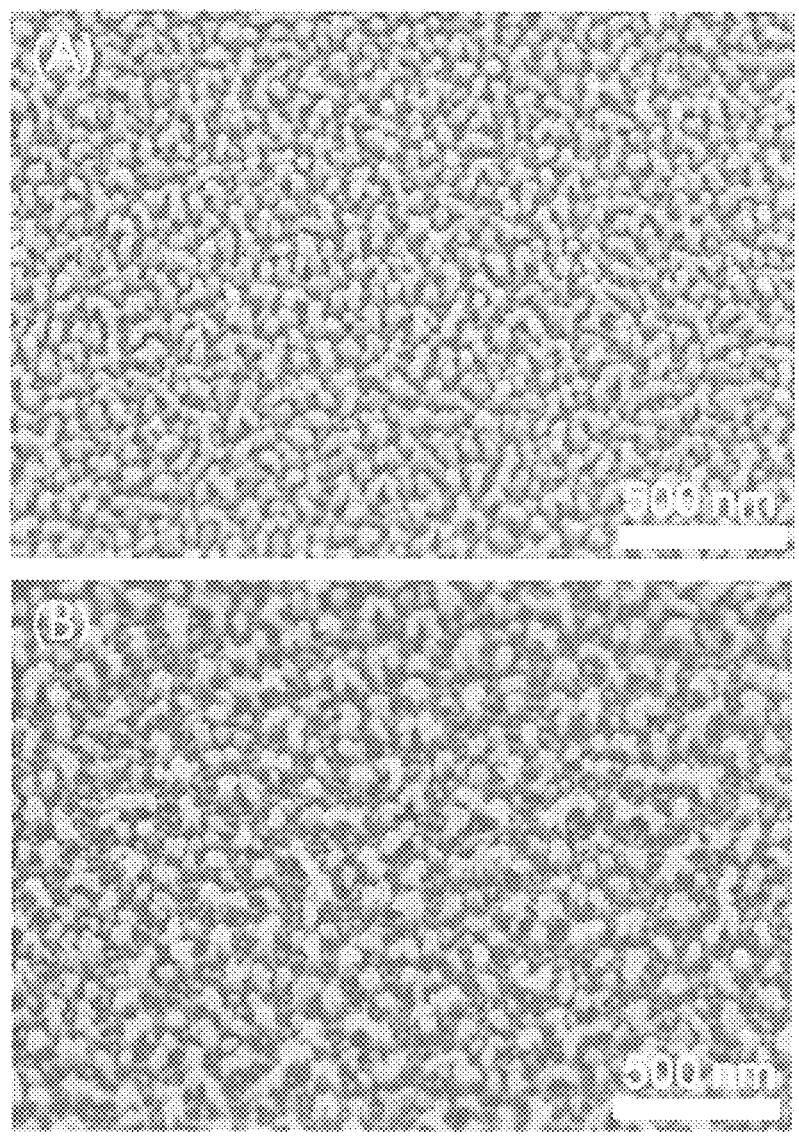
FIG. 39 illustrates SEM images of protuberant structures having different density and gap according to an example.

FIG. 39 illustrates SEM images of protuberant structures having different density and gap according to an example.

Referring to FIG. 39, it is noted that the high-formed the protuberant structures 520 (B) have lower density of the protuberant structures 520 and larger spacing between the protuberant structures 520 than the low-formed protuberant structures 520 (A).

Figure 40:
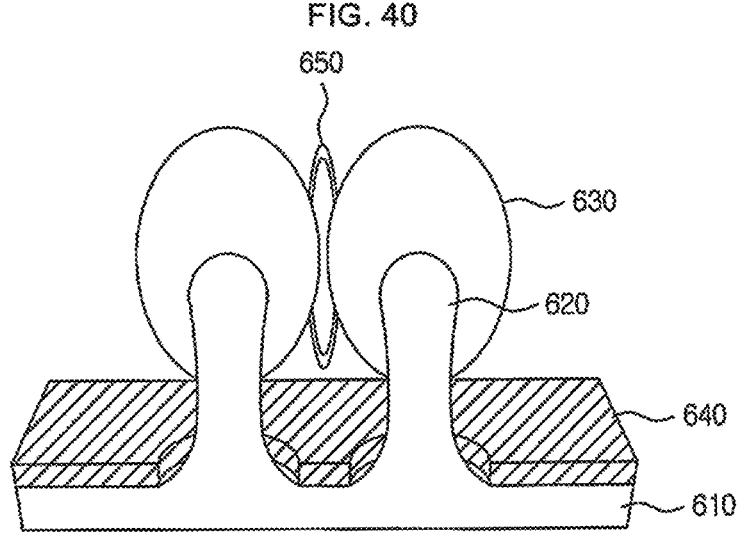
FIG. 40 is a diagram illustrating a nano-gap controlled substrate according to an example.

FIG. 40 is a diagram illustrating a nano-gap controlled substrate according to an example.

Referring to FIG. 40, a nano-gap controlled substrate according to an example may comprise a substrate 610, protuberant structures 620, metal-containing nanoparticles 630, a metal-containing thin layer 640 and nano-gaps 650.

The substrate 610 may be stretched to increase or decrease the total area of the substrate at a desired point.

The substrate 610 may be a stretchable polymer substrate, but it is not limited thereto. Even though it is not a polymer substrate but can be stretched, it may be used as the substrate 610.

The substrate 610 may be polydimethylsiloxane (PDMS).

The protuberant structures 620 may be formed by processing the substrate 610. Thus, the protuberant structures 620 may be the same material as the substrate 610.

The protuberant structures 620 may be formed by any one chosen from plasma etching, soft lithography, embossing, nano imprinting, photolithography, and holographic lithography, but it is not limited thereto.

When plasma etching is used, it is performed by using at least one chosen from argon, oxygen, hydrogen, helium, and nitrogen gas.

The upper part of the protuberant structures 620 may have a larger curvature than the lower part. When the upper part of the protuberant structures 620 is formed to have a larger curvature than the lower part, metal-containing nanoparticles 630 may be adhered better to the upper part of the protuberant structures 620 than to the surface of the substrate 610. As shown in FIG. 40, the protuberant structures 620 and metal-containing nanoparticles 630 may be formed in a tree shape and metal-containing nanoparticles 630 may be formed larger on the upper part of the protuberant structures 620. This is because the high curvature on the protuberant structures 620 leads to the accumulation of negative charges on the upper part and induces the deposition of positively charged metal ions.

The metal-containing nanoparticles 630 are formed on the protuberant structures 620.

The metal-containing nanoparticles 630 may be formed on all of the protuberant structures 620 depending on the deposition method. When the metal-containing nanoparticles 630 is deposited on the upper part of the protuberant structures 620, as shown in FIG. 40, they may be only partially deposited in spherical or elliptical shape.

The metal-containing nanoparticles 630 may be formed by vacuum depositing a Raman active material. The vacuum deposition may be performed by any one chosen from sputtering, evaporation and chemical vapor deposition, but it is not limited thereto.

The Raman active material may be any one chosen from Au, Ag, Cu, Pt, Pd and an alloy thereof, but it is not limited thereto.

The metal-containing thin layer 640 is formed on the surface of the stretchable substrate 610.

The metal-containing thin layer 640 may be formed simultaneously with the metal-containing nanoparticles 630 or may be formed by a separate process.

The metal-containing thin layer 640 and the metal-containing nanoparticles 630 may be formed by vacuum depositing a Raman active material at the same time. The Raman active material is initially uniformly deposited on the surface of the substrate 610 and the protuberant structures 620, but is intensively deposited on the upper part of the protuberant structures 620 as the deposition progresses. This is due to the shadow effect of the metal-containing nanoparticles 630 already deposited on the protuberant structures 620 as the deposition progresses.

The stretchable substrate 610 may be stretched before forming the metal-containing nanoparticles 630 and restored after forming the metal-containing nanoparticles 630. This process is intended to narrow the nano-gap 650, which is the separation distance between the metal-containing nanoparticles 630. The control of the nano-gap 650 facilitates the induction of hot spots.

There are three main factors that affect nano-gap 650: (1) spacing between the protuberant structures 620 when forming the protuberant structures 620. This can be achieved by controlling the etching time and the like when using plasma etching; (2) size of the metal-containing nanoparticles 630 which are formed on the protuberant structures 620. The size control of the metal-containing nanoparticles 630 can be achieved by controlling the deposition time and the like; and (3) elongation of the stretchable substrate 610. If the elongation is increased during the formation of the metal-containing nanoparticles 630, the interval between the metal-containing nanoparticles 630 becomes closer to that during deposition. On the other hand, if the stretching is reduced, the interval between the metal-containing nanoparticles 630 is slightly closer when being restored, compared to when the stretching is increased.

Figure 41:
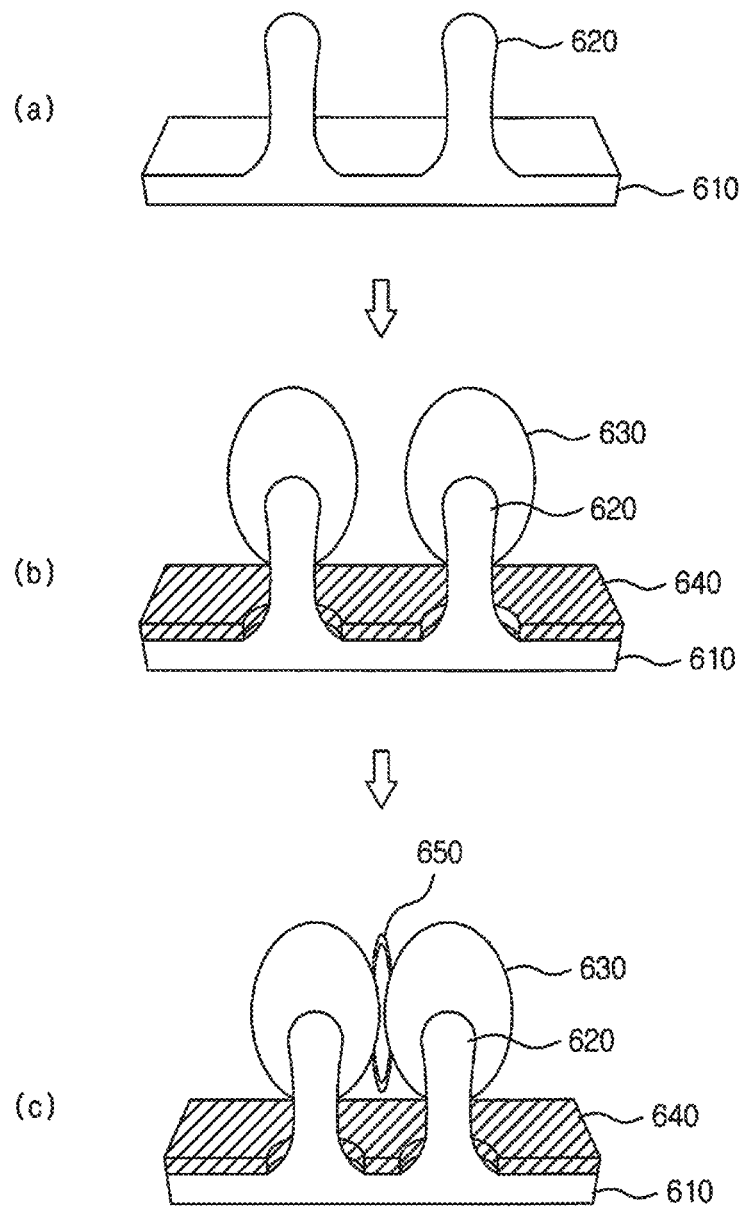
FIG. 41 is diagram illustrating a process for inducing hot spots of a nano-gap controlled substrate according to an example.

FIG. 41 is diagram illustrating a process for inducing hot spots of a nano-gap controlled substrate according to an example.

FIG. 41(A) shows the stretched substrate 610 on which the protuberant structures 620 are formed on the stretchable substrate 610. When the substrate 610 is stretched, the distance between the protuberant structures 620 becomes distant.

FIG. 41(B) shows the metal-containing thin layer 640 and the metal-containing nanoparticles 630 formed on the stretched substrate 610. The metal-containing nanoparticles 630 are formed on the protuberant structures 620 when the distance between the protuberant structures 620 are increased.

FIG. 41(C) shows the restored substrate 610 after forming the metal-containing nanoparticles 630. When the substrate 610 is unstretched, the substrate 610 returns to the state before stretching by the restoring force of the substrate 610. When the substrate 610 returns to the state before stretching, the distance between the protuberant structures 620 becomes narrower. As a result, the nano-gap 650, which is the distance between the metal-containing nanoparticles 630, also becomes narrower. As shown in FIG. 41(C), it is possible to form the nano-gaps 650 of several nanometers level, which facilitates the formation of hot spots.

Figure 42:
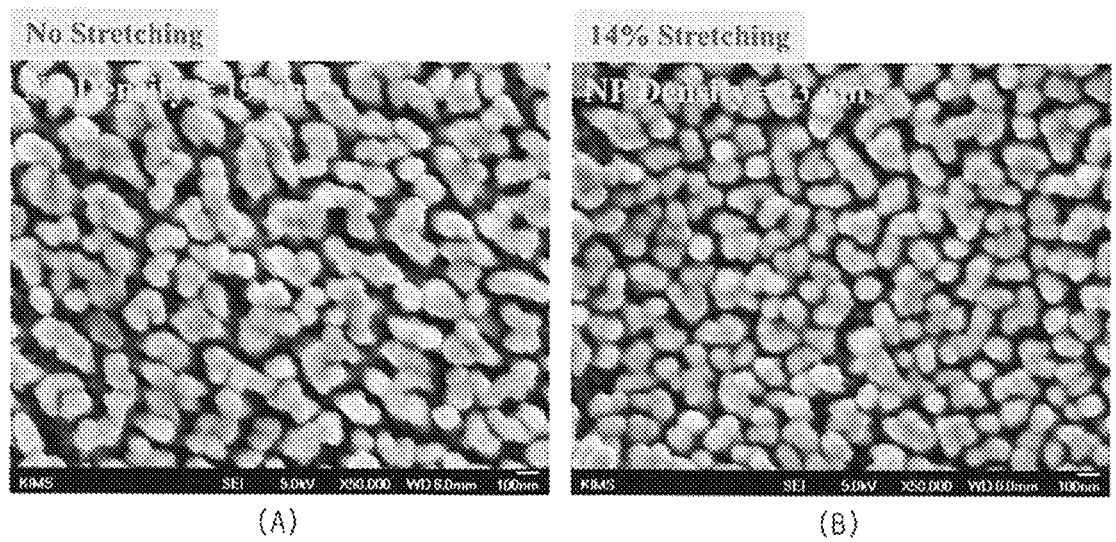
FIG. 42 illustrates results of a nano-gap controlled substrate with and without stretching.

FIG. 42 illustrates results of a nano-gap controlled substrate with and without stretching.

Example 1 will be explained with reference to FIG. 42.

Example 1

Base substrate: PDMS substrate (thickness: about 1 mm)
Initial vacuum degree: $3\times10^{-2}$ torr
Reactive ion etching
Vacuum for pretreatment process: $8\times10^{-2}$ torr
Operation gas: $CF_4$ 5 sccm
RF plasma for pretreatment Power: 100 W
Pretreatment time: 4.5 min Using a PDMS (polydimethylsiloxane) substrate 610, the surface morphology of metal-containing nanoparticles 630 after plasma treatment was observed based on the stretching.

The PDMS substrate 610 was performed for the $CF_4$ reactive ion etching to provide protuberant structures 620 with size of several tens to several hundred nanometers. The result was deposited with a Raman active material of Ag using the thermal evaporation in a 150 nm thickness.

When the substrate 610 is not stretched during the vacuum deposition, because the spacing between the protuberant structures 620 is irregular, growing metal-containing nanoparticles 630 are linked to adjacent metal-containing nanoparticles 630.

FIG. 42(A) is a SEM image illustrating the substrate 610 which is not stretched and the metal-containing nanoparticles 630 are formed thereon. Referring to FIG. 42(A), a part of the metal-containing nanoparticles 630 are linked with each other. When the metal-containing nanoparticles 630 are linked with each other, the density of the nano-gap 650 is reduced. When the stretchable substrate 610 is not used, there is a limit to lower the size of the nano-gap 650 below a certain level.

This disclosure aims to solve this problem by depositing Ag, which is a Raman active material, while stretching the PDMS substrate 610. When the substrate 610 is stretched, the distance between the protuberant structures 620 becomes greater. When Ag is vacuum deposited on the stretched substrate 610, the probability that the metal-containing nanoparticles 630 are connected to each other is lower than that in the case where the substrate 610 is not stretched, even if the size of the metal-containing nanoparticles 630 is increased.

After forming the metal-containing nanoparticles 630 by depositing a Raman active material of Ag, the restoring force of the substrate 610 returns to the state before the PDMS substrate 610 is stretched. As a result, the distance between the metal-containing nanoparticles 630 is reduced, and the connection between the metal-containing nanoparticles 630 is reduced, thereby increasing the areal density of the nano-gaps 650.

FIG. 42(B) is a SEM image illustrating the substrate 610 which is first stretched about 14%, on which a Raman active material of Ag is deposited in a thickness of 150 nm, and which is then unstretched. Referring to FIG. 42(B), it is noted that not only the number of nano-gaps 650 is increased but also the size of nano-gaps 650 is decreased as compared with the case of FIG. 42 (A). The areal density of the metal-containing nanoparticles 630 is increased by 75%. When the nano-gap 650 is reduced to a level of 5 nm or less, since the Raman signal is dramatically enhanced by the nano-gaps 650, this is called hot spots.

Example 2

Excitation laser wavelength: 514 nm
Objective lens: 50×
Spot size: 2 μm
Power: 0.15 mW After immersing the substrate 610, on which the metal-containing nanoparticles 630 are formed, in 2 mM of BT (benzenethiol) solution for 1 hour, it was rinsed with ethanol for the BT molecules to be adsorbed to the metal-containing nanoparticles 630 in a single layer. Raman signal intensity of the BT molecules was determined using a Raman spectrometer.

Figure 43:
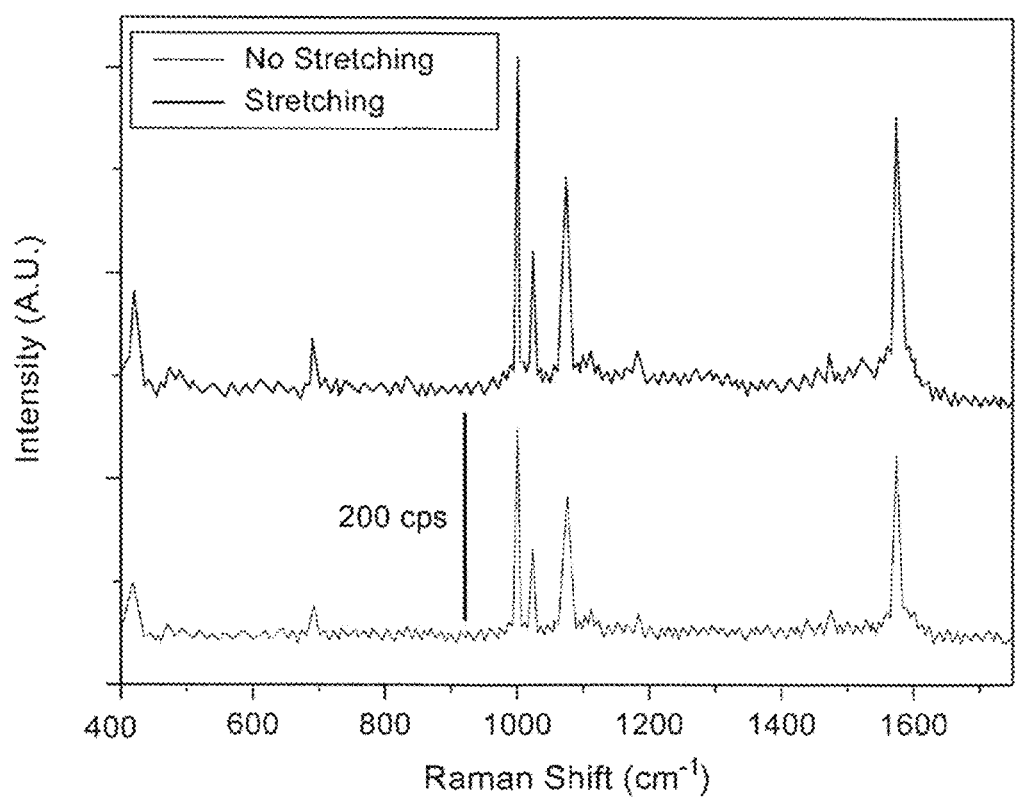
FIG. 43 illustrates Raman signals of a substrate with and without stretching.

FIG. 43 illustrates Raman signals of a substrate with and without stretching.

Referring to FIG. 43, when the substrate 610 is stretched, Raman signal intensity of the BT molecules is increased by 59% compared with a case when the substrate is manufactured without stretching.

As described above, the nano-gaps 650 can be controlled to a level of 5 nm or less. Depending on the size of the material to be analyzed, a variety of nano-gaps 650 may be formed as well as a small level of nano-gaps 650.

Adjusting the nano-gap 650 corresponding to the size of the material to be analyzed contributes to maximizing the Raman signal. For example, when analyzing a low-molecular substance such as dioxins, the size of the nano-gap 650 may be controlled to be about 1 nm, while when analyzing a polymeric material such as proteins, the size of the nano-gap 650 may be controlled to match the diameter of the protein molecule. In this way, it is possible to maximize the Raman signal by controlling the nano-gap 650 corresponding to the size of the substance to be analyzed.

Figure 44:
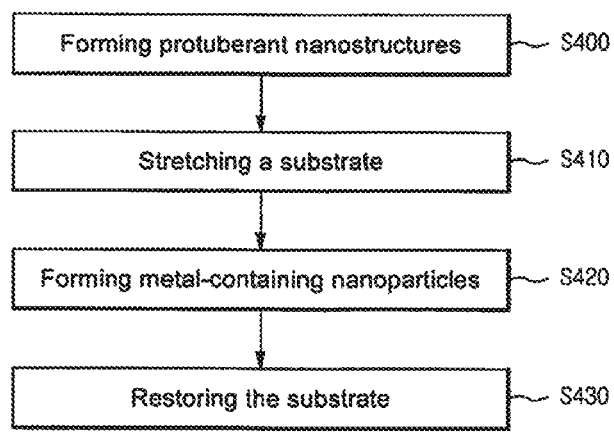
FIG. 44 is a flowchart illustrating a method for manufacturing a nano-gap controlled substrate according to an example.

FIG. 44 is a flowchart illustrating a method for manufacturing a nano-gap controlled substrate according to an example.

Referring to FIG. 44, in S400, protuberant structures 620 are formed on a stretchable substrate 610.

In S410, the substrate 610 on which the protuberant structures 620 are formed is stretched by applying a stretching force. The distance between the protuberant structures 620 becomes distant.

In S420, metal-containing nanoparticles 630 are formed on a part or all of the protuberant structures 620. A metal-containing thin layer 640 is formed on the surface of the substrate 610 and metal-containing nanoparticles 630 are formed on the protuberant structures 620 at the same time through the vacuum deposition. However, it is not limited thereto.

In S430, the substrate 610 is restored. When the stretching force to the substrate 610 is released, the stretching is restored. Here, by the restoring force of the substrate 610, the distance between the protuberant structures 620 returns before stretching and the nano-gap 650, which is the distance between the metal-containing nanoparticles 630, also becomes smaller. The nano-gap 650 can be controlled by controlling the elongation to maximize the Raman signal of the material to be analyzed.

On the other hand, an aqueous solution including an analyte may be dropped during the process for manufacturing the substrate 610 for the surface-enhanced Raman spectroscopy.

Figure 45:
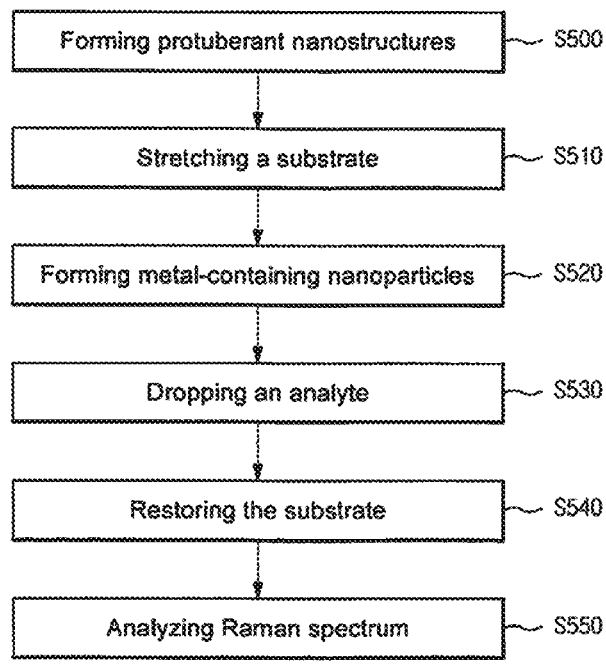
FIG. 45 is a flowchart illustrating an analysis method using a nano-gap controlled substrate according to an example.

FIG. 45 is a flowchart illustrating an analysis method using a nano-gap controlled substrate according to an example.

Referring to FIG. 45, In S500, protuberant structures 620 are formed by processing a stretchable substrate 610.

In S510, the substrate 610 on which the protuberant structures 620 are formed is stretched by applying a stretching force. The distance between the protuberant structures 620 becomes distant.

In S520, metal-containing nanoparticles 630 are formed on the protuberant structures 620.

In S530, an aqueous solution including an analyte is dropped on the substrate 610. Since the substrate 610 is stretched, the analyte can enter between the metal-containing nanoparticles 630.

In S540, the substrate 610 is restored so that the metal-containing nanoparticles 630 capture the analyte. When the substrate is restored, the distance between the metal-containing nanoparticles 630 is reduced by the restoring force of the substrate 610 and during this process, the analyte can be captured in the nano-gaps 650. Once the analyte is captured, the Raman signal can be further maximized in Raman analysis.

In S550, the analyte captured between the metal-containing nanoparticles 630 is analyzed using a Raman spectrometer.

Figure 46:
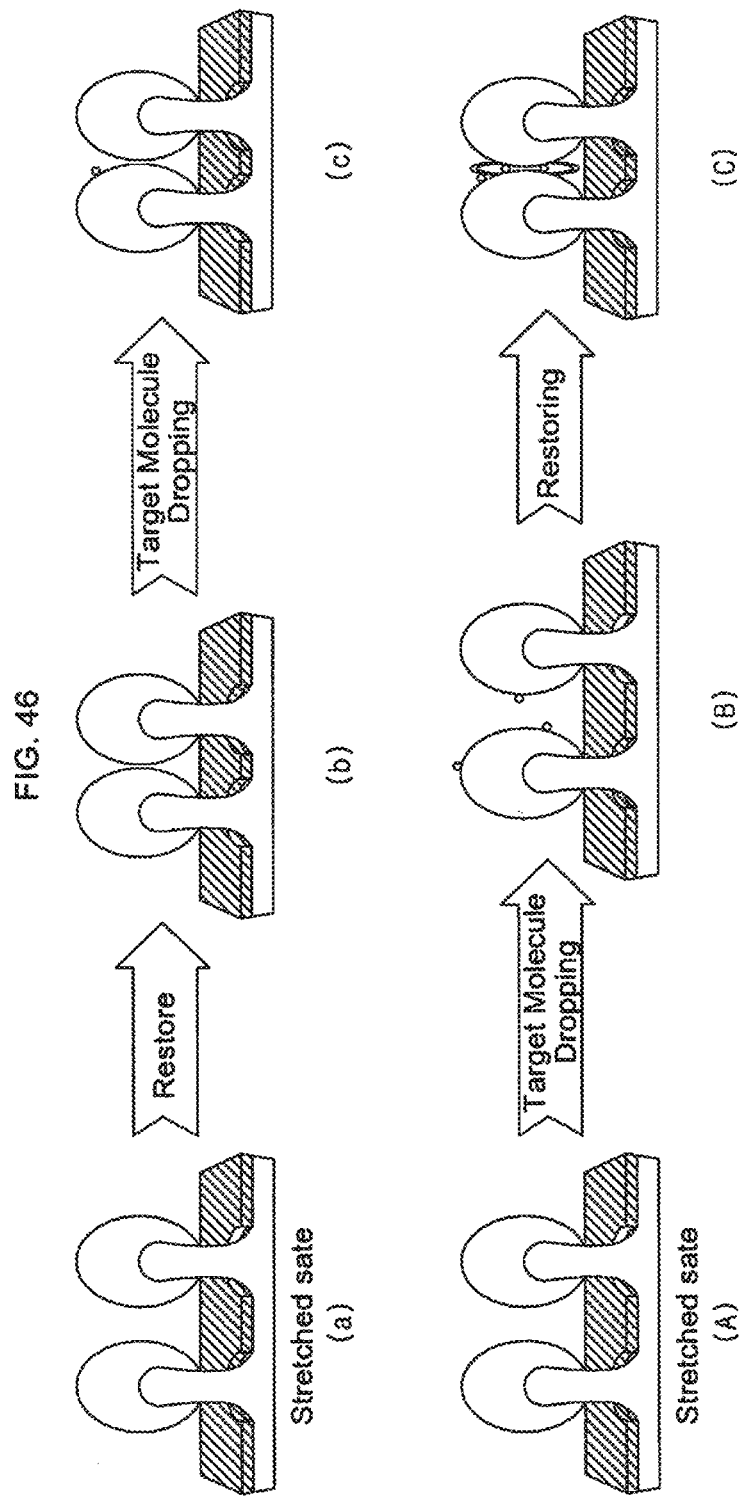
FIG. 46 illustrates diagrams for explaining a structure for capturing an analyte.

FIG. 46 illustrates diagrams for explaining a structure for capturing an analyte.

FIGS. 46(a) and 46(b) illustrate the state that the stretching is released after the metal-containing nanoparticles 630 are formed. FIG. 46(c) illustrates the state that an analyte is dropped on the substrate 610 of which stretching is released. Here, molecule trapping is not occurred.

FIG. 46(A) illustrates the state that the substrate 610, on which the metal-containing nanoparticles 630 are formed, is stretched. FIG. 46(B) illustrates the state that an analyte is dropped on the substrate 610 which is stretched. FIG. 46(C) illustrates the state that an analyte is captured (marked as an ellipse) and the substrate 610 is restored. In this case, the analyte is positioned directly on the nano-gap 650, so that the Raman signal can be maximized.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A substrate with multiple nano-gaps comprising: a substrate including protuberant structures formed to be spaced-apart on a surface of the substrate by plasma etching of a polymer substrate; a metal-containing thin layer continuously between the substrate including protuberant structures and an insulation layer; and metal-containing nanoparticles on the insulation layer, wherein the metal-containing nanoparticles have nano-gaps with other metal-containing nanoparticles and with the metal-containing thin layer, wherein the metal-containing nanoparticles on the protuberant structures have a spherical or elliptical shape, wherein an upper part of the protuberant structure has a larger radius of curvature than a lower part of the protuberant structure, wherein the metal-containing thin layer includes a Raman active material, and wherein the Raman active material has a first thickness on the substrate including protuberant structures and has a second thickness on an upper surface the protuberant structures.

2. A Raman spectroscopic device comprising
a light source;
the substrate of claim 1; and
a detector configured to detect Raman spectrum.

3. A substrate comprising multiple nano-gaps comprising: a substrate including protuberant structures formed to be spaced-apart from each other by plasma etching of a polymer substrate: metal-containing nanoparticles; and a continuous layer between the substrate including protuberant structures and metal-containing nanoparticles and comprising at least one inorganic material-containing thin layer, and at least one metal-containing thin layer, wherein the nano-gaps are between the metal-containing nanoparticles, and are between the metal-containing nanoparticles and the metal-containing thin layer, wherein the metal-containing nanoparticles on the protuberant structures have a spherical or elliptical shape, wherein an upper part of the protuberant structure has a larger radius of curvature than a lower part of the protuberant structure, wherein the metal-containing thin layer includes a Raman active material and wherein the Raman active material has a first thickness on the substrate including protuberant structures and has a second thickness on an upper surface the protuberant structures.

4. The substrate comprising multiple nano-gaps of claim 3, wherein the continuous layer includes two metal-containing thin layers and an inorganic material-containing thin layer therebetween, and wherein the nano-gaps are between the two metal-containing thin layers.

5. The substrate comprising multiple nano-gaps of claim 3, wherein the continuous layer includes a first inorganic material-containing thin layer, a metal-containing thin layer, and a second inorganic material-containing thin layer.

6. The substrate comprising multiple nano-gaps of claim 3, wherein the continuous layer includes a metal-containing thin layer and an inorganic material-containing thin layer.

7. A substrate comprising multiple nano-gaps comprising: a substrate including protuberant structures formed to be spaced-apart from each other by plasma etching of a polymer substrate; metal-containing nanoparticles on a surface of the substrate including protuberant structures; and a continuous layer underneath the metal-containing nanoparticles and comprising at least one inorganic material-containing thin layer and at least one metal-containing thin layer, wherein the nano-gaps are between the metal-containing nanoparticles, and are between the metal-containing nanoparticles and the metal-containing thin layer, wherein the metal-containing nanoparticles on the protuberant structures have a spherical or elliptical shape, wherein an upper part of the protuberant structure has a larger radius of curvature than a lower part of the protuberant structure, wherein the metal-containing thin layer includes a Raman active material, and wherein the Raman active material has a first thickness on the substrate including protuberant structures and has a second thickness on an upper surface the protuberant structures.

8. The substrate comprising multiple nano-gaps of claim 7, wherein the continuous layer includes two metal-containing thin layers and inorganic material-containing thin layer therebetween, and
wherein the nano-gaps are between the two metal-containing thin layers.

9. The substrate comprising multiple nano-gaps of claim 7, wherein the continuous layer includes a first inorganic material-containing thin layer, a metal-containing thin layer, and a second inorganic material-containing thin layer.

10. The substrate comprising multiple nano-gaps of claim 7, wherein the continuous layer includes a metal-containing thin layer and an inorganic material-containing thin layer.

11. A substrate with inorganic-containing particles comprising: a substrate including protuberant structures formed to be spaced-apart from each other by plasma etching of a polymer substrate; inorganic-containing particles continuously on a surface of the substrate including protuberant structures; and metal-containing nanoparticles on the inorganic-containing particles, wherein the metal-containing nanoparticles have nano-gaps with at least one of (i) the metal-containing nanoparticles on the protuberant structures and (ii) the metal-containing nanoparticles on an area of the substrate without protuberant structures, wherein the inorganic-containing particles on the protuberant structures have a spherical or elliptical shape, wherein an upper part of the protuberant structure has a larger radius of curvature than a lower part of the protuberant structure, wherein the inorganic-containing particles are formed by vacuum depositing an inorganic material, and wherein inorganic-containing particles have a first thickness on the substrate including protuberant structures and has a second thickness on an upper surface the protuberant structures.

12. The substrate with inorganic-containing particles of claim 11, wherein a material of the inorganic-containing particles is one selected from the group consisting of an oxide, a nitride, an oxynitride, a halide, and a sulfide of a metal chosen from Al, Ba, Be, Ca, Cr, Cu, Cd, Dy, Ga, Ge, Hf, In, Lu, MS, Mo, Ni, Rb, Sc, Si, Sn, Ta, Te, Ti, W, Zn, Zr, and Yb, and magnesium fluoride.

13. An inorganic material-grown substrate comprising: a substrate including protuberant structures formed to be spaced-apart from each other by plasma etching of a polymer substrate; an inorganic material-containing bar continuously along the protuberant structures-: metal-containing nanoparticles on the inorganic material-containing bar; a first inorganic material-containing layer on a surface of the substrate; and nano-gaps between the metal-containing nanoparticles, wherein inorganic containing particles on the protuberant structures have a spherical or elliptical shape, wherein an upper part of the protuberant structure has a larger radius of curvature than a lower part of the protuberant structure, wherein the inorganic material has a first thickness on the substrate including protuberant structures and has a second thickness on an upper surface the protuberant structures.

* * * * *